(12) United States Patent
McPhee

(10) Patent No.: US 8,492,605 B2
(45) Date of Patent: Jul. 23, 2013

(54) MICROBIAL DERIVED ISOPRENE AND METHODS FOR MAKING THE SAME

(71) Applicant: Derek McPhee, Emeryville, CA (US)

(72) Inventor: Derek McPhee, Emeryville, CA (US)

(*) Notice: Subject to any disclaimer, the term of this patent is extended or adjusted under 35 U.S.C. 154(b) by 0 days.

(21) Appl. No.: 13/629,623

(22) Filed: Sep. 28, 2012

(65) Prior Publication Data

US 2013/0030227 A1    Jan. 31, 2013

Related U.S. Application Data

(62) Division of application No. 12/659,216, filed on Mar. 1, 2010, now Pat. No. 8,324,442.

(60) Provisional application No. 61/202,474, filed on Mar. 3, 2009.

(51) Int. Cl.
*C07C 7/00* (2006.01)

(52) U.S. Cl.
USPC ......... 585/810; 585/809; 435/167; 435/252.3

(58) Field of Classification Search
None
See application file for complete search history.

(56) References Cited

U.S. PATENT DOCUMENTS

| | | | |
|---|---|---|---|
| 7,931,873 B2 | 4/2011 | Lovegrove et al. | |
| 2008/0020438 A1* | 1/2008 | Matsuda et al. | 435/167 |
| 2010/0086978 A1* | 4/2010 | Beck et al. | 435/131 |
| 2010/0184178 A1* | 7/2010 | Beck et al. | 435/167 |
| 2010/0196977 A1* | 8/2010 | Chotani et al. | 435/158 |
| 2011/0178261 A1* | 7/2011 | Feher et al. | 526/340.2 |

FOREIGN PATENT DOCUMENTS

| | | |
|---|---|---|
| WO | WO2008137092 | 11/2008 |
| WO | WO2009100231 | 8/2009 |
| WO | WO2010101855 | 9/2010 |

OTHER PUBLICATIONS

Newman, et al., "High-level Production of Amorpha-4,11-Diene in a Two-Phase Partitioning Bioreactor of Metabolically Engineered *Escherichia coli*", Biotechnology and Bioengineering, vol. 95. No. 4, Nov. 5, 2006, pp. 684-691.

* cited by examiner

*Primary Examiner* — Tam M Nguyen
(74) *Attorney, Agent, or Firm* — Kam W. Law; Squire Sanders (US) LLP

(57) ABSTRACT

A method for producing isoprene comprising an aqueous medium including genetically modified host cells capable of producing isoprene, where the resulting isoprene composition is processed through at least one separation and/or purification process to provide an isoprene enriched composition and a system for doing the same.

13 Claims, 9 Drawing Sheets

MICROBIAL DERIVED ISOPRENE AND METHODS FOR MAKING THE SAME

CROSS REFERENCE TO RELATED APPLICATION

This is a divisional application of the U.S. Non-Provisional application Ser. No. 12/659,216, now U.S. Pat. No. 8,324,442, which claims the benefit of priority from U.S. Provisional Application No. 61/202,474, filed Mar. 3, 2009, all of which, in their entirety, are incorporated herein by reference.

BACKGROUND OF THE INVENTION

Isoprene is a five carbon hydrocarbon (2-methyl-1,3-butadiene), that is an industrial chemical used in a range of industrial application such as tires, footwear, sporting goods, latex, tapes, labels, and medical disposables. Isoprene is also a natural compound produced in biological systems. While isoprene is made naturally in various organisms ranging from microbes to animals, most naturally occurring isoprene has traditionally been extracted from rubber plants. However, extraction yields are low and these quantities are far less than are required for many commercial applications. As a result, isoprene is primarily produced synthetically from petroleum sources, most often from ethylene using a steam cracking process.

Due to the growing concern for climate change and thus a need to make products we need more sustainably, there is an urgent need for bio- or renewable isoprene that will help meet global isoprene demands but that can be produced in a more environmentally friendly way. The current invention addresses this need.

SUMMARY OF THE INVENTION

The present invention provides microbial derived isoprene compositions and methods for making and purifying the same.

In one aspect of the invention, a gaseous isoprene composition is provided comprising: isoprene and water wherein the water is present in an amount greater than about 70% of its saturation amount and wherein the gaseous isoprene composition comprises 1 part per million or less than 1 part per million of any one of the following impurities: $C_2$-$C_5$ alkynes, cyclopentadiene, piperylene, and 1,4-pentadiene.

In another aspect a liquid isoprene composition is provided comprising: at least 65% isoprene by weight and wherein the isoprene composition comprises 1 part per million or less than 1 part per million of any one of the following impurities: $C_2$-$C_5$ alkynes, cyclopentadiene, piperylene, and 1,4-pentadiene.

In another aspect, a method for making and purifying isoprene is provided. The method comprises:
a. obtaining a first gaseous composition comprising isoprene and water wherein the gaseous composition comprises 1 part per million or less of $C_2$-$C_5$ alkynes;
b. flowing the first gaseous composition through a first chiller wherein the first chiller has a temperature of between about 10° C. and about −15° C. thereby resulting in a second gaseous composition and wherein the second gaseous composition comprises less water than the first gaseous composition;
c. flowing the second gaseous composition through a second chiller wherein the second chiller has a temperature below −35° C.; and
d. collecting the resulting liquid isoprene composition.

In another aspect, another method is provided. The method comprises:
a. culturing a plurality of host cells capable of making isoprene;
b. forming a first gaseous composition comprising isoprene and water wherein the water is present in an amount greater than about 70% of its saturation amount;
c. subjecting the first gaseous composition to a first cooling step whereby substantially all of the water is removed from the first gaseous composition resulting a second gaseous composition; and
d. subjecting the second gaseous composition to a second cooling step whereby a liquid isoprene composition is collected.

In another aspect, another method is provided. The method comprises:
a. culturing a plurality of host cells capable of making isoprene;
b. forming a first gaseous composition comprising isoprene and water wherein the water is present in an amount greater than about 70% of its saturation amount;
c. subjecting the first gaseous composition to a first cooling step whereby substantially all of the water is removed from the first gaseous composition resulting a second gaseous composition;
d. subjecting the second gaseous composition to a second cooling step whereby a liquid isoprene composition is collected; and
e. optionally, contacting either the first gaseous composition, the second gaseous composition and/or the liquid isoprene composition with a membrane containing modified zeolites or molecular seive to provide a purified isoprene composition.

In another aspect, another method is provided. The method comprises:
a. contacting a plurality of host cells capable of making isoprene in an aqueous medium wherein the aqueous medium is in contact with an immiscible organic liquid and the aqueous medium, the host cells, and the immiscible organic liquid is in a closed vessel; and
b. culturing the host cells in the aqueous medium whereby the host cells make isoprene and the isoprene is captured in the immiscible organic liquid.

In another aspect, another method is provided. The method comprises:
a. obtaining a first gaseous composition comprising:
  i. isoprene in an amount between about 0.1% and about 15% by volume;
  ii. carbon dioxide in an amount between about 0.04% and about 35% by volume;
  iii. oxygen in an amount between about 1% and about 20% by volume;
  iv. nitrogen in an amount greater than about 50% by volume;
  v. argon in an amount less than about 0.9% by volume;
  vi. water in an amount greater than about 70% of its saturation amount;
  vii. 1 part per million or less of C2-C5 alkyne, cyclopentadiene, piperylene, and 1,4-pentadiene; and
  viii. ethanol;
b. flowing the first gaseous composition through a first chiller and an operably connected flash drum, wherein the first chiller has a temperature of between about 10° C. and about −15° C. thereby resulting in a second gaseous composition and wherein the second gaseous composition comprises less water than the first gaseous composition;

c. flowing the second gaseous composition through a second chiller and an operably connected flash drum, wherein the second chiller has a temperature between about 35° C. and about −85° C.; and
d. collecting the resulting liquid isoprene composition.

An isoprene production system comprising:
a. a bioreactor capable of culturing a plurality of host cells;
b. a first chiller and flash drum operably connected to the overhead stream of the bioreactor, the first chiller capable of operating in a temperature range of between 10° C. and −15° C.; and
c. a second chiller and flash drum operably connected to the overhead stream exiting from the first chiller and flash drum, the second chiller capable of operating in a temperature below −35° C.

In yet another aspect, an isoprene production system is provided. The system comprises:
a. a closed vessel;
b. an aqueous medium, within the vessel, forming a first phase;
c. a plurality of host cells, within the aqueous medium, capable of making isoprene; and,
d. a liquid organic second phase, capable of capturing the isoprene made by the host cells, in contact with the first phase.

DETAILED DESCRIPTION OF THE INVENTION

Definitions

Figure 1:
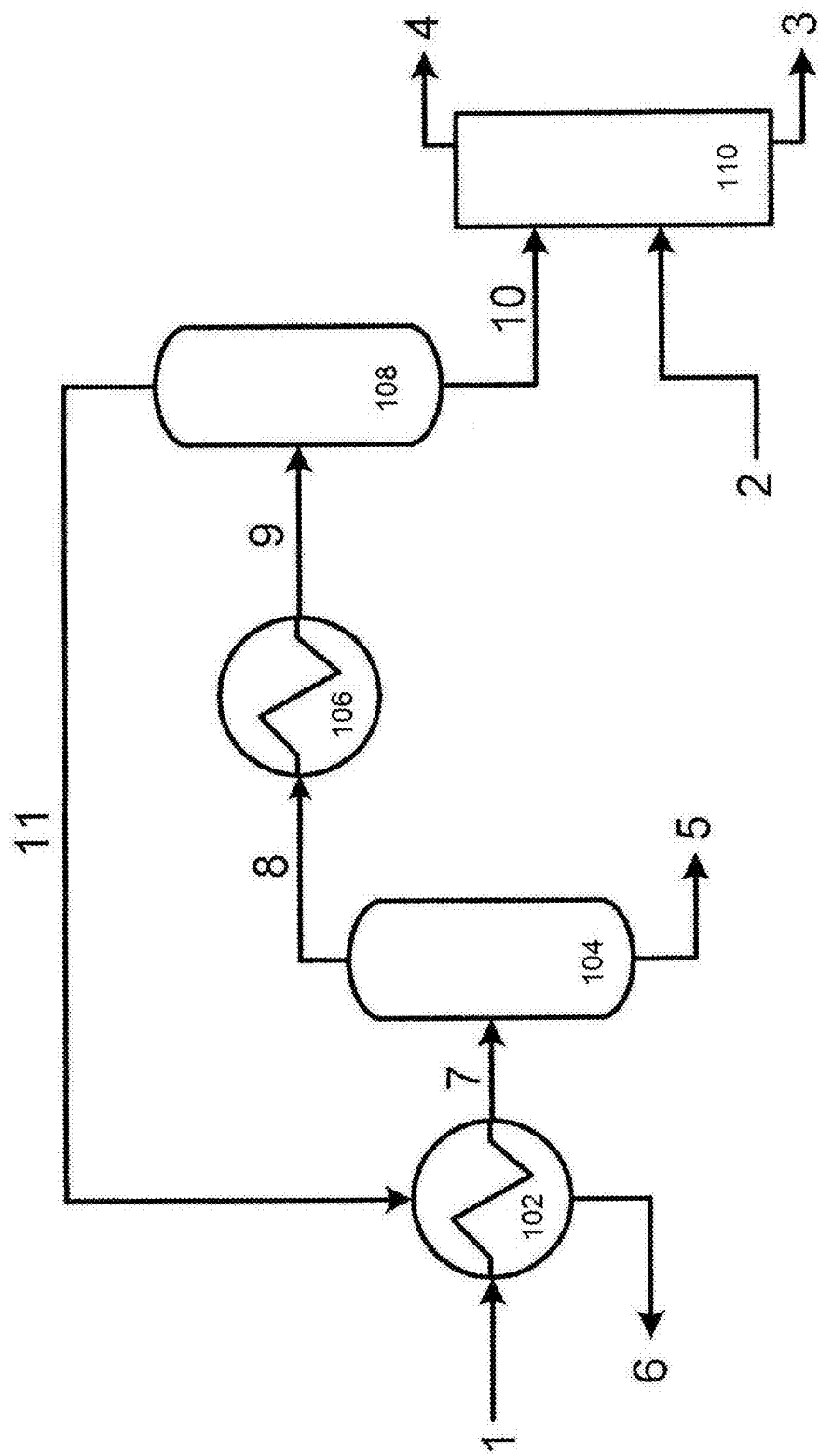
FIG. 1 is a schematic representation of an exemplary separation system.

Unless defined otherwise, all technical and scientific terms used herein have the same meaning as commonly understood by one of ordinary skill in the art to which this invention belongs. Reference is made here to a number of terms that shall be defined to have the following meanings:

"Bio-organic compound" refers to an organic compound having at least five carbon atoms that can be made by a host cell by taking a carbohydrate carbon source and converting the carbohydrate carbon source into the desired product.

"Deoxyxylulose 5-phosphate pathway" or "DXP pathway" is used herein to refer to the pathway that converts glyceraldehyde-3-phosphate and pyruvate to IPP and DMAPP. The DXP pathway is illustrated schematically in FIG. 4.

"Endogenous" refers to a substance or process that can occur naturally, e.g., in a non-recombinant host cell.

"Heterologous nucleic acid" as used herein refers to a nucleic acid wherein at least one of the following is true: (a) the nucleic acid is foreign ("exogenous") to (that is, not naturally found in) a given host cell; (b) the nucleic acid comprises a nucleotide sequence that is naturally found in (that is, is "endogenous to") a given host cell, but the nucleotide sequence is produced in an unnatural (for example, greater than expected or greater than naturally found) amount in the cell; (c) the nucleic acid comprises a nucleotide sequence that differs in sequence from an endogenous nucleotide sequence, but the nucleotide sequence encodes the same protein (having the same or substantially the same amino acid sequence) and is produced in an unnatural (for example, greater than expected or greater than naturally found) amount in the cell; or (d) the nucleic acid comprises two or more nucleotide sequences that are not found in the same relationship to each other in nature (for example, the nucleic acid is recombinant).

"Host cell" and "microorganism" are used interchangeably herein to refer to any archae, backterial, or eukaryotic living cell into which a heterologous nucleic acid can be or has been inserted. The term also relates to the progeny of the original cell, which may not necessarily be completely identical in morphology or in genoic or total DNA complement to the original parent, due to natural, accidental, or deliberate mutation.

"Isoprenoid" and "isoprenoid compound" are used interchangeably herein and refer to a compound derivable from isopentenyl diphosphate.

"Isolate" and "isolating" when referred to a bio-organic compound is the enrichment of the amount of the bio-organic compound in a composition. Consequently, the amount of the bio-organic compound in a composition after the bio-organic compound has been isolated or subject to an isolating step is greater than the amount present in the composition prior to such step.

"Mevalonate pathway" or "MEV pathway" is used herein to refer to the biosynthetic pathway that converts acetyl-CoA to IPP. The MEV pathway is illustrated schematically in FIG. 3.

"Naturally occurring" as applied to a nucleic acid, an enzyme, a cell, or an organism, refers to a nucleic acid, enzyme, cell, or organism that is found in nature. For example, a polypeptide or polynucleotide sequence that is present in an organism that can be isolated from a source in nature and that has not been intentionally modified by a human in the laboratory is naturally occurring.

"Optional" or "optionally" means that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where the event or circumstance does not occur.

"Pyrophosphate" is used interchangeably herein with "diphosphate".

As used herein, a composition that is a "substantially pure" compound is substantially free of one or more other compounds, i.e., the composition contains greater than 80 vol. %, greater than 90 vol. %, greater than 95 vol. %, greater than 96 vol. %, greater than 97 vol. %, greater than 98 vol. %, greater than 99 vol. %, greater than 99.5 vol. %, greater than 99.6 vol. %, greater than 99.7 vol. %, greater than 99.8 vol. %, greater than 99.9 vol. % of the compound; or less than 20 vol. %, less than 10 vol. %, less than 5 vol. %, less than 4 vol. %, less than 3 vol. %, less than 2 vol. %, less than 1 vol. %, less than 0.5 vol. %, less than 0.1 vol. %, or less than 0.01 vol. % of the one or more other compounds, based on the total volume of the composition.

In the following description, all numbers disclosed herein are approximate values, regardless whether the word "about" or "approximate" is used in connection therewith. They may vary by 1 percent, 2 percent, 5 percent, or, sometimes, 10 to 20 percent. Whenever a numerical range with a lower limit, RL and an upper limit, RU, is disclosed, any number falling within the range is specifically disclosed. In particular, the following numbers within the range are specifically disclosed: R=RL+k*(RU−RL), wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

In addition to the definitions above, certain compounds described herein have one or more double bonds that can exist as either the Z or E isomer. The invention in certain embodiments encompasses these compounds as individual isomers in a substantially pure form as well as mixtures of various isomers, e.g., racemic mixtures of stereoisomer.

Current Sources of Isoprene

Isoprene currently is made naturally by rubber plants (typically *Hevea brasiliensis*) or is made synthetically from petroleum sources. When made naturally, the sap-like extract (known as latex and is a polymerized version of isoprene) is collected from the rubber plants and is the primary source of natural rubber. Because latex and natural rubber can be of varying quality (irregular molecular distribution), the synthetic analog of natural rubber or polyisoprene is often preferred due to its higher uniformity.

Chemically synthesized isoprene is made primarily from petroleum sources. The most common method involves stream cracking a petroleum stream to make ethylene which in turn is subsequently converted into isoprene. Other methods for making isoprene include isobutylene carbonylation and isopentane dehydrogenation. The resulting isoprene is produced and sold in different concentrations. Crude isoprene has a purity between 15% and 65%. Refined isoprene is defined as isoprene having a purity between 65% and 95%. High purity isoprene is defined as isoprene having a purity between 95% and 99.5%. Polymer grade isoprene is isoprene with a purity exceeding 99.5%.

As a consequence of how it is made, synthetic isoprene contains a number of impurities including various acetylenes and dienes such as cyclopentadiene and piperylene. Although these catalysts are undesirable as they inhibit polymerization, it is not often economical to entirely eliminate them and the purity of the isoprene is matched to the desired end product. For example, the isoprene purity required to make butyl rubber is substantially less that required to make SIS polymers (polymer grade).

Microbially Derived Gaseous Isoprene Compositions

The present invention provides microbial derived isoprene compositions and methods for making and purifying the same. Microbial-derived isoprene compositions differ from petroleum derived sources in that the compositions include virtually none of the following impurities: $C_2$-$C_5$ alkynes; cyclopentadiene, piperylene and 1,4-pentadiene.

In one aspect of the invention, a gaseous isoprene composition is provided. The composition comprises isoprene and water wherein the water is present in an amount that is at least about 70% of its saturation amount and the composition comprises 1 part per million or less of $C_2$-$C_5$ alkynes. Illustrative examples of $C_2$-$C_5$ alkynes include acetylene, isopropylacetylene, 1-pentyne, 2-pentyne, and 2-butyne.

In another aspect of the invention, another gaseous isoprene composition is provided. The composition comprises isoprene and water wherein the water is present in an amount that is at least about 70% of its saturation amount and the composition comprises 1 part per million or less of cyclopentadiene.

In another aspect of the invention, another gaseous isoprene composition is provided. The composition comprises isoprene and water wherein the water is present in an amount that is at least about 70% of its saturation amount and the composition comprises 1 part per million or less of piperylene.

In another aspect of the invention, another gaseous isoprene composition is provided. The composition comprises isoprene and water wherein the water is present in an amount that is at least about 70% of its saturation amount and the composition comprises 1 part per million or less of 1,4-pentadiene.

In another aspect of the invention, another gaseous isoprene composition is provided. The composition comprises isoprene and water wherein the water is present in an amount that is at least about 70% of its saturation amount and the composition comprises 1 part per million or less of each of $C_2$-$C_5$ alkynes, cyclopentadiene, piperylene, and 1,4-pentadiene.

In some embodiments, the gaseous isoprene composition comprises isoprene that is present between about 0.1% and about 15% by volume. In other embodiments, the isoprene is present between about 1 and 10% by volume. In still other embodiments, the isoprene is present between about 1 and 5% by volume. In yet other embodiments, the isoprene is present between about 5% and about 10% by volume. In further embodiments, the isoprene is present between in an amount greater than about 10% by volume.

In other embodiments, the gaseous isoprene composition comprises water in an amount that is greater than about 70%, 75%, 80%, 85%, 90%, 95% and 99% of its saturation amount. In still other embodiments, the gaseous isoprene composition comprises saturated water.

In other embodiments, the gaseous isoprene composition further comprises carbon dioxide that is present in an amount that is greater than about 0.04% by volume. In still other embodiments, the carbon dioxide is present in an amount that is greater than about 0.05%, 0.1%, 0.5%, 1.0%, and 5% by volume. In further embodiments, the carbon dioxide is present in an amount that is greater than about 10%, about 20%, about 30% by volume. In still further embodiments, the carbon dioxide is present in an amount that is between about 1% and about 35% by volume. In still other embodiments, carbon dioxide is present in an amount that is between about 10% and about 30% by volume.

In other embodiments, the gaseous isoprene composition further comprises oxygen. In some embodiments, the oxygen is present in an amount that is less than about 20.9% by volume. In other embodiments, the oxygen is present in an amount that is between about 1% by volume and about 20% by volume. In other embodiments, the oxygen is present in an amount that is between about 8% and about 15% by volume. In other embodiments, the oxygen is present in an amount that is less than about 20%, 15%, 10%, 9%, 8%, 7%, 6%, 5%, 4%, 3%, and 2%. In still other embodiments, the oxygen is present in an amount that is less than about 1% by volume. In further embodiments, the oxygen is present between about 1% and about 15% by volume. In still further embodiments, the oxygen is present between about 5% and about 15% by volume.

In other embodiments, the gaseous isoprene composition further comprises nitrogen. In some embodiments, the nitrogen is present in an amount between about 50% and about 75% by volume. In further embodiments, the nitrogen is present in an amount that is greater than about 70%. In other embodiments, the nitrogen is present in an amount that is greater than about 75%, 76%, 77%, 78%, 79%, and 80%.

In other embodiments, the gaseous isoprene composition further comprises argon. In some embodiments, the argon is present in an amount that is less than about 0.9% by volume. In other embodiments, the argon is present in an amount that is greater than about 1.0% by volume.

In other embodiments, the gaseous isoprene composition further comprises ethanol. In some embodiments, the ethanol is present in an amount that is less than about 0.5% by volume. In other embodiments, the ethanol is present in an amount that is more than about 1% by volume.

In other embodiments, the microbial-derived gaseous isoprene composition may comprise: isoprene in an amount between about 0.1% and about 15% by volume; water in an amount that is greater than about 70% of its saturation amount; carbon dioxide in an amount that is between about 0.04% and about 35% by volume; oxygen in an amount that is between about 1% and about 20% by volume; nitrogen in an amount that is greater than about 50% by volume; argon in an amount that is less than about 0.9% by volume; ethanol in an amount that is less than about 0.5% by volume; 1 part per million or less of $C_2$-$C_5$ alkynes; 1 part per million or less of cyclopentadiene; 1 part per million or less of piperylene; and 1 part per million or less of 1,4-pentadiene.

In other embodiments, the microbial-derived gaseous isoprene composition may comprise: isoprene in an amount between about 0.1% and about 15% by volume; water in an amount that is greater than about 70% of its saturation amount; carbon dioxide in an amount that is between about 0.04% and about 35% by volume; oxygen in an amount that is between about 1% and about 20% by volume; nitrogen in an amount that is greater than about 50% by volume; argon in an amount that is greater than about 1.0% by volume; ethanol in an amount that is more than about 1% by volume; 1 part per million or less of $C_2$-$C_5$ alkynes; 1 part per million or less of cyclopentadiene; 1 part per million or less of piperylene; and 1 part per million or less of 1,4-pentadiene.

In certain other embodiments, another gaseous isoprene composition is provided. This composition comprises:
   a. isoprene in an amount between about 0.1% and 15% by volume;
   b. carbon dioxide in an amount between about 1% and 35% by volume; and,
   c. water in an amount that is greater that about 70% of its saturation amount and wherein the gaseous isoprene composition comprises 1 part per million or less of $C_2$-$C_5$ alkynes. In other embodiments, the gaseous isoprene composition comprises 1 part per million or less of each of $C_2$-$C_5$ alkynes, cyclopentadiene, piperylene, and 1,4-pentadiene. In still other embodiments, the gaseous isoprene composition comprises saturated water. In yet other embodiments, the gaseous isoprene composition further comprises oxygen in an amount between about 8% and about 15% by volume or nitrogen in an amount between about 50% and 75% by volume or both.

The temperature of the above described gaseous compositions is at least 30° C. In some cases, the temperature is between about 30° C. and about 60° C. In other cases, the temperature is between about 30° C. and about 38° C.

The pressure of the above described gaseous compositions is between about 1 and about 2.5 atmospheres.

For some of the above described gaseous compositions, the temperature is between about 30° C. and about 35° C. and is at a pressure between about 1 and about 2.5 atmospheres.

Microbially Derived Liquid Isoprene Compositions

Using the methods described herein, the gaseous isoprene compositions of the present invention can be further purified to liquid isoprene. Thus in another aspect of the invention, a liquid isoprene composition is provided that results from the inventive methods. The resulting liquid isoprene composition comprises at least 65% isoprene by weight and wherein the liquid isoprene composition comprises 1 part per million or less of $C_2$-$C_5$ alkynes, cyclopentadiene, piperylene, and 1,4-pentadiene.

In some embodiments, the liquid isoprene composition comprises at least about 70%, 75%, 80%, 85%, and 90% isoprene by weight. In other embodiments, the liquid isoprene comprises at least about 95%, 96%, 97%, 98%, 99% and 99.5% isoprene by weight. In still other embodiments, the liquid isoprene composition comprises isoprene in an amount that is greater than about 99.5% by weight.

In other embodiments, the liquid isoprene composition further comprises carbon dioxide. In some embodiments, the carbon dioxide is present in an amount that is between about 0.01% by weight and about 1% by weight. In other embodiments, the carbon dioxide is present in an amount that is between about 0.05% and about 1% by weight. In further embodiments, the carbon dioxide is present in an amount that is between about 0.1% and about 1% by weight. In still further embodiments, the carbon dioxide is present in an amount that is between about 0.2% and about 0.7% by weight.

In other embodiments, the liquid isoprene composition further comprises nitrogen. In some embodiments, the nitrogen is present in an amount that is between about 0.001% by weight and about 1% by weight. In other embodiments, the carbon dioxide is present in an amount that is between about 0.01% and about 0.5% by weight. In further embodiments, the carbon dioxide is present in an amount that is between about 0.05% and about 0.5% by weight.

In other embodiments, the liquid isoprene composition further comprises ethanol. In some embodiments, the ethanol is present in an amount that is greater than about 0.01% by weight. In other embodiments, the ethanol is present in an amount that is greater than about 0.1%, 0.2%, 0.3%, 0.4%, 0.5%, 0.6%, 0.7%, 0.8%, and 0.9% by weight. In further embodiments, the ethanol is present in an amount that is greater than about 1% by weight.

In other embodiments, the liquid isoprene composition may comprise water in an amount that is less than about 1%, 0.5%, 0.1%, and 0.05% by weight. In other embodiments, the liquid isoprene composition may comprise water in an amount that is less than about 500 ppm, 250 ppm, 100 ppm, and 50 ppm by weight. In other embodiments, the liquid isoprene composition may comprise water in an amount, by weight, that is less than the level of detection.

In other embodiments, the microbial-derived liquid isoprene composition may comprise: isoprene in an amount of at least about 65% to an amount greater than about 99.5% by weight; carbon dioxide in an amount that is between about 0.01% and about 1% by weight; nitrogen in an amount that is between about 0.001% and about 1% by weight; ethanol in an amount greater than about 0.01% to an amount greater than about 1% by weight; water in an amount that is less than about 1% by weight to an amount that is less than the level of detection; $C_2$-$C_5$ alkynes in an amount 1 part per million or less; cyclopentadiene in an amount 1 part per million or less; piperylene in an amount 1 part per million or less; and 1,4-pentadiene in an amount 1 part per million or less.

In certain other embodiments, another liquid isoprene composition is provided. This composition comprises:
a. isoprene in an amount greater than about 65% by weight;
b. ethanol in an amount greater than about 0.01% by weight; and,
c. carbon dioxide in an amount between about 0.01% and about 1% by weight wherein the liquid isoprene composition comprises 1 part per million or less of $C_2$-$C_5$ alkynes, cyclopentadiene and piperylene $C_2$-$C_5$ alkynes. In some embodiments, the isoprene is present in an amount greater than about 85% by weight. In still other embodiments, the isoprene is present in an amount greater than about 90% by weight. In further embodiments, the isoprene is present in an amount greater than about 90% by weight and ethanol is present in an amount that is between about 0.01% and about 1% by weight.

For some of the above described liquid isoprene compositions, the compositions have a temperature below −35° C. and a pressure between 0.01 and about 2 atmospheres. In other embodiments, the compositions have a temperature between −45° C. and about −85° C. and a pressure below about 1 atmosphere. In still further embodiments, the compositions have a temperature below −45° C. and a pressure below about 0.5 atmosphere.

Microbial Host Cells

Any microbial host cells capable of making isoprene can be used in the methods herein which would result in the inventive isoprene compositions.

Illustrative examples of suitable host cells are microbes that have been shown to make isoprene naturally. These strains include those described by U.S. Pat. No. 5,849,970 and include: *Bacillus amyloliquiefaciens; Bacillus cereus; Bacillus subtillis* 6051; *Basillus substillis* 23059; *Bacillus subtillis* 23856; *Micrococcus luteus; Rhococcus rhodochrous; Acinetobacter calcoacetiucus; Agrobacternum rhizogenes; Escherichia coli; Erwinia herbicola; Pseudomonoas aeruginosa*; and *Psuedomonas citronellolis*. However, microbes that make isoprene naturally are produced at extremely low levels.

Isoprene is made from isopentenyl pyrophosphate (IPP) by isoprene synthase. Because all microbial host cells are capable of making IPP, any host cells can be made to make isoprene by the insertion of isoprene synthase into its genome. Illustrative examples of suitable nucleotide sequences include but are not limited to: (EF638224, *Populus alba*); (AJ294819, *Populus alba×Populus tremula*); (AM410988, *Populus nigra*); (AY341431, *Populus tremuloides*); (EF147555, *Populus trichocarpa*); and (AY316691, *Pueraria montana* var. *lobata*). The addition of a heterologous isoprene synthase to a microbial host cells that make isoprene naturally will improve isoprene yields of natural isoprene producers as well.

Any suitable microbial host cell can be genetically modified to make isoprene. A genetically modified host cell is one in which nucleic acid molecules have been inserted, deleted or modified (i.e., mutated; e.g., by insertion, deletion, substitution, and/or inversion of nucleotides), to produce isoprene. Illustrative examples of suitable host cells include any archae, bacterial, or eukaryotic cell. Examples of archae cells include, but are not limited to those belonging to the genera: *Aeropyrum, Archaeglobus, Halobacterium, Methanococcus, Methanobacterium, Pyrococcus, Sulfolobus,* and *Thermoplasma*. Illustrative examples of archae species include but are not limited to: *Aeropyrum pernix, Archaeoglobus fulgidus, Methanococcus jannaschii, Methanobacterium thermoautotrophicum, Pyrococcus abyssi, Pyrococcus horikoshii, Thermoplasma acidophilum, Thermoplasma volcanium.*

Examples of bacterial cells include, but are not limited to those belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus,* and *Zymomonas.*

Illustrative examples of bacterial species include but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei, Staphylococcus aureus,* and the like.

In general, if a bacterial host cell is used, a non-pathogenic strain is preferred. Illustrative examples of species with non-pathogenic strains include but are not limited to: *Bacillus subtilis, Escherichia coli, Lactibacillus acidophilus, Lactobacillus helveticus, Pseudomonas aeruginosa, Pseudomonas mevalonii, Pseudomonas pudita, Rhodobacter sphaeroides, Rodobacter capsulatus, Rhodospirillum rubrum,* and the like.

Examples of eukaryotic cells include but are not limited to fungal cells. Examples of fungal cells include, but are not limited to those belonging to the genera: *Aspergillus, Candida, Chrysosporium, Cryotococcus, Fusarium, Kluyveromyces, Neotyphodium, Neurospora, Penicillium, Pichia, Saccharomyces, Trichoderma* and *Xanthophyllomyces* (formerly *Phaffia*).

Illustrative examples of eukaryotic species include but are not limited to: *Aspergillus nidulans, Aspergillus niger, Aspergillus oryzae, Candida albicans, Chrysosporium lucknowense, Fusarium graminearum, Fusarium venenatum, Kluyveromyces lactis, Neurospora crassa, Pichia angusta, Pichia finlandica, Pichia kodamae, Pichia membranaefaciens, Pichia methanolica, Pichia opuntiae, Pichia pastoris, Pichia pijperi, Pichia quercuum, Pichia salictaria, Pichia thermotolerans, Pichia trehalophila, Pichia stipitis, Streptomyces ambofaciens, Streptomyces aureofaciens, Streptomyces aureus, Saccaromyces bayanus, Saccaromyces boulardi, Saccharomyces cerevisiae, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus, Trichoderma reesei* and *Xanthophyllomyces dendrorhous* (formerly *Phaffia rhodozyma*).

In general, if a eukaryotic cell is used, a non-pathogenic strain is preferred. Illustrative examples of species with non-pathogenic strains include but are not limited to: *Fusarium graminearum, Fusarium venenatum, Pichia pastoris, Saccaromyces boulardi,* and *Saccaromyces cerevisiae.*

In some embodiments, the host cells of the present invention have been designated by the Food and Drug Administration as GRAS or Generally Regarded As Safe. Illustrative examples of such strains include: *Bacillus subtilis, Lactibacillus acidophilus, Lactobacillus helveticus*, and *Saccharomyces cerevisiae*.

In addition to the heterologous nucleic acid encoding an isoprene synthase, the microbial host cell can be further modified to increase isoprene yields. These modifications include but are not limited to the expression of one or more heterologous nucleic acid molecules encoding one or more enzymes in the mevalonate or DXP pathways.

MEV Pathway

Figure 3:
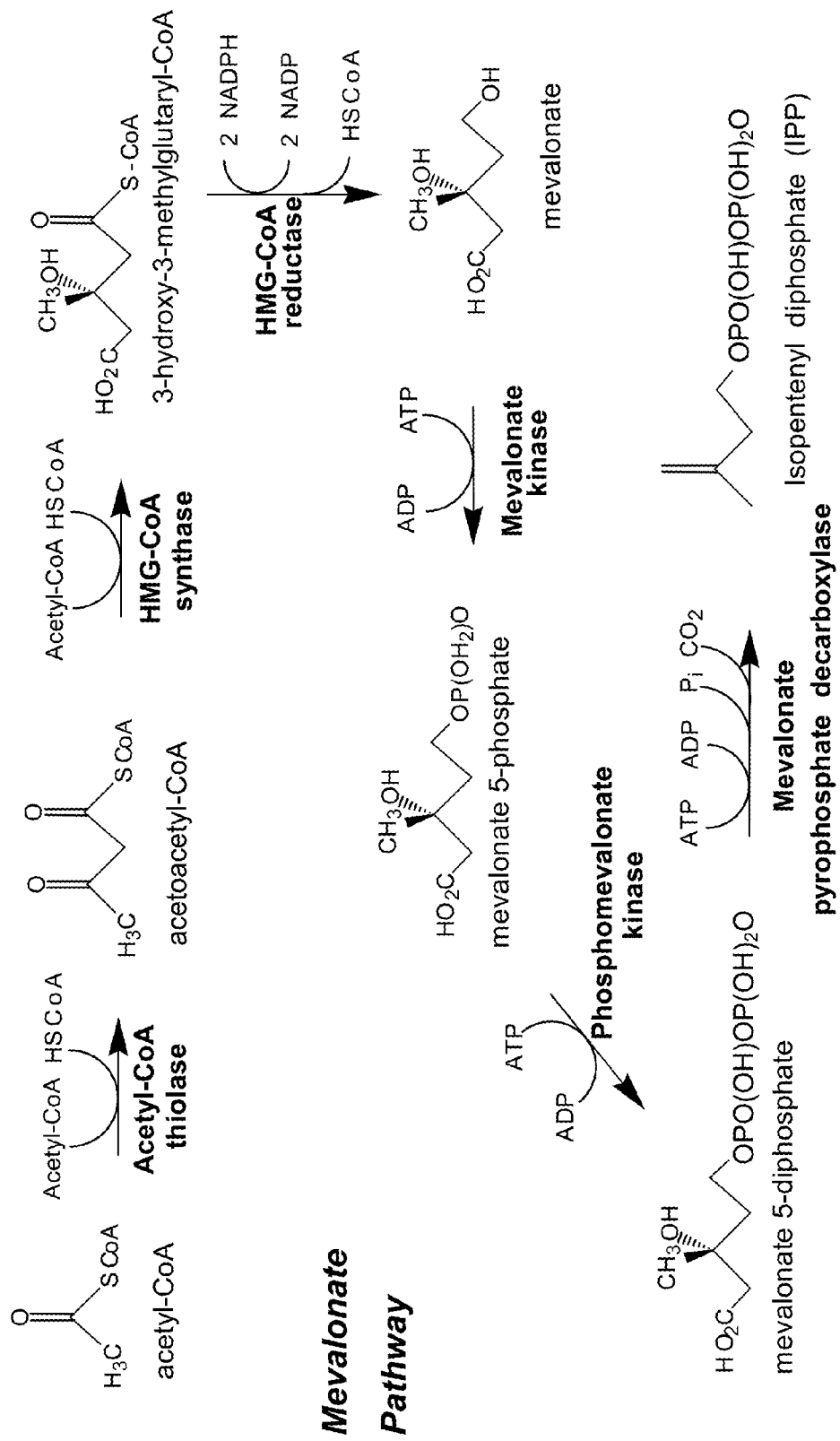
FIG. 3 is a schematic representation of the mevalonate ("MEV") pathway for the production of isopentenyl diphosphate ("IPP").

A schematic representation of the MEV pathway is described in FIG. 3. In general, the pathway comprises six steps.

In the first step, two molecules of acetyl-coenzyme A are enzymatically combined to form acetoacetyl-CoA. An enzyme known to catalyze this step is, for example, acetyl-CoA thiolase (also known as acetyl-CoA acetyltransferase). Illustrative examples of nucleotide sequences include but are not limited to the following GenBank accession numbers and the organism from which the sequences derived: (NC_000913 REGION: 2324131.2325315; *Escherichia coli*), (D49362; *Paracoccus denitrificans*), and (L20428; *Saccharomyces cerevisiae*).

In the second step of the MEV pathway, acetoacetyl-CoA is enzymatically condensed with another molecule of acetyl-CoA to form 3-hydroxy-3-methylglutaryl-CoA (HMG-CoA). An enzyme known to catalyze this step is, for example, HMG-CoA synthase. Illustrative examples of nucleotide sequences include but are not limited to: (NC_001145. complement 19061.20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

In the third step, HMG-CoA is enzymatically converted to mevalonate. An enzyme known to catalyze this step is, for example, HMG-CoA reductase. Illustrative examples of nucleotide sequences include but are not limited to: (NM_206548; *Drosophila melanogaster*), (NC_002758, Locus tag SAV2545, GeneID 1122570; *Staphylococcus aureus*), (NM_204485; *Gallus gallus*), (AB015627; *Streptomyces* sp. KO 3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734.118898; *Saccharomyces cerevisiae*).

In the fourth step, mevalonate is enzymatically phosphorylated to form mevalonate 5-phosphate. An enzyme known to catalyze this step is, for example, mevalonate kinase. Illustrative examples of nucleotide sequences include but are not limited to: (L77688; *Arabidopsis thaliana*), and (X55875; *Saccharomyces cerevisiae*).

In the fifth step, a second phosphate group is enzymatically added to mevalonate 5-phosphate to form mevalonate 5-pyrophosphate. An enzyme known to catalyze this step is, for example, phosphomevalonate kinase. Illustrative examples of nucleotide sequences include but are not limited to: (AF429385; *Hevea brasiliensis*), (NM_006556; *Homo sapiens*), and (NC_001145. complement 712315.713670; *Saccharomyces cerevisiae*).

In the sixth step, mevalonate 5-pyrophosphate is enzymatically converted into IPP. An enzyme known to catalyze this step is, for example, mevalonate pyrophosphate decarboxylase. Illustrative examples of nucleotide sequences include but are not limited to: (X97557; *Saccharomyces cerevisiae*), (AF290095; *Enterococcus faecium*), and (U49260; *Homo sapiens*).

DXP Pathway

Figure 4:
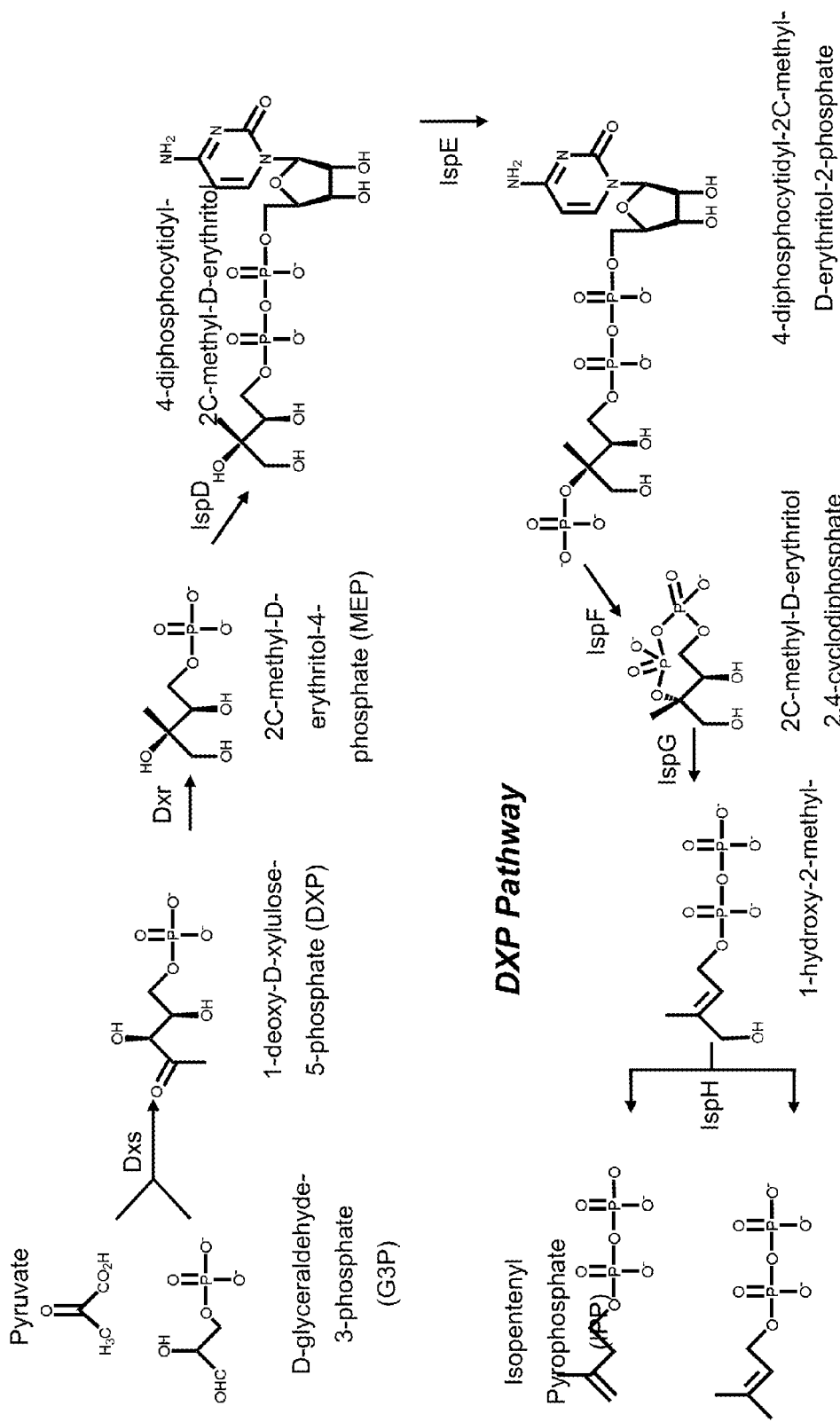
FIG. 4 is a schematic representation of the DXP pathway for the production of IPP and dimethylallyl pyrophosphate ("DMAPP"). Dxs is 1-deoxy-D-xylulose-5-phosphate synthase; Dxr is 1-deoxy-D-xylulose-5-phosphate reductoisomerase (also known as IspC); IspD is 4-diphosphocytidyl-2C-methyl-D-erythritol synthase; IspE is 4-diphosphocytidyl-2C-methyl-D-erythritolsynthase; IspF is 2C-methyl-D-erythritol 2,4-cyclodiphosphate synthase; IspG is 1-hydroxy-2-methyl-2-(E)-butenyl 4-diphosphate synthase (IspG); and ispH is isopentenyl/dimethylallyl diphosphate synthase.

A schematic representation of the DXP pathway is described in FIG. 4. In general, the DXP pathway comprises seven steps. In the first step, pyruvate is condensed with D-glyceraldehyde 3-phosphate to make 1-deoxy-D-xylulose-5-phosphate. An enzyme known to catalyze this step is, for example, 1-deoxy-D-xylulose-5-phosphate synthase. Illustrative examples of nucleotide sequences include but are not limited to: (AF035440; *Escherichia coli*), (NC_002947, locus tag PP0527; *Pseudomonas putida* KT2440), (CP000026, locus tag SPA2301; *Salmonella enterica Paratyphi*, see ATCC 9150), (NC_007493, locus tag RSP_0254; *Rhodobacter sphaeroides* 2.4.1), (NC_005296, locus tag RPA0952; *Rhodopseudomonas palustris* CGA009), (NC_004556, locus tag PD1293; *Xylella fastidiosa Temecula1*), and (NC_003076, locus tag AT5G11380; *Arabidopsis thaliana*).

In the second step, 1-deoxy-D-xylulose-5-phosphate is converted to 2C-methyl-D-erythritol-4-phosphate. An enzyme known to catalyze this step is, for example, 1-deoxy-D-xylulose-5-phosphate reductoisomerase. Illustrative examples of nucleotide sequences include but are not limited to: (AB013300; *Escherichia coli*), (AF148852; *Arabidopsis thaliana*), (NC_002947, locus tag PP1597; *Pseudomonas putida* KT2440), (AL939124, locus tag SCO5694; *Streptomyces coelicolor* A3(2)), (NC_007493, locus tag RSP_2709; *Rhodobacter sphaeroides* 2.4.1), and (NC_007492, locus tag Pfl_1107; *Pseudomonas fluorescens* PfO-1).

In the third step, 2C-methyl-D-erythritol-4-phosphate is converted to 4-diphosphocytidyl-2C-methyl-D-erythritol. An enzyme known to catalyze this step is, for example, 4-diphosphocytidyl-2C-methyl-D-erythritol synthase. Illustrative examples of nucleotide sequences include but are not limited to: (AF230736; *Escherichia coli*), (NC_007493, locus_tag RSP_2835; *Rhodobacter sphaeroides* 2.4.1), (NC_003071, locus_tag AT2G02500; *Arabidopsis thaliana*), and (NC_002947, locus_tag PP1614; *Pseudomonas putida* KT2440).

In the fourth step, 4-diphosphocytidyl-2C-methyl-D-erythritol is converted to 4-diphosphocytidyl-2C-methyl-D-erythritol-2-phosphate. An enzyme known to catalyze this step is, for example, 4-diphosphocytidyl-2C-methyl-D-erythritol kinase. Illustrative examples of nucleotide sequences include but are not limited to: (AF216300; *Escherichia coli*) and (NC_007493, locus_tag RSP_1779; *Rhodobacter sphaeroides* 2.4.1).

In the fifth step, 4-diphosphocytidyl-2C-methyl-D-erythritol-2-phosphate is converted to 2C-methyl-D-erythritol 2,4-cyclodiphosphate. An enzyme known to catalyze this step is, for example, 2C-methyl-D-erythritol 2,4-cyclodiphosphate synthase. Illustrative examples of nucleotide sequences include but are not limited to: (AF230738; *Escherichia coli*), (NC_007493, locus_tag RSP_6071; *Rhodobacter sphaeroides* 2.4.1), and (NC_002947, locus_tag PP1618; *Pseudomonas putida* KT2440).

In the sixth step, 2C-methyl-D-erythritol 2,4-cyclodiphosphate is converted to 1-hydroxy-2-methyl-2-(E)-butenyl-4-diphosphate. An enzyme known to catalyze this step is, for example, 1-hydroxy-2-methyl-2-(E)-butenyl-4-diphosphate synthase. Illustrative examples of nucleotide sequences include but are not limited to: (AY033515; *Escherichia coli*), (NC_002947, locus_tag PP0853; *Pseudomonas putida* KT2440), and (NC_007493, locus_tag RSP_2982; *Rhodobacter sphaeroides* 2.4.1).

In the seventh step, 1-hydroxy-2-methyl-2-(E)-butenyl-4-diphosphate is converted into either IPP or its isomer, DMAPP. An enzyme known to catalyze this step is, for example, isopentyl/dimethylallyl diphosphate synthase. Illustrative examples of nucleotide sequences include but are not limited to: (AY062212; *Escherichia coli*) and (NC_002947, locus_tag PP0606; *Pseudomonas putida* KT2440).

In some embodiments, "cross talk" (or interference) between the host cell's own metabolic processes and those processes involved with the production of IPP as provided by the present invention are minimized or eliminated entirely. For example, cross talk is minimized or eliminated entirely when the host microorganism relies exclusively on the DXP pathway for synthesizing IPP, and a MEV pathway is introduced to provide additional IPP. Such host organisms would not be equipped to alter the expression of the MEV pathway enzymes or process the intermediates associated with the MEV pathway. Organisms that rely exclusively or predominately on the DXP pathway include, for example, *Escherichia coli*.

In some embodiments, the host cell produces IPP via the MEV pathway, either exclusively or in combination with the DXP pathway. In other embodiments, a host's DXP pathway is functionally disabled so that the host cell produces IPP exclusively through a heterologously introduced MEV pathway. The DXP pathway can be functionally disabled by disabling gene expression or inactivating the function of one or more of the naturally occurring DXP pathway enzymes.

In other embodiments, the host cell produces IPP via the DXP pathway, either exclusively or in combination with the MEV pathway. In other embodiments, a host's MEV pathway is functionally disabled so that the host cell produces IPP exclusively through a heterologously introduced DXP pathway. The MEV pathway can be functionally disabled by disabling gene expression or inactivating the function of one or more of the naturally occurring MEV pathway enzymes.

Methods for genetically modifying host organisms and their cultivation have been previously described. Illustrative examples include U.S. Pat. Nos. 6,689,593; 7,172,886; 7,183,089; U.S. Patent Publication Nos. US 2008/0171378; US 2008/0274523; and US 2009/0203102 and PCT Publication Nos. WO 2007/139924; WO 2009/076676; WO 2010/003007; and WO 2009/132220, which are all incorporated herein by reference in their entirety. Additional methods for modifying host organisms to make isoprene are also provided in the Examples below.

Purification and Recovery of Microbially Derived Gaseous Isoprene

The present invention provides methods for handling a gaseous isoprene composition produced from the microbial host cells. When the resulting gaseous isoprene compositions or the above-described gaseous isoprene compositions are treated with the following methods, then the results are the liquid isoprene compositions described above.

In one aspect, a system for purifying isoprene without extractive distillation is provided. Extractive distillation is defined as distillation in the presence of a solvent that forms no azeotrope with other components in the mixture and is used to separate mixtures that cannot be separated by simple distillation because the volatility of at least two of the components in the mixture is nearly the same, causing them to evaporate at nearly the same temperature at a similar rate. Generally miscible, high boiling, and relatively non-volatile, the extraction distillation solvent interacts differently with the components in the mixture enabling the mixture to be separated by normal distillation. Extractive distillation is almost always used in purifying petroleum-derived isoprene. Because extractive distillation requires special equipment and is inherently energy intensive, it is substantial part of the costs associated with making isoprene. In many embodiments of the present invention, the resulting isoprene compositions do not include trace amounts of an extraction distillation solvent because extractive distillation solvents are not used. Illustrative examples of such solvents include but are not limited to acetonitrile and dimethylformamide.

FIG. 1 is a schematic representation of an exemplary separation system. Host cells are cultivated in a bioreactor and the isoprene produced by the cells vaporizes and forms a gaseous isoprene composition (1). Optionally, the gaseous isoprene composition may pass through a drying process to remove some of the water vapor (not shown). The gaseous isoprene composition (1) is directed to a first chiller 102 which cools the gaseous isoprene composition to a temperature between about 10° C. and about −15° C. The cooled gaseous isoprene composition (7) then passes through drum 104, where the water vapor in the gaseous isoprene composition condenses into a liquid and discharged from the process (5). The exiting gaseous isoprene composition (8) may pass through a drying process to remove any remaining water (not shown). The gaseous isoprene composition (8) is directed to a second chiller 106 further cooling the composition to a temperature below −35° C. The resulting liquid isoprene composition (9) flows to drum 108. Optionally, the bottom stream (10) from drum 108 may then be passed to nitrogen stripper 110 while the top stream (11) is recycled back to the first chiller 102 to assist in (or to serve as the refrigerant for) chilling the incoming gaseous isoprene (1) and then exiting a by-product stream (6). Substantially pure nitrogen (2) is introduced into nitrogen stripper 110 whereby the liquid isoprene composition (3) is recovered and the by-product nitrogen gas (4) can be discharged or recovered in a subsequent recovery step (not shown).

In another embodiment, the system comprises:
a. a bioreactor capable of culturing a plurality of host cells, preferably the bioreactor has a capacity of greater than 100 liters;
b. a first chiller and flash drum operably connected to the overhead stream of the bioreactor, the first chiller preferably capable of operating in a temperature range of between 10° C. and −15° C.;
c. a second chiller and flash drum operably connected to the overhead stream exiting from the first chiller and flash drum, the second chiller preferably capable of operating in a temperature below −35° C., for example between about −65° C. and about −85° C.;
d. optionally, the exiting overhead stream from the second chiller and flash drum may be operably connected to the inlet of the refrigerant or cooling stream of the first chiller; and
e. optionally, the condensed stream exiting from the second chiller and flash drum may be operably connected to a nitrogen stripper.

In another aspect, method for recovering isoprene using such a system is provided. The method comprises:
a. obtaining a first gaseous composition comprising isoprene and water wherein the gaseous composition comprises 1 part per million or less of $C_2$-$C_5$ alkynes;
b. flowing the first gaseous composition through a first chiller wherein the first chiller has a temperature of between about 10° C. and about −15° C. thereby resulting in a second gaseous composition and wherein the second gaseous composition comprises less water than the first gaseous composition, for example the second gas composition comprises about 3% by weight or less of water;

c. flowing the second gaseous composition through a second chiller wherein the second chiller has a temperature below −35° C.; and
d. collecting the resulting liquid isoprene composition.

In other embodiments, the method for recovering isoprene comprises reducing the water content present in the first gaseous composition by flowing the first gaseous composition through a first chiller wherein the first chiller has a temperature of between about 10° C. and about −15° C. thereby resulting in a second gaseous composition and wherein the second gaseous composition comprises less water than the first gaseous composition, for example the second gas composition comprises less than about 3% by weight of water. In other embodiments, the second gas composition comprises less than about 2% by weight of water, less than 1%, 0.5%, 0.1%, and 0.05% by weight. In other embodiments, the second gas composition comprises less than about 500 ppm by weight of water, less than 250 ppm, 100 ppm and 50 ppm by weight.

In another aspect, method for recovering isoprene using such a system is provided. The method comprises:
a. obtaining a first gaseous composition comprising isoprene and water wherein the gaseous composition comprises 1 part per million or less of $C_2$-$C_5$ alkynes;
b. flowing the first gaseous composition through a first chiller wherein the first chiller has a temperature of between about 10° C. and about −15° C. thereby resulting in a second gaseous composition and wherein the second gaseous composition comprises less water than the first gaseous composition, for example the second gas composition comprises about 3% by weight or less of water;
c. flowing the second gaseous composition through a second chiller wherein the second chiller has a temperature below −35° C. thereby resulting in a liquid isoprene composition, wherein the liquid isoprene composition comprises less of one or more of the following components than the second gaseous composition, comprising:
  i. water in amount less than about 1% by weight or less;
  ii. carbon dioxide in amount less than 1% by weight;
  iii. nitrogen in amount less than 1% by weight; and
d. collecting the resulting liquid isoprene composition.

In some embodiments, the method further comprises nitrogen stripping the liquid isoprene composition. This nitrogen stripping may be accomplished by any suitable method including passing a substantially pure nitrogen stream through the liquid isoprene enriched composition. This nitrogen stream serves to further remove dissolved gases (such, as for example oxygen, carbon dioxide, nitrogen, and argon) and or/remaining water. In other embodiments, nitrogen stripping of the liquid isoprene composition may comprise removing: dissolved oxygen to levels less than about 1%, 0.5%, 0.1%, and 0.05% by weight; dissolved carbon dioxide to levels less than about 1%, 0.5%, 0.1%, and 0.05% by weight; dissolved nitrogen to levels less than about 1%, 0.5%, 0.1%, and 0.05% by weight; dissolved argon to levels less than about 1%, 0.5%, 0.1%, and 0.05% by weight; and any remaining water to levels less than about 1%, 0.5%, 0.1%, 0.05% by weight to levels lower than the level of detection.

In some embodiments, the method further comprises extracting hydrocarbon impurities at some point in the purifying isoprene process. This hydrocarbon extraction may be accomplished by passing a portion or all of the first gaseous composition, second gaseous composition and/or the liquid isoprene composition over or through a modified zeolite membrane and/or molecular seive. The zeolite membrane and/or molecular sieves may be modified to selectively adsorb either isoprene and not the other hydrocarbons present in the treated composition or vice versa (adsorb other hydrocarbons in the treated composition and not isoprene). In some embodiments, the zeolites and/or molecular sieves are modified by carbonization to provide the selected adsorbtivity. In some embodiments, the zeolites may be L-type, Y-type, ZSM-5, and/or beta-type. In some embodiments a method for enhancing the selectivity of a zeolite by controlled carbonization as detailed in U.S. Pat. No. 7,041,616, which is hereby incorporated in its entirety by reference, may be used.

In other embodiments, the first gaseous composition further comprises carbon dioxide. In still other embodiments, the first gaseous composition further comprises oxygen. In still other embodiments, the first gaseous composition further comprises nitrogen.

In other embodiments, the first gaseous composition comprises 1 part per million or less of $C_2$-$C_5$ alkynes and cyclopentadiene, In further embodiments, the first gaseous composition further comprises 1 part per million or less of $C_2$-$C_5$ alkynes and piperylene. In still other embodiments, the first gaseous composition comprises 1 part per million or less of $C_2$-$C_5$ alkynes and 1,4-pentadiene. In still other embodiments, the first gaseous composition comprises 1 part per million or less of $C_2$-$C_5$ alkynes, cyclopentadiene, piperylene, and 1,4-pentadiene.

In other embodiments, the first gaseous composition is flowed through a drier prior to flowing through the first chiller. In still other embodiments, the first gaseous composition is flowed through a drier after flowing through the first chiller but prior to flowing through the second chiller.

In other embodiments, the first chiller has a temperature of about −5° C. In other embodiments, the first chiller is cooled using a propylene refrigeration system. In still other embodiments, the first chiller is cooled using an ammonium refrigeration system.

In other embodiments, the second chiller has a temperature less than about −50° C. In other embodiments, the second chiller has a temperature of about −60° C. to about −85° C. In still other embodiments, the second chiller has a temperature of less than about −65° C. In still other embodiments, the second chiller has a temperature between about −35° C. and about −85° C.

In other embodiments, the liquid isoprene composition comprises at least about 70%, 75%, 80%, 85%, and 90% isoprene by weight. In other embodiments, the liquid isoprene comprises at least about 95%, 96%, 97%, 98%, 99% and 99.5% isoprene by weight. In still other embodiments, the liquid isoprene composition comprises isoprene in an amount that is greater than about 99.5% by weight.

In other embodiments, the second chiller is cooled using an ethylene refrigeration system.

In another aspect, another method is provided. The method comprises:
a. culturing a plurality of host cells capable of making isoprene;
b. forming a first gaseous composition comprising isoprene and water wherein the water is present in an amount greater than about 70% of its saturation amount;
c. subjecting the first gaseous composition to a first cooling step whereby substantially all of the water is removed from the first gaseous composition resulting a second gaseous composition;
d. subjecting the second gaseous composition to a second cooling step whereby a liquid isoprene composition is collected.

In some embodiments, the method further comprises nitrogen stripping the liquid isoprene composition.

In other embodiments, the first gaseous composition further comprises carbon dioxide. In still other embodiments, the first gaseous composition further comprises oxygen. In still other embodiments, the first gaseous composition further comprises nitrogen.

In other embodiments, the first gaseous composition comprises 1 part per million or less of $C_2$-$C_5$ alkynes and cyclopentadiene. In further embodiments, the first gaseous composition further comprises 1 part per million or less of $C_2$-$C_5$ alkynes and piperylene. In still other embodiments, the first gaseous composition comprises 1 part per million or less of $C_2$-$C_5$ alkynes and 1,4-pentadiene. In still other embodiments, the first gaseous composition comprises 1 part per million or less of $C_2$-$C_5$ alkynes, cyclopentadiene, piperylene, and 1,4-pentadiene.

In other embodiments, the first gaseous composition is subjected through a drier prior to the first cooling step. In still other embodiments, the first gaseous composition is subjected through a drier after the first cooling step but prior to the second cooling step.

In other embodiments, the first cooling step cools the first gaseous isoprene composition to a temperature between about 10° C. and about −15° C., between about 10° C. and about −10° C., about 5° C. and about −5° C., and about 5° C. and about −10° C.

In other embodiments, the first cooling step uses a propylene refrigeration system. In still other embodiments, the first cooling step uses chiller an ammonium refrigeration system.

In other embodiments, the second cooling step cools the second gaseous isoprene composition to a temperature less than −35° C. In other embodiments, the second cooling step cools the second gaseous isoprene composition to a temperature less than about −50° C. In still other embodiments, the second cooling step cools the second gaseous isoprene composition to a temperature about −60° C. to about −85° C. In still further embodiments, the second cooling step cools the second gaseous isoprene composition to a temperature of less than about −65° C.

In other embodiments, the second cooling step uses an ethylene refrigeration system.

In other embodiments, the liquid isoprene composition comprises at least about 70%, 75%, 80%, 85%, and 90% isoprene by weight. In other embodiments, the liquid isoprene comprises at least about 95%, 96%, 97%, 98%, 99% and 99.5% isoprene by weight. In still other embodiments, the liquid isoprene composition comprises isoprene in an amount that is greater than about 99.5% by weight.

In other embodiments, the host cells are selected from the genus *Bacillus, Escherichia* or *Acinetobacter*. In still other embodiments, the host cells are *Escherichia coli*. In further embodiments, the host cells are yeast. In still further embodiments, the host cells are *Saccharomyces cerevisiae*.

In another aspect, another method is provided. The method comprises:
a. contacting a plurality of host cells capable of making isoprene in an aqueous medium wherein the aqueous medium is in contact with an immiscible organic liquid and the aqueous medium, the host cells, and the immiscible organic liquid is in a closed vessel; and
b. culturing the host cells in the aqueous medium whereby the host cells make isoprene and the isoprene is captured in the immiscible organic liquid.

In some embodiments, the method further comprises separating the immiscible organic liquid from the aqueous medium and separating the isoprene from the immiscible organic liquid.

In other embodiments, the immiscible organic liquid is selected from butyl acetate, ethyl acetate, isopropyl myristate, methyl isobutyl ketone, methyl oleate, and toluene. In certain embodiments, the solvent is butyl acetate. In other embodiments, the immiscible organic liquid is isopropyl myristate.

In other embodiments, the isoprene is separated from the immiscible organic liquid by heating the immiscible organic liquid to a temperature above 34° C.

The resulting gaseous isoprene composition can then be further purified using the methods described above.

Figure 2:
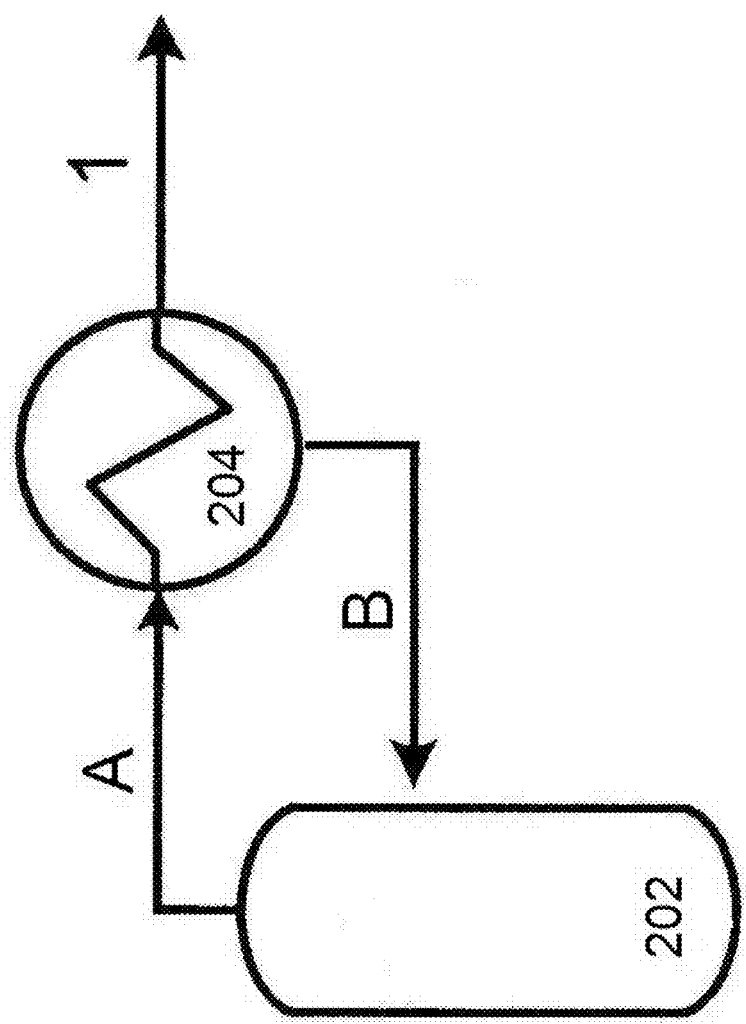
FIG. 2 is another schematic representation of another exemplary separation system.

In another aspect, a system for making microbial isoprene is provided. An illustrative example of such a system is shown in FIG. 2. Bioreactor 202 is a closed system where host cells capable of making isoprene are cultivated in an aqueous medium and with an immiscible organic liquid on top of the aqueous medium. Because bioreactor 202 is a closed system, the isoprene produced by the host cells is captured by the immiscible organic liquid. The isoprene-enriched immiscible organic liquid (A) may then directed be directed to any suitable gas-liquid separation method. In this example, the isoprene-enriched immiscible organic liquid is directed to a heater 204 which volatizes the isoprene into a gaseous isoprene composition (1). This gaseous isoprene composition (1) can then be further purified using the systems and methods described above. The immiscible organic liquid (B) can optionally be recycled and used in subsequent bioreactions to make isoprene.

In another embodiment, the system comprises:
a. a closed vessel;
b. an aqueous medium, within the vessel, forming a first phase;
c. a plurality of host cells, within the aqueous medium, capable of making isoprene; and,
d. a liquid organic second phase, capable of capturing the isoprene made by the host cells, in contact with the first phase.

In some embodiments, the immiscible organic liquid is selected from butyl acetate, ethyl acetate, isopropyl myristate, methyl isobutyl ketone, methyl oleate, and toluene. In certain embodiments, the solvent is butyl acetate. In other embodiments, the immiscible organic liquid is isopropyl myristate.

In other embodiments, the host cells are selected from the genus *Bacillus, Escherichia* or *Acinetobacter*. In still other embodiments, the host cells are *Escherichia coli*. In further embodiments, the host cells are yeast. In still further embodiments, the host cells are *Saccharomyces cerevisiae*.

EXAMPLES

The practice of the present invention can employ, unless otherwise indicated, conventional techniques of the biosynthetic industry and the like, which are within the skill of the art. To the extent such techniques are not described fully herein, one can find ample reference to them in the scientific literature.

In the following examples, efforts have been made to ensure accuracy with respect to numbers used (for example, amounts, temperature, and so on), but variation and deviation can be accommodated, and in the event a clerical error in the numbers reported herein exists, one of ordinary skill in the arts to which this invention pertains can deduce the correct amount in view of the remaining disclosure herein. Unless indicated otherwise, temperature is reported in degrees Celsius, and pressure is at or near atmospheric pressure at sea level. All reagents, unless otherwise indicated, were obtained commercially. The following examples are intended for illustrative purposes only and do not limit in any way the scope of the present invention.

Example 1

This example describes methods for detecting isoprene trapped in an immiscible organic liquid in a closed fermentation system.

In this example, isopropyl myristate (IPM) and solutions of IPM spiked with 103 mg/L, 10.3 mg/L and 0 mg/L isoprene were prepared and stored in 100 ml capped media bottles.

125 ml unbaffled flasks with screw caps/septa were set up in triplicate. The flasks contained 40 ml medium (Yeast Nitrogen Base media with 4% galactose, 0.2% glucose, Leu) inoculated with overnight yeast culture (which does not make isoprene) grown to an OD=0.05 with 8 ml of IPM solutions with the various concentrations of isoprene. The sealed flasks were incubated for 72 hours at 30° C. and 200 rpm.

Post-incubation, the IPM overlay was phase-separated by manual transfer to primary GC vials, then transferred to secondary GC vials and run undiluted on GC-FID. In addition to samples from flasks, the original solutions of 103 and 10.3 mg/L isoprene in IPM (NOT shaken for 72 hours at 200 rpm, 30° C.) were also analyzed.

Figure 5:
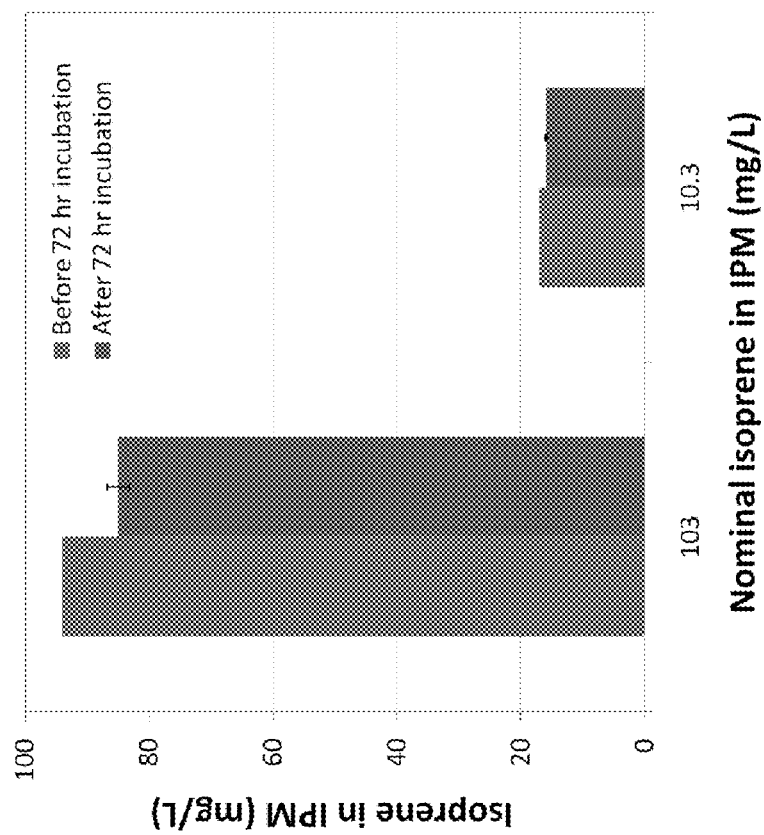
FIG. 5 shows the recovery of isoprene from an immiscible organic liquid (isopropyl myristate) from a closed fermentation system.

As shown by FIG. 5, over 90% of the spiked isoprene was recovered from the IPM layer. Cell growth for cultures with 103, 10.3, and 0 mg/L isoprene in the IPM layer was indistinguishable.

Example 2

This example describes methods for making nucleic acids for expressing in *Saccharomyces cerevisiae* heterologous isoprene synthases.

Genomic DNA was isolated from *Saccharomyces cerevisiae* strains Y002 (CEN.PK2 background MATA ura3-52 trp1-289 leu2-3,112 his3Δ1 MAL2-8C SUC2) (van Dijken et al. (2000) Enzyme and Microbial Technology 26:706-714), Y007 (S288C background MATA trp1Δ63) (ATCC number 200873), Y051 (S288C background), and EG123 (ATCC number 204278). The strains were grown overnight in liquid medium containing 1% Yeast extract, 2% Bacto-peptone, and 2% Dextrose (YPD medium). Cells were isolated from 10 mL liquid cultures by centrifugation at 3,100 rpm, washing of cell pellets in 10 mL ultra-pure water, and re-centrifugation. Genomic DNA was extracted using the Y-DER yeast DNA extraction kit (Pierce Biotechnologies, Rockford, Ill.) as per manufacturer's suggested protocol. Extracted genomic DNA was re-suspended in 100 uL 10 mM Tris-Cl, pH 8.5, and $OD_{260/280}$ readings were taken on a ND-1000 spectrophotometer (NanoDrop Technologies, Wilmington, Del.) to determine genomic DNA concentration and purity.

DNA amplification by Polymerase Chain Reaction (PCR) was done in an Applied Biosystems 2720 Thermocycler (Applied Biosystems Inc, Foster City, Calif.) using the Phusion High Fidelity DNA Polymerase system (Finnzymes OY, Espoo, Finland) as per manufacturer's suggested protocol. Upon the completion of a PCR amplification of a DNA fragment that was to be inserted into the pCR®4Blunt-TOPO vector (Invitrogen, Carlsbad, Calif.), A nucleotide overhangs were created by adding 1 uL of Qiagen Taq Polymerase (Qiagen, Valencia, Calif.) to the reaction mixture and performing an additional 10 minute, 72° C. PCR extension step, followed by cooling to 4° C. Upon completion of a PCR amplification, 8 uL of a 50% glycerol solution was added to the reaction mix.

Agarose gel electrophoresis was performed using a 1% TBE (0.89 M Tris, 0.89 M Boric acid, 0.02 M EDTA sodium salt) agarose gel containing 0.5 μg/mL ethidium bromide, at 120 V, 400 mA for 30 minutes. DNA bands were visualized using ultraviolet light. DNA bands were excised from the gel with a sterile razor blade, and the excised DNA was gel purified using the Zymoclean Gel DNA Recovery Kit (Zymo Research, Orange, Calif.) according to manufacturer's suggested protocols. The purified DNA was eluted into 10 uL ultra-pure water, and $OD_{260/280}$ readings were taken on a ND-1000 spectrophotometer to determine DNA concentration and purity.

Ligations were performed using 100-500 μg of purified PCR product and High Concentration T4 DNA Ligase (New England Biolabs, Ipswich, Mass.) as per manufacturer's suggested protocol. For plasmid propagation, ligated constructs were transformed into *Escherichia coli* DH5α chemically competent cells (Invitrogen, Carlsbad, Calif.) as per manufacturer's suggested protocol. Positive transformants were selected on solid media containing 1.5% Bacto Agar, 1% Tryptone, 0.5% Yeast Extract, 1% NaCl, and an appropriate antibiotic. Isolated transformants were grown for 16 hours in liquid LB medium containing 50 μg/mL carbenicillin or kanamycin antibiotic at 37° C., and plasmid was isolated and purified using a QIAprep Spin Miniprep kit (Qiagen, Valencia, Calif.) as per manufacturer's suggested protocol. Constructs were verified by performing diagnostic restriction enzyme digestions, resolving DNA fragments on an agarose gel, and visualizing the bands using ultraviolet light. Select constructs were also verified by DNA sequencing, which was done by Elim Biopharmaceuticals Inc. (Hayward, Calif.).

Expression plasmid pAM353 was generated by inserting a nucleotide sequence encoding a β-farnesene synthase into the pRS425-Gal1 vector (Mumberg et. al. (1994) *Nucl. Acids. Res.* 22(25): 5767-5768). The nucleotide sequence insert was generated synthetically, using as a template the coding sequence of the β-farnesene synthase gene of *Artemisia annua* (GenBank accession number AY835398) codon-optimized for expression in *Saccharomyces cerevisiae* (SEQ ID NO: 1). The synthetically generated nucleotide sequence was flanked by 5' BamHI and 3' XhoI restriction sites, and could thus be cloned into compatible restriction sites of a cloning vector such as a standard pUC or pACYC origin vector. The synthetically generated nucleotide sequence was isolated by digesting to completion the construct using BamHI and XhoI restriction endonucleases. The reaction mixture was resolved by gel electrophoresis, the approximately 1.7 kb DNA fragment comprising the β-farnesene synthase coding sequence was gel purified, and the isolated DNA fragment was ligated into the BamHI XhoI restriction site of the pRS425-Gal1 vector, yielding expression plasmid pAM353.

Expression plasmid pAM404 was generated by inserting a nucleotide sequence encoding the β-farnesene synthase of *Artemisia annua* (GenBank accession number AY835398) codon-optimized for expression in *Saccharomyces cerevisiae* into vector pAM178 (SEQ ID NO: 2). The nucleotide sequence encoding the β-farnesene synthase was PCR amplified from pAM353 using primers 52-84 pAM326 BamHI (SEQ ID NO: 21) and 52-84 pAM326 NheI (SEQ ID NO: 22). The resulting PCR product was digested to completion using BamHI and NheI restriction endonucleases, the reaction mixture was resolved by gel electrophoresis, the approximately 1.7 kb DNA fragment comprising the β-farnesene synthase coding sequence was gel purified, and the isolated DNA fragment was ligated into the BamHI NheI restriction site of vector pAM178, yielding expression plasmid pAM404.

Plasmid Genetrix2080 was generated by inserting a nucleotide sequence encoding an isoprene synthase into vector pUC19. The insert was generated synthetically as two approximately equal sized DNA fragments, fragment 2080_1 (SEQ ID NO: 3) and fragment 2080_2 (SEQ ID NO: 4), using as a template the coding sequence of the isoprene synthase gene of Kudzu codon-optimized for expression in Saccharomyces cerevisiae. Each DNA fragment was flanked by LguI restriction sites, and comprised a 40 base pair overlapping sequence at one end. The synthetically generated DNA fragments were blunt ligated into the SmaI restriction site of the pUC19 cloning vector, from which the two inserts were excised again by digesting to completion 500 μg of the construct using LguI restriction endonuclease (Fermentas, Glen Burnie, Md.). The restriction endonuclease was heat inactivated for 20 minutes at 65° C., and the DNA fragments were stitched together by a first round of PCR amplification (one cycle of denature at 98° C. for 2 minutes; 5 cycles of denature at 98° C. for 30 seconds and anneal/extend at 72° C. for 30 seconds per kilobase PCR product; no primers were used). Samples were placed on ice, 0.5 uM of each terminal primer TRIX_L_494 (SEQ ID NO: 79) and TRIX_L_495 (SEQ ID NO: 80) were added to the reaction mixture, and a second round of PCR amplification was performed (one cycle of denature at 98° C. for 2 minutes; 35 rounds of denature at 98° C. for 12 seconds and anneal/extend at 72° C. for 20 seconds per kilobase PCR product; one cycle of final extend at 72° C. for 7 minutes; and a final hold at 4° C.). The reaction mixture was resolved by gel electrophoresis, the assembled DNA fragment was gel purified, treated with T4 polynucleotide kinase (PNK) (New England Biolabs, Ipswich, Mass.), and blunt ligated into the SmaI restriction site of vector pUC19, yielding plasmid Genetrix2080.

Plasmid Genetrix2081 was generated by inserting a nucleotide sequence encoding an isoprene synthase into vector pUC19. The insert was generated synthetically as two approximately equal sized DNA fragments, fragment 2081_1 (SEQ ID NO: 5) and fragment 2081_2 (SEQ ID NO: 6), using as a template the coding sequence of the isoprene synthase gene of *Populus nigra* codon-optimized for expression in *Saccharomyces cerevisiae*. Each DNA fragment was flanked by LguI restriction sites, and comprised a 30 base pair overlapping sequence at one end. The synthetically generated DNA fragments were blunt ligated into the SmaI restriction site of the pUC19 cloning vector, from which the two inserts were excised again by digesting to completion 500 μg of the construct using LguI restriction endonuclease (Fermentas, Glen Burnie, Md.). The restriction endonuclease was heat inactivated for 20 minutes at 65° C., and the DNA fragments were stitched together by a first round of PCR amplification (one cycle of denature at 98° C. for 2 minutes; 5 cycles of denature at 98° C. for 30 seconds and anneal/extend at 72° C. for 30 seconds per kilobase PCR product; no primers were used). Samples were placed on ice, 0.5 uM of each terminal primer TRIX_L_497 (SEQ ID NO: 81) and TRIX_L_498 (SEQ ID NO: 82) were added to the reaction mixture, and a second round of PCR amplification was performed (one cycle of denature at 98° C. for 2 minutes; 35 rounds of denature at 98° C. for 12 seconds and anneal/extend at 72° C. for 20 seconds per kilobase PCR product; one cycle of final extend at 72° C. for 7 minutes; and a final hold at 4° C.). The reaction mixture was resolved by gel electrophoresis, the assembled DNA fragment was gel purified, treated with T4 polynucleotide kinase (PNK) (New England Biolabs, Ipswich, Mass.), and blunt ligated into the SmaI restriction site of vector pUC19, yielding plasmid Genetrix2081.

Plasmid Genetrix2082 was generated by inserting a nucleotide sequence encoding an isoprene synthase into vector pUC19. The insert was generated synthetically as two approximately equal sized DNA fragments, fragment 2082_1 (SEQ ID NO: 7) and fragment 2082_2 (SEQ ID NO: 8), using as a template the coding sequence of the isoprene synthase gene of *Populus alba×Populus tremula* codon-optimized for expression in *Saccharomyces cerevisiae*. Each DNA fragment was flanked by LguI restriction sites, and comprised a 40 base pair overlapping sequence at one end. The synthetically generated DNA fragments were blunt ligated into the SmaI restriction site of the pUC19 cloning vector, from which the two inserts were excised again by digesting to completion 500 μg of the construct using LguI restriction endonuclease (Fermentas, Glen Burnie, Md.). The restriction endonuclease was heat inactivated for 20 minutes at 65° C., and the DNA fragments were stitched together by a first round of PCR amplification (one cycle of denature at 98° C. for 2 minutes; 5 cycles of denature at 98° C. for 30 seconds and anneal/extend at 72° C. for 30 seconds per kilobase PCR product; no primers were used). Samples were placed on ice, 0.5 uM of each terminal primer TRIX_L_500 (SEQ ID NO: 83) and TRIX_L_501 (SEQ ID NO: 84) were added to the reaction mixture, and a second round of PCR amplification was performed (one cycle of denature at 98° C. for 2 minutes; 35 rounds of denature at 98° C. for 12 seconds and anneal/extend at 72° C. for 20 seconds per kilobase PCR product; one cycle of final extend at 72° C. for 7 minutes; and a final hold at 4° C.). The reaction mixture was resolved by gel electrophoresis, the assembled DNA fragment was gel purified, treated with T4 polynucleotide kinase (PNK) (New England Biolabs, Ipswich, Mass.), and blunt ligated into the SmaI restriction site of vector pUC19, yielding plasmid Genetrix2082.

Figure 6:
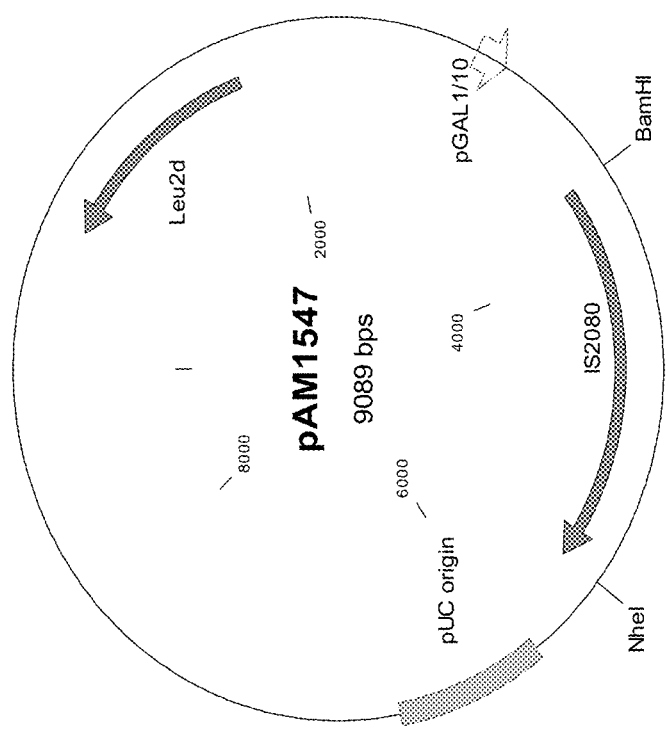
FIG. 6 shows a map of plasmid pAM1547.

Expression plasmid pAM1547 was generated by replacing the β-farnesene synthase coding sequence of expression plasmid pAM404 with the isoprene synthase coding sequence of plasmid Genetrix2080. DNA fragment IS2080 was generated by PCR amplifying plasmid Genetrix2080 using primers YD-198-70A (SEQ ID NO: 85) and YD-198-70B (SEQ ID NO: 86), digesting the PCR product to completion using restriction endonucleases BamHI and NheI, resolving the reaction mixture by gel electrophoresis, and gel purifying the approximately 1.8 kb DNA fragment comprising the isoprene synthase coding sequence. Expression plasmid pAM404 was digested to completion using restriction endonucleases BamHI and NheI, the reaction mixture was resolved by gel electrophoresis, the approximately 7.3 kb vector backbone (lacking the β-farnesene synthase coding sequence) was gel purified, and the purified vector backbone was ligated with DNA fragment IS2080, yielding pAM1547 (see FIG. 6 for a plasmid map).

Expression plasmid pAM1548 was generated by replacing the β-farnesene synthase coding sequence of expression plasmid pAM404 with a truncated version of the isoprene synthase coding sequence of plasmid Genetrix2080. DNA fragment IS2080T was generated by PCR amplifying plasmid Genetrix2080 using primers YD-198-70B (SEQ ID NO: 86) and YD-198-70G (SEQ ID NO: 91), digesting the PCR product to completion using restriction endonucleases BamHI and NheI, resolving the reaction mixture by gel electrophoresis, and gel purifying the approximately 1.65 kb DNA fragment comprising the truncated isoprene synthase coding sequence. pAM404 was digested to completion using restriction endonucleases BamHI and NheI, the reaction mixture was resolved by gel electrophoresis, the approximately 7.3 kb backbone (lacking the β-farnesene synthase coding sequence) was gel purified, and the purified vector backbone was ligated with the amplified DNA fragment IS2080T, yielding pAM1548.

Expression plasmid pAM1549 was generated by replacing the β-farnesene synthase coding sequence of expression plasmid pAM404 with the isoprene synthase coding sequence of plasmid Genetrix2081. DNA fragment IS2081 was generated by PCR amplifying plasmid Genetrix2081 using primers YD-198-70C (SEQ ID NO: 87) and YD-198-70D (SEQ ID NO: 88), digesting the PCR product to completion using restriction endonucleases BamHI and NheI, resolving the reaction mixture by gel electrophoresis, and gel purifying the approximately 1.8 kb DNA fragment comprising the isoprene synthase coding sequence. Expression plasmid pAM404 was digested to completion using restriction endonucleases BamHI and NheI, the reaction mixture was resolved by gel electrophoresis, the approximately 7.3 kb vector backbone (lacking the β-farnesene synthase coding sequence) was gel purified, and the purified vector backbone was ligated with DNA fragment IS2081, yielding pAM1549.

Expression plasmid pAM1550 was generated by replacing the β-farnesene synthase coding sequence of expression plasmid pAM404 with a truncated version of the isoprene synthase coding sequence of plasmid Genetrix2081. DNA fragment IS2081T was generated by PCR amplifying plasmid Genetrix2081 using primers YD-198-70D (SEQ ID NO: 88) and YD-198-70H (SEQ ID NO: 92), digesting the PCR product to completion using restriction endonucleases BamHI and NheI, resolving the reaction mixture by gel electrophoresis, and gel purifying the approximately 1.6 kb DNA fragment comprising the truncated isoprene synthase coding sequence. Expression plasmid pAM404 was digested to completion using restriction endonucleases BamHI and NheI, the reaction mixture was resolved by gel electrophoresis, the approximately 7.3 kb vector backbone (lacking the O-farnesene synthase coding sequence) was gel purified, and the purified vector backbone was ligated with DNA fragment IS2081T, yielding pAM1550.

Expression plasmid pAM1551 was generated by replacing the β-farnesene synthase coding sequence of expression plasmid pAM404 with the isoprene synthase coding sequence of plasmid Genetrix2082. DNA fragment IS2082 was generated by PCR amplifying plasmid Genetrix2082 using primers YD-198-70E (SEQ ID NO: 89) and YD-198-70F (SEQ ID NO: 90), digesting the PCR product to completion using restriction endonucleases BamHI and NheI, resolving the reaction mixture by gel electrophoresis, and gel purifying the approximately 1.8 kb DNA fragment comprising the isoprene synthase coding sequence. Expression plasmid pAM404 was digested to completion using restriction endonucleases BamHI and NheI, the reaction mixture was resolved by gel electrophoresis, the approximately 7.3 kb vector backbone (lacking the β-farnesene synthase coding sequence) was gel purified, and the purified vector backbone was ligated with DNA fragment IS2082, yielding pAM1551.

Expression plasmid pAM1552 was generated by replacing the β-farnesene synthase coding sequence of expression plasmid pAM404 with a truncated version of the isoprene synthase coding sequence of plasmid Genetrix2082. DNA fragment IS2082T was generated by PCR amplifying plasmid Genetrix2082 using primers YD-198-70F (SEQ ID NO: 90) and YD-198-70I (SEQ ID NO: 93), digesting the PCR product to completion using restriction endonucleases BamHI and NheI, resolving the reaction mixture by gel electrophoresis, and gel purifying the approximately 1.64 kb DNA fragment comprising the truncated isoprene synthase coding sequence. Expression plasmid pAM404 was digested to completion using restriction endonucleases BamHI and NheI, the reaction mixture was resolved by gel electrophoresis, the approximately 7.3 kb vector backbone (lacking the β-farnesene synthase coding sequence) was gel purified, and the purified vector backbone was ligated with DNA fragment IS2082T, yielding pAM1552.

Plasmid pAM840 was generated by inserting the coding sequence of the hisG gene into the pCR®2.1-TOPO vector (Invitrogen, Carlsbad, Calif.). The coding sequence of the hisG gene was PCR amplified using primers KB34 (SEQ ID NO: 75) and KB39 (SEQ ID NO: 76) and plasmid pNKY51 (Alani et al. (1987) Genetics 116(4):541-555) as template. The amplified DNA fragment was ligated with the Topo vector as per manufacturer's suggested protocol, yielding pAM840.

Plasmid pAM728 was generated by introducing the coding sequence of the farnesene synthase gene of *Artemisia annua* (GenBank accession number AY835398) codon-optimized for expression in *Saccharomyces cerevisiae* and under control of the promoter of the GALT gene of *Sacharomyces cerevisiae* ($P_{GAL7}$) into plasmid pRS425 (Christianson et al. (1992) Gene 110(1):119-122). An approximately 0.5 kb DNA fragment comprising $P_{GAL7}$ was PCR amplified from Y002 genomic DNA using primers GW-110-26-pGAL7-PstI F (SEQ ID NO: 119) and GW-110-26-pGAL7 R (SEQ ID NO: 120) and was gel purified. An approximately 2 kb DNA fragment comprising the coding sequence of the farnesene synthase gene was PCR amplified using primers GW-110-26-pGAL7-FS F (SEQ ID NO: 121) and GW-110-26-FS-BamHI R (SEQ ID NO: 122). The two DNA fragments were stitched together using PCR primers GW-110-26-pGAL7-PstI F (SEQ ID NO: 119) and GW-110-26-FS-BamHI R (SEQ ID NO: 122) to create a $P_{GAL7}$-FS-tCYC1 insert. The $P_{GAL7}$-FS-tCYC1 insert and plasmid pRS425 were digested to completion using PstI and BamHI restriction endonucleases, and the two DNA fragments were ligated, yielding pAM728.

Plasmid pAM940 was generated by introducing the farnesene synthase sequence of plasmid pAM728 into plasmid pRS426 (Christianson et al. (1992) Gene 110(1):119-122). Plasmids pAM728 and pRS426 were digested to completion using XhoI and BamHI restriction endonucleases, the reaction mixtures were resolved by gel electrophoresis, the approximately 5.7 kb pRS426 vector backbone and the approximately 2.5 kb $P_{GAL7}$-FS-tCYC1 insert of pAM728 were gel purified, and the two DNA fragments were ligated, yielding plasmid pAM940.

Figure 7:
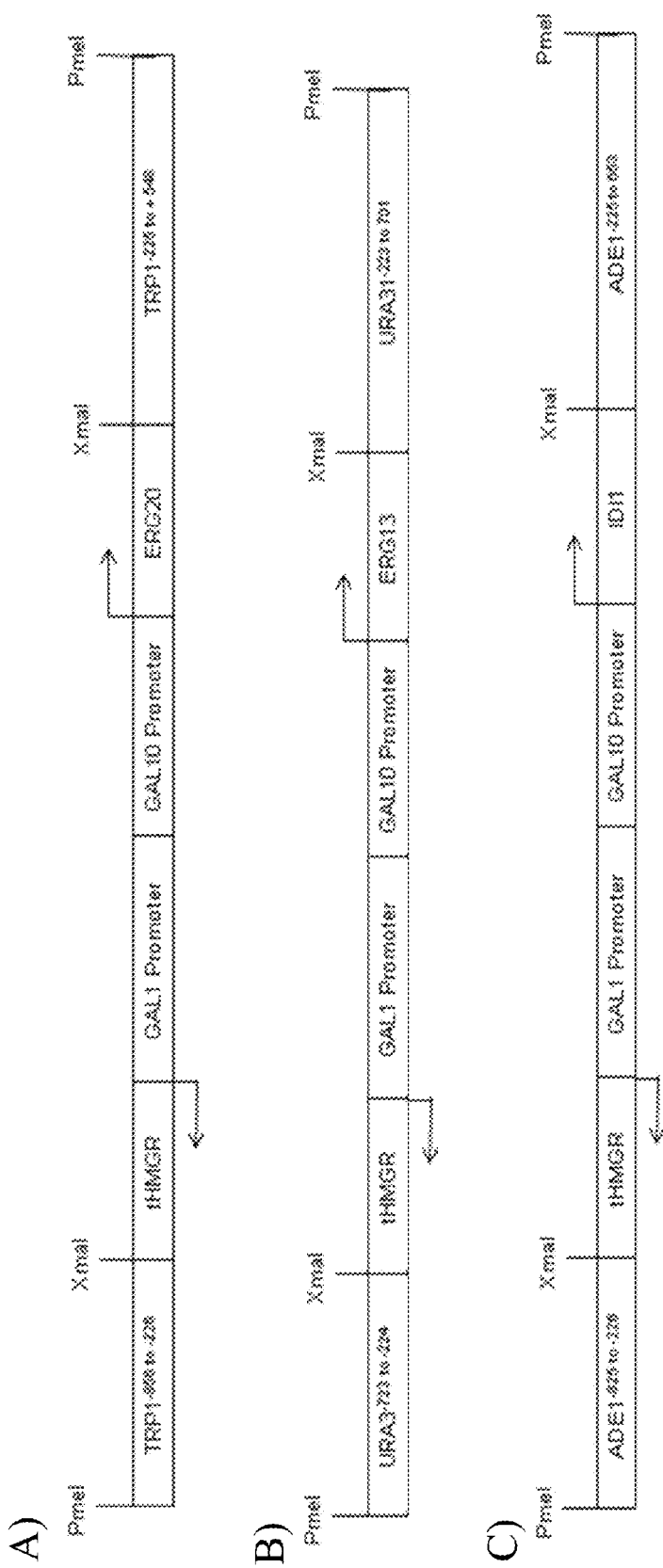
FIGS. 7A-G show maps of the inserts of vectors pAM489, pAM491, pAM493, pAM495, pAM497, and pAM584, and of the integration cassette natA-P$_{CTR3}^{-1\ to\ -734}$.
Figure 7:
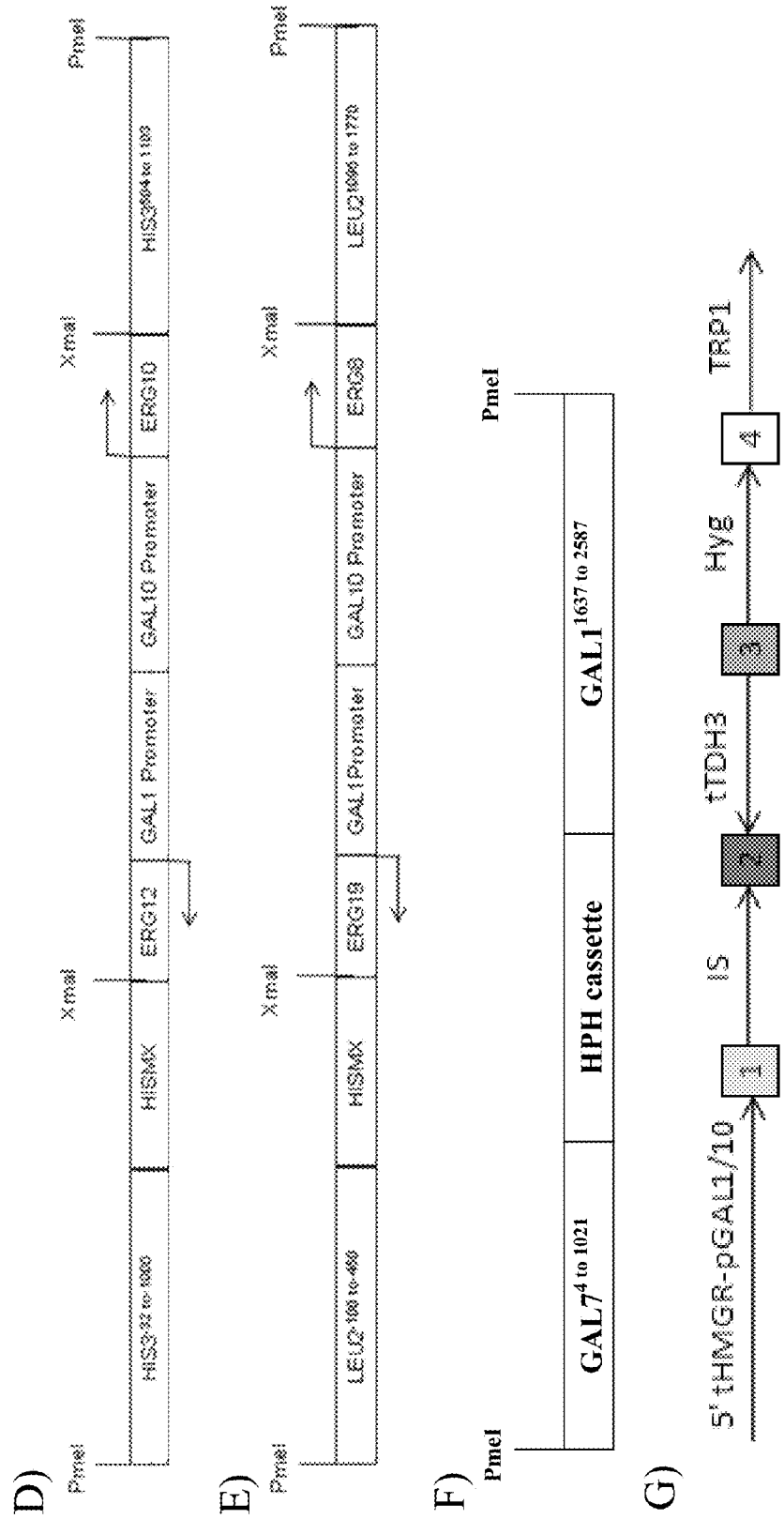

Plasmid pAM489 was generated by inserting the ERG20-$P_{GAL}$-tHMGR insert of vector pAM471 into vector pAM466. Vector pAM471 was generated by inserting DNA fragment ERG20-$P_{GAL}$-tHMGR, which comprises the open reading frame (ORF) of the ERG20 gene of *Saccharomyces cerevisiae* (ERG20 nucleotide positions 1 to 1208; A of ATG start codon is nucleotide 1) (ERG20), the genomic locus containing the divergent GAL1 and GAL10 promoter of *Saccharomyces cerevisiae* (GAL1 nucleotide position −1 to −668) ($P_{GAL}$), and a truncated ORF of the HMG1 gene of *Saccharomyces cerevisiae* (HMG1 nucleotide positions 1586 to 3323) (tHMGR), into the TOPO Zero Blunt II cloning vector (Invitrogen, Carlsbad, Calif.). Vector pAM466 was generated by inserting DNA fragment TRP1$^{-856\ to\ +548}$, which comprises a segment of the wild-type TRP1 locus of *Saccharomyces cerevisiae* that extends from nucleotide position −856 to position 548 and harbors a non-native internal XmaI restriction site between bases −226 and −225, into the TOPO TA pCR2.1 cloning vector (Invitrogen,q Carlsbad, Calif.). DNA fragments ERG20-$P_{GAL}$-tHMGR and TRP1$^{-856\ to\ +548}$ were generated by PCR amplification as outlined in Table 1. For the construction of pAM489, 400 ng of pAM471 and 100 ng of pAM466 were digested to completion using XmaI restriction enzyme (New England Biolabs, Ipswich, Mass.), DNA fragments corresponding to the ERG20-$P_{GAL}$-tHMGR insert and the linearized pAM466 vector were gel purified, and 4 molar equivalents of the purified insert was ligated with 1 molar equivalent of the purified linearized vector, yielding pAM489. FIG. 7A shows a map of the ERG20-$P_{GAL}$-tHMGR insert, and SEQ ID NO: 9 shows the nucleotide sequence of the DNA fragment and the flanking TRP1 sequences.

TABLE 1

PCR amplifications performed to generate pAM489

| PCR Round | Template | Primer 1 | Primer 2 | PCR Product |
|---|---|---|---|---|
| 1 | 100 ng of Y051 genomic DNA | 61-67-CPK001-G (SEQ ID NO: 23) | 61-67-CPK002-G (SEQ ID NO: 24) | TRP1$^{-856\ to\ -226}$ |
|  |  | 61-67-CPK003-G (SEQ ID NO: 25) | 61-67-CPK004-G (SEQ ID NO: 26) | TRP1$^{-225\text{-}to\ +548}$ |
|  | 100 ng of EG123 genomic DNA | 61-67-CPK025-G (SEQ ID NO: 47) | 61-67-CPK050-G (SEQ ID NO: 55) | ERG20 |
|  | 100 ng of Y002 genomic DNA | 61-67-CPK051-G (SEQ ID NO: 56) | 61-67-CPK052-G (SEQ ID NO: 57) | $P_{GAL}$ |
|  |  | 61-67-CPK053-G (SEQ ID NO: 58) | 61-67-CPK031-G (SEQ ID NO: 48) | tHMGR |
| 2 | 100 ng each of TRP1$^{-856\ to\ -226}$ and TRP1$^{-225\text{-}to\ +548}$ purified PCR products | 61-67-CPK001-G (SEQ ID NO: 23) | 61-67-CPK004-G (SEQ ID NO: 26) | TRP1$^{-856\ to\ +548}$ |
|  | 100 ng each of ERG20 and $P_{GAL}$ purified PCR products | 61-67-CPK025-G (SEQ ID NO: 47) | 61-67-CPK052-G (SEQ ID NO: 57) | ERG20-$P_{GAL}$ |
| 3 | 100 ng each of ERG20-$P_{GAL}$ and tHMGR purified PCR products | 61-67-CPK025-G (SEQ ID NO: 47) | 61-67-CPK031-G (SEQ ID NO: 48) | ERG20-$P_{GAL}$-tHMGR |

Plasmid pAM491 was generated by inserting the ERG13-$P_{GAL}$-tHMGR insert of vector pAM472 into vector pAM467. Vector pAM472 was generated by inserting DNA fragment ERG13-$P_{GAL}$-tHMGR, which comprises the ORF of the ERG13 gene of Saccharomyces cerevisiae (ERG13 nucleotide positions 1 to 1626) (ERG13), the genomic locus containing the divergent GAL1 and GAL10 promoter of Saccharomyces cerevisiae (GAL1 nucleotide position −1 to −668) ($P_{GAL}$), and a truncated ORF of the HMG1 gene of Saccharomyces cerevisiae (HMG1 nucleotide position 1586 to 3323) (tHMGR), into the TOPO Zero Blunt II cloning vector. Vector pAM467 was generated by inserting DNA fragment URA3$^{-723\ to\ -701}$, which comprises a segment of the wild-type URA3 locus of Saccharomyces cerevisiae that extends from nucleotide position −723 to position −224 and harbors a non-native internal XmaI restriction site between bases −224 and −223, into the TOPO TA pCR2.1 cloning vector. DNA fragments ERG13-$P_{GAL}$-tHMGR and URA3$^{-723\ to\ 701}$ were generated by PCR amplification as outlined in Table 2. For the construction of pAM491, 400 ng of pAM472 and 100 ng of pAM467 were digested to completion using XmaI restriction enzyme, DNA fragments corresponding to the ERG13-$P_{GAL}$-tHMGR insert and the linearized pAM467 vector were gel purified, and 4 molar equivalents of the purified insert was ligated with 1 molar equivalent of the purified linearized vector, yielding pAM491. FIG. 7B shows a map of the ERG13-$P_{GAL}$-tHMGR insert, and SEQ ID NO: 10 shows the nucleotide sequence of the DNA fragment and the flanking URA3 sequences.

TABLE 2

PCR amplifications performed to generate pAM491

| PCR Round | Template | Primer 1 | Primer 2 | PCR Product |
|---|---|---|---|---|
| 1 | 100 ng of Y007 genomic DNA | 61-67-CPK005-G (SEQ ID NO: 27) | 61-67-CPK006-G (SEQ ID NO: 28) | URA3$^{-723\ to\ -224}$ |
|  |  | 61-67-CPK007-G (SEQ ID NO: 29) | 61-67-CPK008-G (SEQ ID NO: 30) | URA3$^{-223\ to\ 701}$ |
|  | 100 ng of Y002 genomic DNA | 61-67-CPK032-G (SEQ ID NO: 49) | 61-67-CPK054-G (SEQ ID NO: 59) | ERG13 |
|  |  | 61-67-CPK052-G (SEQ ID NO: 57) | 61-67-CPK055-G (SEQ ID NO: 60) | $P_{GAL}$ |
|  |  | 61-67-CPK031-G (SEQ ID NO: 48) | 61-67-CPK053-G (SEQ ID NO: 58) | tHMGR |
| 2 | 100 ng each of URA3$^{-723\ to\ -224}$ and URA3$^{-223\ to\ 701}$ purified PCR products | 61-67-CPK005-G (SEQ ID NO: 27) | 61-67-CPK008-G (SEQ ID NO: 30) | URA3$^{-723\ to\ 701}$ |
|  | 100 ng each of ERG13 and $P_{GAL}$ purified PCR products | 61-67-CPK032-G (SEQ ID NO: 49) | 61-67-CPK052-G (SEQ ID NO: 57) | ERG13-$P_{GAL}$ |
| 3 | 100 ng each of ERG13-$P_{GAL}$ and tHMGR purified PCR products | 61-67-CPK031-G (SEQ ID NO: 48) | 61-67-CPK032-G (SEQ ID NO: 49) | ERG13-$P_{GAL}$-tHMGR |

Plasmid pAM493 was generated by inserting the IDI1-$P_{GAL}$-tHMGR insert of vector pAM473 into vector pAM468. Vector pAM473 was generated by inserting DNA fragment IDI1-$P_{GAL}$-tHMGR, which comprises the ORF of the IDI1 gene of Saccharomyces cerevisiae (IDI1 nucleotide position 1 to 1017) (IDI1), the genomic locus containing the divergent GAL1 and GAL10 promoter of Saccharomyces cerevisiae (GAL1 nucleotide position −1 to −668) ($P_{GAL}$), and a truncated ORF of the HMG1 gene of Saccharomyces cerevisiae (HMG1 nucleotide positions 1586 to 3323) (tHMGR), into the TOPO Zero Blunt II cloning vector. Vector pAM468 was generated by inserting DNA fragment ADE1$^{-825\ to\ 653}$, which comprises a segment of the wild-type ADE1 locus of *Saccharomyces cerevisiae* that extends from nucleotide position −225 to position 653 and harbors a non-native internal XmaI restriction site between bases −226 and −225, into the TOPO TA pCR2.1 cloning vector. DNA fragments IDI1-P$_{GAL}$-tHMGR and ADE1$^{-825\ to\ 653}$ were generated by PCR amplification as outlined in Table 3. For the construction of pAM493, 400 ng of pAM473 and 100 ng of pAM468 were digested to completion using XmaI restriction enzyme, DNA fragments corresponding to the IDI1-P$_{GAL}$-tHMGR insert and the linearized pAM468 vector were gel purified, and 4 molar equivalents of the purified insert was ligated with 1 molar equivalent of the purified linearized vector, yielding vector pAM493. FIG. 7C shows a map of the IDI1-P$_{GAL}$-tHMGR insert, and SEQ ID NO: 11 shows the nucleotide sequence of the DNA fragment and the flanking ADE1 sequences.

ORF of the ERG12 gene of *Saccharomyces cerevisiae* (ERG12 nucleotide position 1 to 1482) (ERG12), into the TOPO Zero Blunt II cloning vector. Vector pAM469 was generated by inserting DNA fragment HIS3$^{-32\ to\ -1000}$-HISMX-HIS3$^{504\ to\ -1103}$, which comprises two segments of the HIS locus of *Saccharomyces cerevisiae* that extend from nucleotide position −32 to position −1000 and from nucleotide position 504 to position 1103, a HISMX marker, and a non-native XmaI restriction site between the HIS3$^{504\ to\ -1103}$ sequence and the HISMX marker, into the TOPO TA pCR2.1 cloning vector. DNA fragments ERG10-P$_{GAL}$-ERG12 and HIS3$^{-32\ to\ -1000}$-HISMX-HIS3$^{504\ to\ -1103}$ were generated by PCR amplification as outlined in Table 4. For construction of pAM495, 400 ng of pAM474 and 100 ng of pAM469 were digested to completion using XmaI restriction enzyme, DNA

TABLE 3

PCR amplifications performed to generate pAM493

| PCR Round | Template | Primer 1 | Primer 2 | PCR Product |
|---|---|---|---|---|
| 1 | 100 ng of Y007 genomic DNA | 61-67-CPK009-G (SEQ ID NO: 31) | 61-67-CPK010-G (SEQ ID NO: 32) | ADE1$^{-825\ to\ -226}$ |
| | | 61-67-CPK011-G (SEQ ID NO: 33) | 61-67-CPK012-G (SEQ ID NO: 34) | ADE1$^{-225\ to\ 653}$ |
| | 100 ng of Y002 genomic DNA | 61-67-CPK047-G (SEQ ID NO: 54) | 61-67-CPK064-G (SEQ ID NO: 69) | IDI1 |
| | | 61-67-CPK052-G (SEQ ID NO: 57) | 61-67-CPK065-G (SEQ ID NO: 70) | P$_{GAL}$ |
| | | 61-67-CPK031-G (SEQ ID NO: 48) | 61-67-CPK053-G (SEQ ID NO: 58) | tHMGR |
| 2 | 100 ng each of ADE1$^{-825\ to\ -226}$ and ADE1$^{-225\ to\ 653}$ purified PCR products | 61-67-CPK009-G (SEQ ID NO: 31) | 61-67-CPK012-G (SEQ ID NO: 34) | ADE1$^{-825\ to\ 653}$ |
| | 100 ng each of IDI1 and P$_{GAL}$ purified PCR products | 61-67-CPK047-G (SEQ ID NO: 54) | 61-67-CPK052-G (SEQ ID NO: 57) | IDI1-P$_{GAL}$ |
| 3 | 100 ng each of IDI1-P$_{GAL}$ and tHMGR purified PCR products | 61-67-CPK031-G (SEQ ID NO: 48) | 61-67-CPK047-G (SEQ ID NO: 54) | IDI1-P$_{GAL}$-tHMGR |

Plasmid pAM495 was generated by inserting the ERG10-P$_{GAL}$-ERG12 insert of pAM474 into vector pAM469. Vector pAM474 was generated by inserting DNA fragment ERG10-P$_{GAL}$-ERG12, which comprises the ORF of the ERG10 gene of *Saccharomyces cerevisiae* (ERG10 nucleotide position 1 to 1347) (ERG10), the genomic locus containing the divergent GAL1 and GAL10 promoter of *Saccharomyces cerevisiae* (GAL1 nucleotide position −1 to −668) (P$_{GAL}$), and the fragments corresponding to the ERG10-P$_{GAL}$-ERG12 insert and the linearized pAM469 vector were gel purified, and 4 molar equivalents of the purified insert was ligated with 1 molar equivalent of the purified linearized vector, yielding vector pAM495. FIG. 7D shows a map of the ERG10-P$_{GAL}$-ERG12 insert, and SEQ ID NO: 12 shows the nucleotide sequence of the DNA fragment and the flanking HIS3 sequences.

TABLE 4

PCR reactions performed to generate pAM495

| PCR Round | Template | Primer 1 | Primer 2 | PCR Product |
|---|---|---|---|---|
| 1 | 100 ng of Y007 genomic DNA | 61-67-CPK013-G (SEQ ID NO: 35) | 61-67-CPK014alt-G (SEQ ID NO: 36) | HIS3$^{-32\ to\ -1000}$ |
| | | 61-67-CPK017-G (SEQ ID NO: 39) | 61-67-CPK018-G (SEQ ID NO: 40) | HIS3$^{504\ to\ -1103}$ |
| | | 61-67-CPK035-G (SEQ ID NO: 50) | 61-67-CPK056-G (SEQ ID NO: 61) | ERG10 |
| | | 61-67-CPK057-G (SEQ ID NO: 62) | 61-67-CPK058-G (SEQ ID NO: 63) | P$_{GAL}$ |
| | | 61-67-CPK040-G (SEQ ID NO: 51) | 61-67-CPK059-G (SEQ ID NO: 64) | ERG12 |
| | 10 ng of plasmid pAM330 DNA** | 61-67-CPK015alt-G (SEQ ID NO: 37) | 61-67-CPK016-G (SEQ ID NO: 38) | HISMX |
| 2 | 100 ng each of HIS3$^{504\ to\ -1103}$ and HISMX PCR purified products | 61-67-CPK015alt-G (SEQ ID NO: 37) | 61-67-CPK018-G (SEQ ID NO: 40) | HISMX-HIS3$^{504\ to\ -1103}$ |
| | 100 ng each of ERG10 and | 61-67-CPK035-G | 61-67-CPK058-G | ERG10-P$_{GAL}$ |

TABLE 4-continued

PCR reactions performed to generate pAM495

| PCR Round | Template | Primer 1 | Primer 2 | PCR Product |
|---|---|---|---|---|
| | $P_{GAL}$ purified PCR products | (SEQ ID NO: 50) | (SEQ ID NO: 63) | |
| 3 | 100 ng each of HIS3$^{-32\ to\ -1000}$ and HISMX-HIS3$^{504\ to\ -1103}$ purified PCR products | 61-67-CPK013-G (SEQ ID NO: 35) | 61-67-CPK018-G (SEQ ID NO: 40) | HIS3$^{-32\ to\ -1000}$-HISMX-HIS3$^{504\ to\ -1103}$ |
| | 100 ng each of ERG10-$P_{GAL}$ and ERG12 purified PCR products | 61-67-CPK035-G (SEQ ID NO: 50) | 61-67-CPK040-G (SEQ ID NO: 51) | ERG10-$P_{GAL}$-ERG12 |

**The HISMX marker in pAM330 originated from pFA6a-HISMX6-PGAL1 as described by van Dijken et al. ((2000) Enzyme Microb. Technol. 26(9-10): 706-714).

Plasmid pAM497 was generated by inserting the ERG8-$P_{GAL}$-ERG19 insert of pAM475 into vector pAM470. Vector pAM475 was generated by inserting DNA fragment ERG8-$P_{GAL}$-ERG19, which comprises the ORF of the ERG8 gene of *Saccharomyces cerevisiae* (ERG8 nucleotide position 1 to 1512) (ERG8), the genomic locus containing the divergent GAL1 and GAL10 promoter of *Saccharomyces cerevisiae* (GAL1 nucleotide position −1 to −668) ($P_{GAL}$), and the ORF of the ERG19 gene of *Saccharomyces cerevisiae* (ERG19 nucleotide position 1 to 1341) (ERG19), into the TOPO Zero Blunt II cloning vector. Vector pAM470 was generated by inserting DNA fragment LEU2$^{-100\ to\ 450}$-HISMX-LEU2$^{1096\ to\ 1770}$, which comprises two segments of the LEU2 locus of *Saccharomyces cerevisiae* that extend from nucleotide position −100 to position 450 and from nucleotide position 1096 to position 1770, a HISMX marker, and a non-native XmaI restriction site between the LEU2$^{1096\ to\ 1770}$ sequence and the HISMX marker, into the TOPO TA pCR2.1 cloning vector. DNA fragments ERG8-$P_{GAL}$-ERG19 and LEU2$^{-100\ to\ 450}$-HISMX-LEU2$^{1096\ to\ 1770}$ were generated by PCR amplification as outlined in Table 5. For the construction of pAM497, 400 ng of pAM475 and 100 ng of pAM470 were digested to completion using XmaI restriction enzyme, DNA fragments corresponding to the ERG8-$P_{GAL}$-ERG19 insert and the linearized pAM470 vector were purified, and 4 molar equivalents of the purified insert was ligated with 1 molar equivalent of the purified linearized vector, yielding vector pAM497. FIG. 7E for a map of the ERG8-$P_{GAL}$-ERG19 insert, and SEQ ID NO: 13 shows the nucleotide sequence of the DNA fragment and the flanking LEU2 sequences.

TABLE 5

PCR reactions performed to generate pAM497

| PCR Round | Template | Primer 1 | Primer 2 | PCR Product |
|---|---|---|---|---|
| 1 | 100 ng of Y007 genomic DNA | 61-67-CPK019-G (SEQ ID NO: 41) | 61-67-CPK020-G (SEQ ID NO: 42) | LEU2$^{-100\ to\ 450}$ |
| | | 61-67-CPK023-G (SEQ ID NO: 45) | 61-67-CPK024-G (SEQ ID NO: 46) | LEU2$^{1096\ to\ 1770}$ |
| | 10 ng of plasmid pAM330 DNA** | 61-67-CPK021-G (SEQ ID NO: 43) | 61-67-CPK022-G (SEQ ID NO: 44) | HISMX |
| | 100 ng of Y002 genomic DNA | 61-67-CPK041-G (SEQ ID NO: 52) | 61-67-CPK060-G (SEQ ID NO: 65) | ERG8 |
| | | 61-67-CPK061-G (SEQ ID NO: 66) | 61-67-CPK062-G (SEQ ID NO: 67) | $P_{GAL}$ |
| | | 61-67-CPK046-G (SEQ ID NO: 53) | 61-67-CPK063-G (SEQ ID NO: 68) | ERG19 |
| 2 | 100 ng each of LEU2$^{1096\ to\ 1770}$ and HISMX purified PCR products | 61-67-CPK021-G (SEQ ID NO: 43) | 61-67-CPK024-G (SEQ ID NO: 46) | HISMX-LEU2$^{1096\ to\ 1770}$ |
| | 100 ng each of ERG8 and $P_{GAL}$ purified PCR products | 61-67-CPK041-G (SEQ ID NO: 52) | 61-67-CPK062-G (SEQ ID NO: 67) | ERG8-$P_{GAL}$ |
| 3 | 100 ng of LEU2$^{-100\ to\ 450}$ and HISMX-LEU2$^{1096\ to\ 1770}$ purified PCR products | 61-67-CPK019-G (SEQ ID NO: 41) | 61-67-CPK024-G (SEQ ID NO: 46) | LEU2$^{-100\ to\ 450}$-HISMX-LEU2$^{1096\ to\ 1770}$ |
| | 100 ng each of ERG8-$P_{GAL}$ and ERG19 purified PCR products | 61-67-CPK041-G (SEQ ID NO: 52) | 61-67-CPK046-G (SEQ ID NO: 53) | ERG8-$P_{GAL}$-ERG19 |

**The HISMX marker in pAM330 originated from pFA6a-HISMX6-PGAL1 as described by van Dijken et al. ((2000) Enzyme Microb. Technol. 26(9-10): 706-714).

Plasmid pAM584 was generated by inserting DNA fragment GAL7$^{4\ to\ 1021}$-HPH-GAL1$^{1637\ to\ 2587}$ into the TOPO ZERO Blunt II cloning vector (Invitrogen, Carlsbad, Calif.).

DNA fragment GAL7$^{4\ to\ 1021}$-HPH-GAL1$^{1637\ to\ 2587}$ comprises a segment of the ORF of the GAL7 gene of *Saccharomyces cerevisiae* (GAL7 nucleotide positions 4 to 1021) (GAL7$^{4\ to\ 1021}$), the hygromycin resistance cassette (HPH), and a segment of the 3' untranslated region (UTR) of the GAL1 gene of *Saccharomyces cerevisiae* (GAL1 nucleotide positions 1637 to 2587). The DNA fragment was generated by PCR amplification as outlined in Table 6. FIG. 7F shows a map and SEQ ID NO: 102 the nucleotide sequence of DNA fragment GAL7$^{4\ to\ 1021}$-HPH-GAL1$^{1637\ to\ 2587}$.

TABLE 6

PCR reactions performed to generate pAM584

| PCR Round | Template | Primer 1 | Primer 2 | PCR Product |
|---|---|---|---|---|
| 1 | 100 ng of Y002 genomic DNA | 91-014-CPK236-G (SEQ ID NO: 126) | 91-014-CPK237-G (SEQ ID NO: 127) | GAL7$^{4\ to\ 1021}$ |
|  |  | 91-014-CPK232-G (SEQ ID NO: 124) | 91-014-CPK233-G (SEQ ID NO: 125) | GAL1$^{1637\ to\ 2587}$ |
|  | 10 ng of plasmid pAM547 DNA** | 91-014-CPK231-G (SEQ ID NO: 123) | 91-014-CPK238-G (SEQ ID NO: 128) | HPH |
| 2 | 100 ng each of GAL7$^{4\ to\ 1021}$ and HPH purified PCR products | 91-014-CPK231-G (SEQ ID NO: 123) | 91-014-CPK236-G (SEQ ID NO: 126) | GAL7$^{4\ to\ 1021}$-HPH |
| 3 | 100 ng of each GAL1$^{1637\ to\ 2587}$ and GAL7$^{4\ to\ 1021}$-HPH purified PCR products | 91-014-CPK233-G (SEQ ID NO: 125) | 91-014-CPK236-G (SEQ ID NO: 126) | GAL7$^{4\ to\ 1021}$-HPH-GAL1$^{1637\ to\ 2587}$ |

**Plasmid pAM547 was generated synthetically, and comprises the HPH cassette, which consists of the coding sequence for the hygromycin B phosphotransferase of *Escherichia coli* flanked by the promoter and terminator of the Tef1 gene of *Kluyveromyces lactis*.

Integration cassette natA-P$_{CTR3}$$^{1\ to\ -734}$ was generated by PCR amplifying the natA marker using primers PW287-002-CPK1217 (SEQ ID NO: 104) and DE PW91-027-CPK262-G (SEQ ID NO: 99) and using plasmid DNA comprising the TEF1 promoter and terminator of *Kluyveromyces lactis* (GenBank accession CR382122 REGIONS:788874 . . . 789380 and 787141 . . . 787496, respectively) and the nat resistance marker. In addition, the promoter of the CTR3 gene of *Saccharomyces cerevisiae* was PCR amplified from Y002 genomic DNA from positions −1 to −734 using primers PW287-002-CPK1232 (SEQ ID NO: 100) and DE_PW91-027-CPK263-G (SEQ ID NO: 101). The 2 PCR products were stitched together in a secondary PCR reaction using 25 ng of each of the gel purified PCR fragments and primers PW287-002-CPK1217 and PW287-002-CPK1232, yielding integration cassette natA-P$_{CTR3}$$^{-1\ to\ -734}$.

Additional recombinant integration cassettes were generated by stitching RABits. RABits were generated by inserting DNA fragments of interest (MULEs) into the pMULE Entry vector.

Figure 8:
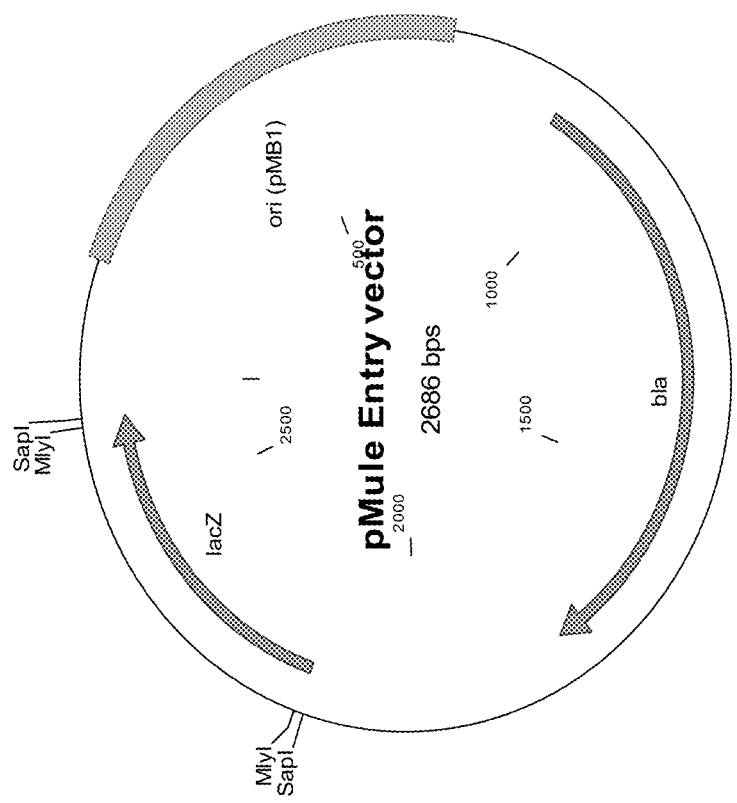
FIG. 8 shows a map of the pMULE Entry vector.

The pMULE Entry vector was PCR amplified using primers K162 (SEQ ID NO: 73) and K163 (SEQ ID NO: 74) and pRYSE Entry vector 8 (SEQ ID NO: 14) as template. The reaction mixture was resolved by gel electrophoresis, and the approximately 2.2 kb vector backbone was gel purified. A DNA fragment comprising the lacZ coding sequence was generated by digesting to completion pRYSE Entry vector 8 using SchI restriction enzyme, heat inactivating the enzyme (20 min at 65° C.), resolving the reaction mixture by gel electrophoresis, and gel purifying the approximately 0.5 kb DNA fragment. The purified DNA fragment comprising the lacZ coding sequence was ligated with the purified vector backbone, yielding the pMULE Entry vector (see FIG. 8 for a plasmid map).

MULEs were PCR amplified using templates and primers as outlined in Table 7. PCR amplifications were done using the Phusion DNA polymerase (New England Bio labs, Ipswich, Mass.) as per manufacturer's suggested protocol.

TABLE 7

Amplified MULEs

| MULE | Primers | Template | Size (bp) |
|---|---|---|---|
| 5' ERG20-pGAL1/10 | YD-198-75A (SEQ ID NO: 94) | pAM489 | 1,012 |

TABLE 7-continued

Amplified MULEs

| MULE | Primers | Template | Size (bp) |
|---|---|---|---|
| mIS2081 | YD-198-75B (SEQ ID NO: 95) YD-198-75F (SEQ ID NO: 96) | Genetrix2081 | 1,836 |
| mIS2081T | YD-198-75H (SEQ ID NO: 98) YD-198-75G (SEQ ID NO: 97) | Genetrix2081 | 1,668 |
| tTDH3 | YD-198-75H (SEQ ID NO: 98) RYSE 4 (SEQ ID NO: 77) RYSE 7 (SEQ ID NO: 78) | RABit63* | 311 |
| Hyg | YD-198-75L (SEQ ID NO: 105) YD-198-75M (SEQ ID NO: 106) | RABit21* | 1,962 |
| TRP1 | YD-198-75N (SEQ ID NO: 107) YD-198-75O (SEQ ID NO: 108) | pAM489 | 586 |

*RABit21 comprises SEQ ID NO: 15, and RABit63 comprises SEQ ID NO: 16.

RABits were generated by inserting the MULEs into the pMULE Entry vector. The PCR reactions were resolved by gel electrophoresis, the MULEs were gel purified, the purified MULEs were treated with T4 polynucleotide kinase (PNK) (New England Bio labs, Ipswich, Mass.) as per manufacturer's suggested protocol, and the PNK was heat inactivated at 65° C. for 20 minutes. The pMULE Entry vector was digested to completion using SchI restriction enzyme, the approximately 2.2 kb pMULE Entry vector backbones (lacking lacZ) was gel purified, the purified pMULE Entry vector backbone was treated with Antarctic Phosphatase (New England Biolabs, Ipswich, Mass.), and the phosphatase was heat inactivated at 65° C. for 20 minutes. The pMULE Entry vector backbone was ligated with each of the amplified MULEs, yielding RABits.

RABits to be stitched (Table 8) were placed together in one tube (333 fmole of each RABit) and digested to completion using LguI restriction enzyme (Fermentas, Glen Burnie, Md.). The restriction enzyme was heat inactivated for 20 minutes at 65° C. The RABit digestion reactions were split into three 30 uL reactions; water, buffer, dNTPs, and DNA polymerase were added to each reaction mixture, and a first round of PCR amplification was initiated. Samples were placed on ice, 0.5 uM of each terminal primer (Table 8) were added to the reaction mixtures, and a second round of PCR amplification was performed. The three PCR reaction mixtures were combined in one tube, the reaction mixtures were resolved by gel electrophoresis, and the PCR products were gel purified. FIG. 7G shows a map of the integration cassettes.

TABLE 8

PCR Amplification of Integration Cassettes

| Integration Cassette | RABits to be combined | Terminal Primers for 2$^{nd}$ Round PCR amplification |
| --- | --- | --- |
| i00280 | 5' ERG20-pGAL1/10 - mIS2081 - tTDH3 - Hyg - TRP1 | YD-198-75A (SEQ ID NO: 94) |
| i00281 | 5' ERG20-pGAL1/10 - mIS2081T - tTDH3 - Hyg - TRP1 | YD-198-75O (SEQ ID NO: 108) |

The first round of PCR amplification was performed as follows: one cycle of denature at 98° C. for 2 minutes; 5 cycles of denature at 98° C. for 30 seconds and anneal/extend at 72° C. for 30 seconds per kilobase PCR product. The second round of PCR amplification was performed as follows: one cycle of denature at 98° C. for 2 minutes; 35 rounds of denature at 98° C. for 12 seconds and anneal/extend at 72° C. for 20 seconds per kilobase PCR product; one cycle of final extend at 72° C. for 7 minutes; and a final hold at 4° C.

Example 3

This example describes methods for generating *Saccharomyces cerevisiae* strains expressing heterologous isoprene synthases.

*Saccharomyces cerevisiae* strains CEN.PK2-1C (Y002) (MATA; ura3-52; trp1-289; leu2-3,112; his3Δ1; MAL2-8C; SUC2) and CEN.PK2-1D (Y003) (MATalpha; ura3-52; trp1-289; leu2-3,112; his3Δ1; MAL2-8C; SUC2) (van Dijken et al. (2000) Enzyme Microb. Technol. 26(9-10):706-714) were prepared for introduction of inducible MEV pathway genes by replacing the ERG9 promoter with the *Saccharomyces cerevisiae* MET3 promoter, and the ADE1 ORF with the *Candida glabrata* LEU2 gene (CgLEU2). This was done by PCR amplifying the KanMX-P$_{MET3}$ region of vector pAM328 (SEQ ID NO: 17) using primers 50-56-pw100-G (SEQ ID NO: 19) and 50-56-pw101-G (SEQ ID NO: 20), which include 45 base pairs of homology to the native ERG9 promoter, transforming 10 μg of the resulting PCR product into exponentially growing Y002 and Y003 cells using 40% w/w Polyethelene Glycol 3350 (Sigma-Aldrich, St. Louis, Mo.), 100 mM Lithium Acetate (Sigma-Aldrich, St. Louis, Mo.), and 10 μg Salmon Sperm DNA (Invitrogen Corp., Carlsbad, Calif.), and incubating the cells at 30° C. for 30 minutes followed by heat shocking them at 42° C. for 30 minutes (Schiestl and Gietz. (1989) Curr. Genet. 16, 339-346). Positive recombinants were identified by their ability to grow on rich medium containing 0.5 μg/ml Geneticin (Invitrogen Corp., Carlsbad, Calif.), and selected colonies were confirmed by diagnostic PCR. The resultant clones were given the designation Y93 (MAT A) and Y94 (MAT alpha). The 3.5 kb CgLEU2 genomic locus was then amplified from *Candida glabrata* genomic DNA (ATCC, Manassas, Va.) using primers 61-67-CPK066-G (SEQ ID NO: 71) and 61-67-CPK067-G (SEQ ID NO: 72), which contain 50 base pairs of flanking homology to the ADE1 ORF, and 10 μg of the resulting PCR product were transformed into exponentially growing Y93 and Y94 cells, positive recombinants were selected for growth in the absence of leucine supplementation, and selected clones were confirmed by diagnostic PCR. The resultant clones were given the designation Y176 (MAT A) and Y177 (MAT alpha).

Strain Y188 was generated by digesting 2 μg of pAM491 and pAM495 plasmid DNA to completion using PmeI restriction endonucleose (New England Biolabs, Beverly, Mass.), and introducing the purified DNA inserts into exponentially growing Y176 cells. Positive recombinants were selected for by growth on medium lacking uracil and histidine, and integration into the correct genomic locus was confirmed by diagnostic PCR.

Strain Y189 was generated by digesting 2 μg of pAM489 and pAM497 plasmid DNA to completion using PmeI restriction endonuclease, and introducing the purified DNA inserts into exponentially growing Y177 cells. Positive recombinants were selected for by growth on medium lacking tryptophan and histidine, and integration into the correct genomic locus was confirmed by diagnostic PCR.

Strain Y238 was generated by mixing approximately 1×10$^7$ cells from strains Y188 and Y189 on a YPD medium plate for 6 hours at room temperature to allow for mating, plating the mixed cell culture to medium lacking histidine, uracil, and tryptophan to select for growth of diploid cells, digesting 2 μg of pAM493 plasmid DNA to completion using PmeI restriction endonuclease, and introducing the purified DNA insert into the exponentially growing diploid cells. Positive recombinants were selected for by growth on medium lacking adenine, and integration into the correct genomic locus was confirmed by diagnostic PCR.

Strains Y210 (Mat A) and Y211 (MAT alpha) were generated by sporulating strain Y238 in 2% Potassium Acetate and 0.02% Raffinose liquid medium, isolating approximately 200 genetic tetrads using a Singer Instruments MSM300 series micromanipulator (Singer Instrument LTD, Somerset, UK), identifying independent genetic isolates containing the appropriate complement of introduced genetic material by their ability to grow in the absence of adenine, histidine, uracil, and tryptophan, and confirming the integration of all introduced DNA by diagnostic PCR.

Strain Y258 was generated by transforming strain Y211 with pAM404 plasmid DNA. Host cell transformants were selected on synthetic defined media, containing 2% glucose and all amino acids except leucine (SM-glu). Single colonies were transferred to culture vials containing 5 mL of liquid SM-glu lacking leucine, and the cultures were incubated by shaking at 30° C. until growth reached stationary phase. The cells were stored at −80° C. in cryo-vials in 1 mL frozen aliquots made up of 400 uL 50% sterile glycerol and 600 uL liquid culture.

Strains Y225 (MAT A) and Y227 (MAT alpha) were generated by transforming exponentially growing Y210 and Y211 cells, respectively, with 2 μg of pAM426 (SEQ ID NO: 18), which comprises a GAL1 promoter operably linked to the coding sequence of an amorpha-4,11-diene synthase gene that is codon-optimized for expression in *Saccharomyces cerevisiae* (Merke et al. (2000) Ach. Biochem. Biophys. 381: 173-180). Host cell transformants were selected on complete synthetic defined media lacking leucine.

Strain Y337 was generated from strain Y227 by rendering the strain unable to catabolize galactose. To this end, pAM584 plasmid DNA was digested to completion using PmeI restriction endonuclease, and the purified DNA insert GAL7$^{4\ to\ 1021}$-HPH-GAL1$^{11637\ to\ 2587}$ was introduced into exponentially growing Y227 cells. Positive recombinants were selected for by growth on solid medium lacking adenine, leucine, lysine, histidine, methionine, uracil, and tryptophan, and containing 900 μg/mL hygromycin B (Sigma, St. Louis, Mo.). Integration into the correct genomic locus was confirmed by diagnostic PCR and by testing the strain for inability to use galactose as a carbon source.

Strain Y615 was generated from strain Y337 by replacing the URA3 open reading frame with the hisG open reading frame from *Salmonella* sp. A DNA fragment comprising the hisG open reading frame was PCR amplified from pAM840 using primers 100-150-KB034-G (SEQ ID NO: 109) and 100-150-KB039-G (SEQ ID NO: 110), and the purified DNA fragment was introduced into exponentially growing Y337 cells. Positive transformants were selected for their ability to grow on medium containing 5-fluoroorotic acid and for their inability to grow on medium lacking uracil. Integration into the correct genomic locus was confirmed by diagnostic PCR.

Strain Y1775 was generated from strain Y615 by replacing the kanMX marker with the URA3 marker. A DNA fragment encoding the *S. cerevisiae* URA3 auxotrophic marker was PCR amplified from pAM64 (SEQ ID NO: 103) using primers PW-191-046-CPK1212-G (SEQ ID NO: 111) and PW-191-046-CPK1213-G (SEQ ID NO: 112), and the purified DNA fragment was introduced into exponentially growing Y615 cells. Positive recombinants were selected for by growth on medium lacking adenine, leucine, lysine, histidine, methionine, uracil, and tryptophan. Integration into the correct genomic locus was confirmed by diagnostic PCR.

Strain Y1791 was generated from strain Y1775 by restoring the ERG9 locus. A DNA fragment comprising the ERG9 open reading frame was PCR amplified from Y002 genomic DNA using primers PW-191-015-CPK947-G (SEQ ID NO: 113) and PW-191-015-CPK950-G (SEQ ID NO: 114), and the purified DNA fragment was introduced into exponentially growing Y1775 cells. Positive transformants we selected for their ability to grow on medium containing 5-fluoroorotic acid and for their inability to grow on medium lacking uracil. Integration into the correct genomic locus was confirmed by diagnostic PCR.

Strain Y1856 was generated from strain Y1791 by restoring the GAL1, GAL10, and GAL7 locus. A DNA fragment comprising the GAL1, GAL10, and GAL7 genomic region was PCR amplified from Y002 genomic DNA using primers PW-91-093-CPK453-G (SEQ ID NO: 115) and PW-091-144-CPK689-G (SEQ ID NO: 116), and the purified DNA fragment was introduced into exponentially growing Y1791 cells. Positive recombinants were selected for by growth on medium containing 20 g/L glacatose and their inability to grow on medium containing 900 μg/mL hygromycin B.

Strain Y1857 was generated from strain Y1856 by disrupting the P$_{GAL10}$-ERG20 locus. A DNA fragment encoding the *S. cerevisiae* URA3 auxotrophic marker was PCR amplified from pAM64 (SEQ ID NO: 130) using primers PW-287-002-CPK1215-G (SEQ ID NO: 117) and PW-287-002-CPK1216-G (SEQ ID NO: 118), and the purified DNA fragment was introduced into exponentially growing Y1856 cells. Positive recombinants were selected for by growth on medium lacking adenine, leucine, lysine, histidine, methionine, uracil, and tryptophan. Integration into the correct genomic locus was confirmed by diagnostic PCR.

Strain Y1895 was generated from strain Y1857 by curing the strain from pAM426. Strain Y1857 was propagated in rich Yeast Extract Peptone Dextrose (YPD) medium contain 0.5% leucine (w/v) for 5 days. Every 12 hours, fresh YPD 0.5% LEU was inoculated to an OD$_{600}$ of 0.05 using the previous 12 hour growth. After 5 days, the cells were plated on YPD 0.5% leucine agar medium and incubated at 30° C. for 2 days. Cured cells were identified by their ability to grow on minimal medium containing leucine and their inability to grow on medium lacking leucine.

Strain Y736 was generated from strain Y227 by replacing the URA3 marker with a hisG marker. To this end, the hisG marker was PCR amplified using primers KB34 (SEQ ID NO: 75) and KB39 (SEQ ID NO: 76) and plasmid pAM840 as template. Exponentially growing Y211 cells were transformed with the PCR mixture and were then plated on YPD overnight. Host cell transformants were selected by replica plating cells from the YPD plates onto Complete Synthetic Medium (CSM) solid media lacking methionine and leucine and containing 0.1% 5-FOA and 0.1 mg/ml uracil.

Strain Y737 was generated from strain Y736 by transforming exponentially growing cells with pAM940, and selecting host cell transformants on CSM solid media lacking leucine and uracil.

Strain Y846 was generated from strain Y737 by curing the strain of pAM426. To this end, strain Y737 was grown for 3 successive nights in rich media supplemented with 6× the usual concentration of leucine, being diluted each morning 100×. The cells were then plated out to well-separated single colonies on rich media and replica plated onto minimal media lacking leucine. Colonies that grew on rich media but did not grow in the absence of leucine were picked, grown, and tested by PCR to verify that the plasmid was no longer present. One such positive colony was stocked as Y846.

Strain Y1858 was generated from strain Y1895 by heterologous expression of an isoprene synthase. To this end, exponentially growing Y1895 cells were transformed with expression plasmid pAM1547. Host cell transformants were selected on CSM agar lacking methionine and leucine and containing 2% glucose.

Strain Y1859 was generated from strain Y1895 by heterologous expression of an isoprene synthase. To this end, exponentially growing Y1895 cells were transformed with expression plasmid pAM1548. Host cell transformants were selected on CSM agar lacking methionine and leucine and containing 2% glucose.

Strain Y1860 was generated from strain Y1895 by heterologous expression of an isoprene synthase. To this end, exponentially growing Y1895 cells were transformed with expression plasmid pAM1549. Host cell transformants were selected on CSM agar lacking methionine and leucine and containing 2% glucose.

Strain Y1861 was generated from strain Y1895 by heterologous expression of an isoprene synthase. To this end, exponentially growing Y1895 cells were transformed with expression plasmid pAM1550. Host cell transformants were selected on CSM agar lacking methionine and leucine and containing 2% glucose.

Strain Y1713 was generated from strain Y846 by replacing the ERG20 gene with the coding sequence for an isoprene synthase. To this end, exponentially growing Y846 cells were transformed with integration cassette 100280. Host cell transformants were selected on YPD agar containing 2% glucose and 300 μg/mL hygromycin B (A.G. Scientific, San Diego, Calif.).

Strain Y1714 was generated from strain Y846 by replacing the ERG20 gene with a coding sequence for a truncated isoprene synthase. To this end, exponentially growing Y846 cells were transformed with integration cassette i00281. Host cell transformants were selected on YPD agar containing 2% glucose and 300 µg/mL hygromycin B (A.G. Scientific, San Diego, Calif.).

Strain Y1732 was generated from strain Y846 by heterologous expression of an isoprene synthase. To this end, exponentially growing Y846 cells were transformed with expression plasmid pAM1549. Host cell transformants were selected on CSM agar lacking methionine and leucine and containing 2% glucose.

Strain Y1733 was generated from strain Y846 by heterologous expression of a truncated isoprene synthase. To this end, exponentially growing Y846 cells were transformed with expression plasmid pAM1550. Host cell transformants were selected on CSM agar lacking methionine and leucine and containing 2% glucose.

Strain Y1837 was generated by transforming exponentially growing Y1713 cells with expression plasmid pAM1549. Host cell transformants were selected on CSM agar lacking methionine and leucine and containing 2% glucose.

Strain Y1838 was generated by transforming exponentially growing Y1714 cells with expression plasmid pAM1550. Host cell transformants were selected on CSM agar lacking methionine and leucine and containing 2% glucose.

Strain 1907 was generated from strain Y1860 by replacing the ERG20 promoter with the nourseothricin resistance marker (natA) and the copper repressible promoter of the CTR3 gene of *Saccharomyces cerevisiae*. To this end, exponentially growing Y1860 cells were transformed with 200 µg of the integration cassette natA-$P_{CTR3}^{-1\ to\ -734}$. Host cell transformants were selected for by growth on rich YPD medium containing 300 µg/mL nourseothricin (Werner Bio-Agents, Jena, Germany).

Example 4

This example describes methods for producing isoprene in *Saccharomyces cerevisiae* host strains.

Single colonies of host cell transformants were transferred to culture vials containing 5 mL of Bird Seed Medium containing 0.25 uM $CuSO_4$. The following day, 20 mL of Bird Production Medium containing 1.8% galactose, 0.2% glucose, and 32 uM $CuSO_4$, with 4 mL isopropylmyristate, was inoculated with host cell transformant Y1858, Y1859, Y1860, or Y1861 to an $OD_{600}$ of 0.05. Similarly, 20 mL of Bird Production Medium containing 1.8% galactose and 0.2% glucose, with 4 mL isopropylmyristate, was inoculated with isolates #3, 6, or 9 of host cell transformant Y1907 to an $OD_{600}$ of 0.05. To the Y1907 culture, 0.25 uM $CuSO_4$, 50 uM $CuSO_4$, or 150 uM $CuSO_4$ was added. The shake flasks were sealed for anaerobic growth and incubated at 30° C. on a rotary shaker at 200 rpm.

After 72 hours of growth, the cultures were assayed for cell growth. At the same time, 200 uL of isopropylmyristate was removed from each flask and were injected directly on an Agilent 7980 gas chromatograph equipped with a flame ionization detector. To expedite run times, the temperature program and column matrix were modified to achieve optimal resolution and the shortest overall runtime (15.0 min). Each 2 µL sample was split 10:1 and was separated using a Varian fused silica CP-PoraBond U PLOT (25 m×0.32 mm×7 um; length×width×film thickness) column with hydrogen as the carrier gas. The temperature program for the analysis was as follows: the column was initially held at 100° C. for 1 minute, followed by a temperature gradient of 10° C./min to a temperature of 140° C., followed by a temperature gradient of 40° C./min to a temperature of 250° C., followed by holding the column at 250° C. for 6.5 min. Under these conditions, isoprene elutes at 5.8 minutes.

What is claimed is:

1. A method of making isoprene comprising:
   a. culturing a plurality of host cells capable of making isoprene;
   b. making isoprene by the host cells by taking a carbohydrate carbon source;
   c. forming a first gaseous composition comprising the isoprene from step b and water, wherein the water is present in an amount greater than about 70% of its saturation amount;
   d. subjecting the first gaseous composition to a first cooling step whereby substantially all of the water is removed from the first gaseous composition resulting in a second gaseous composition; and
   e. subjecting the second gaseous composition to a second cooling step whereby a liquid isoprene composition is collected.

2. The method of claim 1, further comprising nitrogen stripping the liquid isoprene composition.

3. The method of claim 1, wherein the isoprene is present in an amount that is between about 0.1% and about 15% by volume in the first gaseous composition.

4. The method of claim 1, wherein the first gaseous composition further comprises carbon dioxide in an amount between about 1% and about 35% by volume.

5. The method of claim 1, wherein the first cooling step cools the first gaseous composition to a temperature between about 10° C. and about −15° C.

6. The method of claim 1, wherein the first cooling step is cooled using a propylene refrigeration system.

7. The method of claim 1, wherein the first cooling step is cooled using an ammonium refrigeration system.

8. The method of claim 1, wherein the second cooling step cools the second gaseous composition to a temperature between about −60° C. and about −85° C.

9. The method of claim 1, wherein the second cooling step is cooled using an ethylene refrigeration system.

10. The method of claim 1, wherein the host cells are selected from the genus *Bacillus, Escherichia* or *Acinetobacter*.

11. The method of claim 10, wherein the host cells are *Escherichia coli*.

12. The method of claim 1, wherein the host cells are yeast.

13. The method of claim 12, wherein the host cells are *Saccharomyces cerevisiae*.

* * * * *

SEQUENCE LISTING

<160> NUMBER OF SEQ ID NOS: 128

<210> SEQ ID NO 1
<211> LENGTH: 1737
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
ggatccatgt caactttgcc tatttcttct gtgtcatttt cctcttctac atcaccatta      60
gtcgtggacg acaaagtctc aaccaagccc gacgttatca gacatacaat gaatttcaat     120
gcttctattt ggggagatca attcttgacc tatgatgagc ctgaagattt agttatgaag     180
aaacaattag tggaggaatt aaaagaggaa gttaagaagg aattgataac tatcaaaggt     240
tcaaatgagc ccatgcagca tgtgaaattg attgaattaa ttgatgctgt tcaacgttta     300
ggtatagctt accattttga agaagagatc gaggaagctt tgcaacatat acatgttacc     360
tatggtgaac agtgggtgga taaggaaaat ttacagagta tttcattgtg gttcaggttg     420
ttgcgtcaac agggcttttaa cgtctcctct ggcgttttca aagactttat ggacgaaaaa     480
ggtaaattca aagagtcttt atgcaatgat gcacaaggaa tattagcctt atatgaagct     540
gcatttatga gggttgaaga tgaaaccatc ttagacaatg ctttggaatt cacaaaagtt     600
catttagata tcatagcaaa agaccatctc tgcgattctt cattgcgtac acaaatccat     660
```

| | |
|---|---|
| caagccttaa aacaaccttt aagaaggaga ttagcaagga ttgaagcatt acattacatg | 720 |
| ccaatctacc aacaggaaac atctcatgat gaagtattgt tgaaattagc caagttggat | 780 |
| ttcagtgttt tgcagtctat gcataaaaag gaattgtcac atatctgtaa gtggtggaaa | 840 |
| gatttagatt tacaaaataa gttaccttat gtacgtgatc gtgttgtcga aggctacttc | 900 |
| tggatattgt ccatatacta tgagccacaa cacgctagaa caagaatgtt tttgatgaaa | 960 |
| acatgcatgt ggttagtagt tttggacgat acttttgata attatggaac atacgaagaa | 1020 |
| ttggagattt ttactcaagc cgtcgagaga tggtctatct catgcttaga tatgttgccc | 1080 |
| gaatatatga aattaatcta ccaagaatta gtcaatttgc atgtggaaat gaagaatct | 1140 |
| ttggaaaagg agggaaagac ctatcagatt cattacgtta aggagatggc taagaatta | 1200 |
| gttcgtaatt acttagtaga agcaagatgg ttgaaggaag gttatatgcc tactttagaa | 1260 |
| gaatacatgt ctgtttctat ggttactggt acttatggtt tgatgattgc aaggtcctat | 1320 |
| gttggcagag gagacattgt tactgaagac acattcaaat gggtttctag ttacccacct | 1380 |
| attattaaag cttcctgtgt aatagtaaga ttaatggacg atattgtatc tcacaaggaa | 1440 |
| gaacaagaaa gaggacatgt ggcttcatct atagaatgtt actctaaaga atcaggtgct | 1500 |
| tctgaagagg aagcatgtga atatattagt aggaaagttg aggatgcctg gaaagtaatc | 1560 |
| aatagagaat ctttgcgtcc aacagccgtt cccttccctt tgttaatgcc agcaataaac | 1620 |
| ttagctagaa tgtgtgaggt cttgtactct gttaatgatg gttttactca tgctgagggt | 1680 |
| gacatgaaat cttatatgaa gtccttcttc gttcatccta tggtcgtttg actcgag | 1737 |

<210> SEQ ID NO 2
<211> LENGTH: 7348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatcga ctacgtcgta aggccgtttc tgacagagta aaattcttga gggaactttc | 240 |
| accattatgg gaaatgcttc aagaaggtat tgacttaaac tccatcaaat ggtcaggtca | 300 |
| ttgagtgttt tttatttgtt gtatttttt tttttagag aaaatcctcc aatatcaaat | 360 |
| taggaatcgt agtttcatga ttttctgtta caccaacttt tttgtgtggt gccctcctcc | 420 |
| ttgtcaatat taatgttaaa gtgcaattct tttccttat cacgttgagc cattagtatc | 480 |
| aatttgctta cctgtattcc tttactatcc tcctttttct ccttcttgat aaatgtatgt | 540 |
| agattgcgta tatagtttcg tctaccctat gaacatattc cattttgtaa tttcgtgtcg | 600 |
| tttctattat gaatttcatt tataaagttt atgtacaaat atcataaaaa aagagaatct | 660 |
| ttttaagcaa ggatttttct taacttcttcg gcgacagcat caccgacttc ggtggtactg | 720 |
| ttggaaccac ctaaatcacc agttctgata cctgcatcca aaacctttt aactgcatct | 780 |
| tcaatggcct taccttcttc aggcaagttc aatgacaatt tcaacatcat tgcagcagac | 840 |
| aagatagtgg cgatagggtc aaccttattc tttggcaaat ctggagcaga accgtggcat | 900 |
| ggttcgtaca aaccaaatgc ggtgttcttg tctggcaaag aggccaagga cgcagatggc | 960 |
| aacaaaccca aggaacctgg gataacggag gcttcatcgg agatgatatc accaaacatg | 1020 |

```
ttgctggtga ttataatacc atttaggtgg gttgggttct taactaggat catggcggca  1080
gaatcaatca attgatgttg aaccttcaat gtagggaatt cgttcttgat ggtttcctcc  1140
acagttttc  tccataatct tgaagaggcc aaaagattag ctttatccaa ggaccaaata  1200
ggcaatggtg gctcatgttg tagggccatg aaagcggcca ttcttgtgat tctttgcact  1260
tctggaacgg tgtattgttc actatcccaa gcgacaccat caccatcgtc ttcctttctc  1320
ttaccaaagt aaatacctcc cactaattct ctgacaacaa cgaagtcagt acctttagca  1380
aattgtggct tgattggaga taagtctaaa agagagtcgg atgcaaagtt acatggtctt  1440
aagttggcgt acaattgaag ttcttacgg  atttttagta aaccttgttc aggtctaaca  1500
ctaccggtac cccatttagg accagccaca gcacctaaca aaacggcatc aaccttcttg  1560
gaggcttcca gcgcctcatc tggaagtgga acacctgtag catcgatagc agcaccacca  1620
attaaatgat tttcgaaatc gaacttgaca ttggaacgaa catcagaaat agctttaaga  1680
accttaatgg cttcggctgt gatttcttga ccaacgtggt cacctggcaa aacgacgatc  1740
ttcttagggg cagacattac aatggtatat ccttgaaata tataaaaaa  aaggcgcctt  1800
agaccgctcg gccaaacaac caattacttg ttgagaaata gagtataatt atcctataaa  1860
tataacgttt ttgaacacac atgaacaagg aagtacagga caattgattt tgaagagaat  1920
gtggattttg atgtaattgt tgggattcca tttttaataa ggcaataata ttaggtatgt  1980
ggatatacta gaagttctcc tcgaccgtcg atatgcggtg tgaaataccg cacagatgcg  2040
taaggagaaa ataccgcatc aggaaattgt aaacgttaat attttgttaa aattcgcgtt  2100
aaattttgt  taaatcagct cattttttaa ccaataggcc gaaatcggca aaatccctta  2160
taaatcaaaa gaatagaccg agatagggtt gagtgttgtt ccagtttgga acaagagtcc  2220
actattaaag aacgtggact ccaacgtcaa agggcgaaaa accgtctatc agggcgatgg  2280
cccactacgt gaaccatcac cctaatcaag tttttggg   tcgaggtgcc gtaaagcact  2340
aaatcggaac cctaaaggga gcccccgatt tagagcttga cggggaaagc cggcgaacgt  2400
ggcgagaaag gaagggaaga aagcgaaagg agcgggcgct agggcgctgg caagtgtagc  2460
ggtcacgctg cgcgtaacca ccacacccgc cgcgcttaat gcgccgctac agggcgcgtc  2520
gcgccattcg ccattcaggc tgcgcaactg ttgggaaggg cgatcggtgc gggcctcttc  2580
gctattacgc cagctgaatt ggagcgacct catgctatac ctgagaaagc aacctgacct  2640
acaggaaaga gttactcaag aataagaatt ttcgttttaa aacctaagag tcactttaaa  2700
atttgtatac acttattttt tttataactt atttaataat aaaaatcata aatcataaga  2760
aattcgctta tttagaagtg tcaacaacgt atctaccaac gatttgaccc ttttccatct  2820
tttcgtaaat ttctggcaag gtagacaagc cgacaacctt gattggagac ttgaccaaac  2880
ctctggcgaa gaattgttaa ttaagagctc agatcttatc gtcgtcatcc ttgtaatcca  2940
tcgatactag tgcggccgcc ctttagtgag ggttgaattc gaattttcaa aaattcttac  3000
tttttttttg gatggacgca aagaagttta ataatcatat acatggcat  taccaccata  3060
tacatatcca tatacatatc catatctaat cttacttata tgttgtggaa atgtaaagag  3120
ccccattatc ttagcctaaa aaaccttcct ctttggaact ttcagtaata cgcttaactg  3180
ctcattgcta tattgaagta cggattagaa gccgccgagc gggtgacagc cctccgaagg  3240
aagactctcc tccgtgcgtc ctcgtcttca ccggtcgcgt tcctgaaacg cagatgtgcc  3300
tcgcgccgca ctgctccgaa caataaagat tctacaatac tagcttttat ggttatgaag  3360
aggaaaaatt ggcagtaacc tggccccaca aaccttcaaa tgaacgaatc aaattaacaa  3420
```

```
ccataggatg ataatgcgat tagttttta gccttatttc tggggtaatt aatcagcgaa    3480
gcgatgattt ttgatctatt aacagatata taaatgcaaa aactgcataa ccactttaac    3540
taatactttc aacattttcg gtttgtatta cttcttattc aaatgtaata aaagtatcaa    3600
caaaaaattg ttaatatacc tctatacttt aacgtcaagg agaaaaaacc ccggatccgt    3660
aatacgactc actataggc ccgggcgtcg acatggaaca aagttgatt tccgaagaag      3720 acctcgagta agcttggtac cgcggctagc taagatccgc tctaaccgaa aggaaggag    3780 ttagacaacc tgaagtctag gtccctattt attttttat agttatgtta gtattaagaa     3840
cgttatttat atttcaaatt tttcttttt ttctgtacag acgcgtgtac gcatgtaaca     3900
ttatactgaa aaccttgctt gagaaggttt tgggacgctc gaagatccag ctgcattaat    3960
gaatcggcca acgcgcgggg agaggcggtt tgcgtattgg gcgctcttcc gcttcctcgc    4020
tcactgactc gctgcgctcg gtcgttcggc tgcggcgagc ggtatcagct cactcaaagg    4080
cggtaatacg gttatccaca gaatcagggg ataacgcagg aaagaacatg tgagcaaaag    4140
gccagcaaaa ggccaggaac cgtaaaaagg ccgcgttgct ggcgtttttc cataggctcc    4200
gcccccctga cgagcatcac aaaaatcgac gctcaagtca gaggtggcga aacccgacag    4260
gactataaag ataccaggcg tttcccctg gaagctccct cgtgcgctct cctgttccga     4320
ccctgccgct taccggatac ctgtccgcct ttctccctc gggaagcgtg gcgctttctc     4380
atagctcacg ctgtaggtat ctcagttcgg tgtaggtcgt tcgctccaag ctgggctgtg    4440
tgcacgaacc ccccgttcag cccgaccgct gcgccttatc cggtaactat cgtcttgagt    4500
ccaacccggt aagacacgac ttatcgccac tggcagcagc cactggtaac aggattagca    4560
gagcgaggta tgtaggcggt gctacagagt tcttgaagtg gtggcctaac tacggctaca    4620
ctagaaggac agtatttggt atctgcgctc tgctgaagcc agttaccttc ggaaaaagag    4680
ttggtagctc ttgatccggc aaacaaacca ccgctggtag cggtggtttt tttgtttgca    4740
agcagcagat tacgcgcaga aaaaaggat ctcaagaaga tccttttgat cttttctacgg    4800 ggtctgacgc tcagtggaac gaaaactcac gttaagggat tttggtcatg agattatcaa    4860
aaaggatctt cacctagatc cttttaaatt aaaaatgaag ttttaaatca atctaaagta    4920
tatatgagta aacttggtct gacagttacc aatgcttaat cagtgaggca cctatctcag    4980
cgatctgtct atttcgttca tccatagttg cctgactccc cgtcgtgtag ataactacga    5040
tacgggaggg cttaccatct ggccccagtg ctgcaatgat accgcgagac ccacgctcac    5100
cggctccaga tttatcagca ataaaccagc cagccggaag ggccgagcgc agaagtggtc    5160
ctgcaacttt atccgcctcc atccagtcta ttaattgttg ccgggaagct agagtaagta    5220
gttcgccagt taatagtttg cgcaacgttg ttgccattgc tacaggcatc gtggtgtcac    5280
gctcgtcgtt tggtatggct tcattcagct ccggttccca acgatcaagg cgagttacat    5340 gatccccat gttgtgcaaa aaagcggtta gctccttcgg tcctccgatc gttgtcagaa     5400
gtaagttggc cgcagtgtta tcactcatgg ttatggcagc actgcataat tctcttactg    5460
tcatgccatc cgtaagatgc ttttctgtga ctggtgagta ctcaaccaag tcattctgag    5520
aatagtgtat gcggcgaccg agttgctctt gcccggcgtc aatacgggat aataccgcgc    5580
cacatagcag aactttaaaa gtgctcatca ttggaaaacg ttcttcgggg cgaaaactct    5640
caaggatctt accgctgttg agatccagtt cgatgtaacc cactcgtgca cccaactgat    5700
cttcagcatc ttttactttc accagcgttt ctgggtgagc aaaaacagga aggcaaaatg    5760
ccgcaaaaaa gggaataagg gcgacacgga aatgttgaat actcatactc ttcctttttc    5820
```

-continued

| | |
|---|---|
| aatattattg aagcatttat cagggttatt gtctcatgag cggatacata tttgaatgta | 5880 |
| tttagaaaaa taaacaaata ggggttccgc gcacatttcc ccgaaaagtg ccacctgaac | 5940 |
| gaagcatctg tgcttcattt tgtagaacaa aaatgcaacg cgagagcgct aattttcaa | 6000 |
| acaaagaatc tgagctgcat ttttacagaa cagaaatgca acgcgaaagc gctattttac | 6060 |
| caacgaagaa tctgtgcttc attttttgtaa aacaaaaatg caacgcgaga gcgctaattt | 6120 |
| ttcaaacaaa gaatctgagc tgcatttttta cagaacagaa atgcaacgcg agagcgctat | 6180 |
| tttaccaaca aagaatctat acttctttttt tgttctacaa aaatgcatcc cgagagcgct | 6240 |
| atttttctaa caaagcatct tagattactt ttttttctcct ttgtgcgctc tataatgcag | 6300 |
| tctcttgata acttttttgca ctgtaggtcc gttaaggtta gaagaaggct actttggtgt | 6360 |
| ctattttctc ttccataaaa aaagcctgac tccacttccc gcgtttactg attactagcg | 6420 |
| aagctgcggg tgcatttttt caagataaag gcatccccga ttatattcta taccgatgtg | 6480 |
| gattgcgcat actttgtgaa cagaaagtga tagcgttgat gattcttcat tggtcagaaa | 6540 |
| attatgaacg gtttcttcta ttttgtctct atatactacg tataggaaat gtttacattt | 6600 |
| tcgtattgtt ttcgattcac tctatgaata gttcttacta caattttttt gtctaaagag | 6660 |
| taatactaga gataaacata aaaaatgtag aggtcgagtt tagatgcaag ttcaaggagc | 6720 |
| gaaaggtgga tgggtaggtt atataggat atagcacaga gatatatagc aaagagatac | 6780 |
| ttttgagcaa tgtttgtgga agcggtattc gcaatatttt agtagctcgt tacagtccgg | 6840 |
| tgcgttttg gttttttgaa agtgcgtctt cagagcgctt ttggttttca aaagcgctct | 6900 |
| gaagttccta tactttctag agaataggaa cttcggaata ggaacttcaa agcgtttccg | 6960 |
| aaaacgagcg cttccgaaaa tgcaacgcga gctgcgcaca tacagctcac tgttcacgtc | 7020 |
| gcacctatat ctgcgtgttg cctgtatata tatatacatg agaagaacgg catagtgcgt | 7080 |
| gtttatgctt aaatgcgtac ttatatgcgt ctatttatgt aggatgaaag gtagtctagt | 7140 |
| acctcctgtg atattatccc attccatgcg gggtatcgta tgcttccttc agcactaccc | 7200 |
| tttagctgtt ctatatgctg ccactcctca attggattag tctcatcctt caatgctatc | 7260 |
| atttcctttg atattggatc atactaagaa accattatta tcatgacatt aacctataaa | 7320 |
| aataggcgta tcacgaggcc ctttcgtc | 7348 |

<210> SEQ ID NO 3
<211> LENGTH: 952
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| | |
|---|---|
| taagtagttg accatagctc ttccatggct accaatttgt tgtgcttgtc taacaaattg | 60 |
| tcatcaccaa caccaactcc atctaccagg ttcccacaat ctaaaaactt cattactcaa | 120 |
| aagacctcat tggccaatcc taagccctgg agagtaatct gtgcaacctc atcacagttc | 180 |
| acccagatca cagaacataa ctctaggagg tcagcaaatt accagcctaa tttgtggaac | 240 |
| ttcgagttct tgcagtcttt ggagaatgat ttaaaggtcg aaaagttgga ggaaaaggct | 300 |
| acaaaattag aagaggaggt caggtgtatg atcaacaggg tagatactca gcctttgtca | 360 |
| ttgttagagt tgatagacga tgtccaaagg ttgggtttga cctataagtt tgaaaaggac | 420 |
| atcatcaagg ccttggaaaa catcgttttta ttggacgaga ataagaagaa caagtctgac | 480 |

```
ttacacgcca cagcattatc tttcaggttg ttgagacaac acggattcga ggtatctcag    540
gacgtctttg aaagatttaa agacaaggag ggaggttttt caggagaatt aaaaggagat    600
gtccaaggtt tgttgtcatt atacgaggcc tcatatttag gttttgaggg tgagaactta    660
ttggaagaag caaggacctt ttcaatcacc cacttgaaga ataacttaaa ggagggaata    720
aataccaagg tagctgagca agtatcacac gcattggaat taccttatca tcagagattg    780
cataggttag aagccagatg gttttttggat aagtatgaac ctaaggagcc tcaccaccag    840
ttattgttgg agttagccaa gttggacttt aatatggtcc aaacattaca ccagaaagag    900
ttgcaggact tgtctagatg gtggacagag atggggaaga gctggcttat tg             952

<210> SEQ ID NO 4
<211> LENGTH: 999
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
taagtagttg accatagctc ttccaaagag ttgcaggact tgtctagatg gtggacagag     60
atgggattgg catctaaatt agacttcgtc agagataggt tgatggaagt atatttctgg    120
gctttaggta tggcccctga tcctcaattt ggagagtgca gaaaagctgt aacaaaaatg    180
ttcggattag tcaccataat tgacgacgtt tatgacgttt acggtacatt ggacgagtta    240
caattgttta ctgatgcagt tgaaaggtgg gacgtcaatg ccattaatac cttaccagac    300
tacatgaaat tgtgcttctt agctttatac aacacagtaa acgacacatc ttactcaatc    360
ttgaaggaga agggtcacaa caacttgtct tacttgacta atcttggag ggagttgtgt    420 aaagccttct tacaagaggc caagtggtca acaacaaaa taatccctgc tttttcaaaa    480
tacttggaga acgcctctgt ctcttcatct ggagtagcat tattggcacc ttcatacttc    540
tctgtttgcc agcaacaaga ggacatatct gatcacgctt tgagatcatt aaccgatttt    600
cacggtttgg tacgatcttc atgcgtcata ttcagattat gcaatgactt agctacttca    660
gctgcagagt tagagagagg agagaccacc aactcaatca tctcttatat gcacgaaaac    720
gacggcacct cagaggaaca agcaagagag gagttgagga agttaatcga cgcagagtgg    780
aaaaagatga acagggagag ggtctctgat tcaacattgt tgccaaaggc cttcatggag    840
atagccgtca atatgccag ggtctcacac tgcacatatc agtacggtga cggtttgggt    900
aggcctgact acgccaccga aataggatc aagttgttgt tgatcgaccc tttttcctatt    960 aatcagttga tgtatgtctg aggaagagct ggcttattg                           999

<210> SEQ ID NO 5
<211> LENGTH: 932
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
taagtagttg accatagctc ttccatggct accgagttgt tgtgcttgca caggccaata     60 tcttttgaccc acaaattgtt caggaatcca ttgccaaaag tcatacaagc aacaccattg    120
accttgaagt taaggtgctc tgtatcaacc gagaacgttt cattcacaga acagaaaca     180 gaaacaagga ggtcagctaa ttacgagcca aactcatggg attatgacta cttgttgtct    240
```

```
tctgacaccg acgagtctat tgaggtatat aaagacaagg caaagaagtt ggaggctgaa      300
gtcaggaggg agatcaacaa cgaaaaggca gagttcttga ctttgccaga gttgattgac      360
aacgtacaga ggttgggatt gggttatagg tttgagtcag acataagaag ggctttggac      420
aggtttgtat cttcaggtgg attcgacgca gttactaaga cctcattgca tgctaccgct      480
ttatctttta ggttattgag acagcatggt tcgaagtat cacaggaggc attctcagga      540
ttcaaagacc agaacggaaa cttttttgaag aacttgaagg aggacataaa agccatcttg    600
tctttatacg aagcctcatt tttggcctta gagggtgaga atattttaga cgaggctaag      660
gtcttcgcca tatctcactt gaaggagttg tctgaggaga aaataggaaa ggacttagcc      720
gaacaagtaa accacgcatt ggaattacca ttgcatagga gaactcaaag gttagaagca      780
gtctggtcta tcgaggccta caggaagaaa gaggatgctg atcaggtttt attggagttg      840
gccatcttag actacaacat gatccagtca gtctatcaga gagacttgag agaaacttct      900
aggtggtgga aagggaagag gctggcttat tg                                    932

<210> SEQ ID NO 6
<211> LENGTH: 970
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
taagtagttg accatagctc ttcccttgag agaaacttct aggtggtgga gaagagtcgg      60
attagccact aaattgcact cgctaggga taggttaata gagtcattct attgggctgt      120
tggagtagct tttgaaccac aatactcaga ttgtaggaac tcagtagcca agatgttctc      180
attcgtcacc ataatcgatg acatctacga cgtatacgga actttggatg aattggaatt      240
attcactgat gcagtcgaga gatgggacgt aaatgccatt gatgacttgc ctgattacat      300
gaagttgtgc ttcttagctt tgtacaacac cataaacgag atcgcatacg acaacttgaa      360
ggacaagggt gaaatatat tgccttactt aaccaaggcc tgggctgatt tgtgtaacgc      420
attcttacag gaagcaaaat ggttgtataa caaatcaaca cctactttcg acgagtattt      480
tggtaacgct tggaagtctt catctggacc tttacaattg gtatttgctt acttcgccgt      540
cgtacaaaac attaagaaag aggagattga taacttgcaa aagtaccacg atatcatctc      600
aagaccatca cacatttttca ggttatgtaa cgacttggcc tctgcttcag ctgaaatagc     660
tagaggagag actgcaaatt cagtttcatg ttacatgagg accaagggta tatcagaaga     720
attagcaacc gaatctgtca tgaattaat cgacgagacc tggaagaaga tgaacaagga    780
aaagttggga ggttctttat tcgcaaaacc ttttgtcgaa acagccatca atttagccag     840
gcagtcacac tgtacatatc acaatggtga tgcccacacc tcacctgacg agttgaccag    900
gaaaagagtt ttgtcagtta ttactgaacc tatattacct tttgagaggt gaggaagagc     960
tggcttattg                                                            970

<210> SEQ ID NO 7
<211> LENGTH: 932
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
```

```
taagtagttg accatagctc ttccatggcc accgagttgt tgtgcttgca caggcctatc    60
tctttgaccc acaagttgtt caggaaccct ttgccaaagg taattcaagc cacaccattg   120
accttaaagt tgaggtgctc agtctctacc gagaacgtct ctttcaccga dacagagact   180
gaagctagga gatcagccaa ctacgagcca aattcatggg actacgactt cttgttatca   240
tctgacaccg acgagtcaat tgaggtctac aaagacaagg caaagaaatt ggaggcagag   300
gtcaggagag aaatcaacaa cgaaaaggcc gagttcttaa cttttgttgga gttgatcgac   360 aatgtacaga gattgggatt gggttacagg ttcgagtctg acattaggag ggctttagac   420
aggtttgttt catcaggtgg atttgacggt gtcacaaaaa catcattaca tgcaactgcc   480
ttgtctttca gattattaag gcaacatgga ttcgaagtct ctcaagaggc tttctctgga   540
ttcaaggacc agaacggtaa cttcttagag aatttgaaag aggacaccaa agcaattttg   600
tcattgtacg aggcttcatt cttggcattg gaaggtgaga atatcttgga tgaagcaaga   660
gtattcgcta tctctcactt gaaggagttg tctgaagaaa aaatcggaaa agaattggca   720
gagcaagtaa atcacgcctt agaattgcct ttacacagaa ggacacagag gttagaagca   780
gtctggtcta ttgaggctta tagaaagaag gaagatgcca accaagtatt gttggagttg   840 gccatttttgg actacaacat gatccagtca gtctaccaga gggacttaag agagacctct   900
aggtggtgga gaagggaaga gctggcttat tg                                  932

<210> SEQ ID NO 8
<211> LENGTH: 970
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
taagtagttg accatagctc ttcccttaag agagacctct aggtggtgga gaagagtagg    60
attagctact aaattgcact cgctaaggaa cagattaatc gaatcatttt actgggctgt   120
cggagtcgct tttgaacctc agtactctga ttgtagaaac tctgtagcca agatgttttc   180
tttcgtcacc atcatcgacg atatctacga cgtctatggt atcttggacg aattagagtt   240
gtttaccgat gctgtcgaaa ggtgggatgt taacgcaatt aatgatttgc ctgactacat   300
gaagttgtgc tttttagcct tatacaacac catcaacgag atcgcctatg acaacttgaa   360
ggacaaggga gagaacattt tgccatactt gaccaaggct tgggctgatt tatgtaacgc   420 cttttttacaa gaggccaagt ggttatacaa caagtctaca ccaaccttcg acgattattt   480
cggaaatgcc tggaaatctt catctggacc tttgcaattg atatttgcat acttcgcagt   540
tgtccagaac atcaaaaagg aggagatcga aaacttgcag aaataccacg acatcatctc   600
aaggccatca catatcttca ggttgtgcaa cgatttggca tcagcttctg ctgaaatcgc   660
aagaggagag acagctaatt cagtctcatg ctacatgagg actaagggaa tctcagaaga   720
attggccacc gaatcagtca tgaacttgat tgacgagacc tgcaaaaaga tgaacaagga   780
gaagttggga ggatctttgt ttgcaaaacc attcgtcgag accgccataa acttggctag   840
gcagtctcac tgcacctacc acaacggtga cgcccacaca tcacctgacg agttgaccag   900
gaaaagggta ttgtctgtta ttacagaacc aatcttacct tttgagaggt gaggaagagc   960
tggcttattg                                                           970

<210> SEQ ID NO 9
<211> LENGTH: 5050
```

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

| | | | | | |
|---|---|---|---|---|---|
| gtttaaacta | ctattagctg | aattgccact | gctatcgttg | ttagtggcgt | tagtgcttgc | 60 |
| attcaaagac | atggagggcg | ttattacgcc | ggagctcctc | gacagcagat | ctgatgactg | 120 |
| gtcaatatat | ttttgcattg | aggctctgtt | tggaattata | ttttgagatg | acccatctaa | 180 |
| tgtactggta | tcaccagatt | tcatgtcgtt | ttttaaagcg | gctgcttgag | tcttagcaat | 240 |
| agcgtcacca | tctggtgaat | cctttgaagg | aaccactgac | gaaggtttgg | acagtgacga | 300 |
| agaggatctt | tcctgctttg | aattagtcgc | gctgggagca | gatgacgagt | tggtggagct | 360 |
| gggggcagga | ttgctggccg | tcgtgggtcc | tgaatgggtc | cttggctggt | ccatctctat | 420 |
| tctgaaaacg | gaagaggagt | agggaatatt | actggctgaa | ataagtcttt | gaatgaacgt | 480 |
| atacgcgtat | atttctacca | atctctcaac | actgagtaat | ggtagttata | agaaagagac | 540 |
| cgagttaggg | acagttagag | gcggtggaga | tattccttat | ggcatgtctg | gcgatgataa | 600 |
| aacttttcaa | acggcagccc | cgatctaaaa | gagctgacac | ccgggagtta | tgacaattac | 660 |
| aacaacagaa | ttcttctat | atatgcacga | acttgtaata | tggaagaaat | tatgacgtac | 720 |
| aaactataaa | gtaaatattt | tacgtaacac | atggtgctgt | tgtgcttctt | tttcaagaga | 780 |
| ataccaatga | cgtatgacta | agtttaggat | ttaatgcagg | tgacggaccc | atctttcaaa | 840 |
| cgatttatat | cagtggcgtc | caaattgtta | ggttttgttg | gttcagcagg | tttcctgttg | 900 |
| tgggtcatat | gactttgaac | caaatggccg | gctgctaggg | cagcacataa | ggataattca | 960 |
| cctgccaaga | cggcacaggc | aactattctt | gctaattgac | gtgcgttggt | accaggagcg | 1020 |
| gtagcatgtg | ggcctcttac | acctaataag | tccaacatgg | caccttgtgg | ttctagaaca | 1080 |
| gtaccaccac | cgatggtacc | tacttcgatg | gatggcatgg | atacgaaat | tctcaaatca | 1140 |
| ccgtccactt | ctttcatcaa | tgttatacag | ttggaacttt | cgacattttg | tgcaggatct | 1200 |
| tgtcctaatg | ccagaaaaac | agctgtcact | aaattagctg | catgtgcgtt | aaatccacca | 1260 |
| acagacccag | ccattgcaga | tccaaccaaa | ttcttagcaa | tgttcaactc | aaccaatgcg | 1320 |
| gaaacatcac | tttttaacac | ttttctgaca | acatcaccag | gaatagtagc | ttctgcgacg | 1380 |
| acactcttac | cacgaccttc | gatccagttg | atggcagctg | ttttttgtc | ggtacagtag | 1440 |
| ttaccagaaa | cggagacaac | ctccatatct | tcccagccat | actcttctac | catttgcttt | 1500 |
| aatgagtatt | cgacacccct | agaaatcata | ttcatacccca | ttgcgtcacc | agtagttgtt | 1560 |
| ctaaatctca | tgaagagtaa | atctcctgct | agacaagttt | gaatatgttg | cagacgtgca | 1620 |
| aatcttgatg | tagagttaaa | agcttttta | attgcgtttt | gtccctcttc | tgagtctaac | 1680 |
| catatcttac | aggcaccaga | tcttttcaaa | gttgggaaac | ggactactgg | gcctcttgtc | 1740 |
| ataccatcct | tagttaaaac | agttgttgca | ccaccgccag | cattgattgc | cttacagcca | 1800 |
| cgcatggcag | aagctaccaa | acaaccctct | gtagttgcca | ttggtatatg | ataagatgta | 1860 |
| ccatcgataa | ccaaggggcc | tataacacca | acgggcaaag | gcatgtaacc | tataacattt | 1920 |
| tcacaacaag | cgccaaatac | gcggtcgtag | tcataatttt | tatatggtaa | acgatcagat | 1980 |
| gctaatacag | gagcttctgc | caaaattgaa | agagccttcc | tacgtaccgc | aaccgctctc | 2040 |
| gtagtatcac | ctaattttt | ctccaaagcg | tacaaaggta | acttaccgtg | aataaccaag | 2100 |
| gcagcgacct | ctttgttctt | caattgtttt | gtatttccac | tacttaataa | tgcttctaat | 2160 |

```
tcttctaaag gacgtatttt cttatccaag ctttcaatat cgcgggaatc atcttcctca    2220
ctagatgatg aaggtcctga tgagctcgat tgcgcagatg ataaactttt gactttcgat    2280
ccagaaatga ctgttttatt ggttaaaact ggtgtagaag cctttttgtac aggagcagta   2340
aaagacttct tggtgacttc agtcttcacc aattggtctg cagccattat agttttttct   2400
ccttgacgtt aaagtataga ggtatattaa caattttttg ttgatacttt tatgacattt   2460
gaataagaag taatacaaac cgaaaatgtt gaaagtatta gttaaagtgg ttatgcagct   2520
tttgcattta tatatctgtt aatagatcaa aaatcatcgc ttcgctgatt aattacccca   2580
gaaataaggc taaaaaacta atcgcattat tatcctatgg ttgttaattt gattcgttga   2640
tttgaaggtt tgtggggcca ggttactgcc aattttttcct cttcataacc ataaaagcta  2700
gtattgtaga atctttattg ttcggagcag tgcggcgcga ggcacatctg cgtttcagga   2760
acgcgaccgg tgaagaccag gacgcacgga ggagagtctt ccgtcggagg gctgtcgccc   2820
gctcggcggt ttctaatccg tacttcaata tagcaatgag cagttaagcg tattactgaa   2880
agttccaaag agaaggtttt tttaggctaa gataatgggg ctctttacat ttccacaaca   2940
tataagtaag attagatatg gatatgtata tggtggtatt gccatgtaat atgattatta   3000
aacttctttg cgtccatcca aaaaaaaagt aagaattttt gaaaattcaa tataaatggc   3060
ttcagaaaaa gaaattagga gagagagatt cttgaacgtt ttccctaaat tagtagagga   3120
attgaacgca tcgcttttgg cttacggtat gcctaaggaa gcatgtgact ggtatgccca   3180
ctcattgaac tacaacactc caggcggtaa gctaaataga gggtttgtccg ttgtggacac  3240
gtatgctatt ctctccaaca agaccgttga acaattgggg caagaagaat acgaaaaggt   3300
tgccattcta ggttggtgca ttgagttgtt gcaggcttac ttcttggtcg ccatgatgat   3360
gatggacaag tccattacca gaagaggcca accatgttgg tacaaggttc ctgaagttgg   3420
ggaaattgcc atcaatgacg cattcatgtt agaggctgct atctacaagc ttttgaaatc   3480
tcacttcaga aacgaaaaat actacataga tatcaccgaa ttgttccatg aggtcacctt   3540
ccaaaccgaa ttgggccaat tgatggactt aatcactgca cctgaagaca agtcgacttt   3600
gagtaagttc tcccctaaaga agcactcctt catagttact ttcaagactg cttactattc   3660
tttctacttg cctgtcgcat tggccatgta cgttgccggt atcacggatg aaaaggattt   3720
gaaacaagcc agagatgtct tgattccatt gggtgaatac ttccaaattc aagatgacta   3780
cttagactgc ttcggtaccc cagaacagat cggtaagatc ggtacagata tccaagataa   3840
caaatgttct tgggtaatca acaaggcatt ggaacttgct tccgcagaac aaagaaagac   3900
tttagacgaa aattacggta agaaggactc agtcgcagaa gccaaatgca aaaagatttt   3960
caatgacttg aaaattgaac agctatacca cgaatatgaa gagtctattg ccaaggattt   4020
gaaggccaaa atttctcagg tcgatgagtc tcgtggcttc aaagctgatg tcttaactgc   4080
gttcttgaac aaagtttaca agagaagcaa atagaactaa cgctaatcga taaaacatta   4140
gatttcaaac tagataagga ccatgtataa gaactatata cttccaatat aatatagtat   4200
aagctttaag atagtatctc tcgatctacc gttccacgtg actagtccaa ggatttttt   4260
taacccggga tatatgtgta ctttgcagtt atgacgccag atggcagtag tggaagatat   4320
tctttattga aaaatagctt gtcaccttac gtacaatctt gatccggagc ttttctttt   4380
ttgccgatta agaattcggt cgaaaaaaga aaaggagagg gccaagaggg agggcattgg   4440
tgactattga gcacgtgagt atacgtgatt aagcacacaa aggcagcttg gagtatgtct   4500
gttattaatt tcacaggtag ttctggtcca ttggtgaaag tttgcggctt gcagagcaca   4560
```

-continued

| | |
|---|---|
| gaggccgcag aatgtgctct agattccgat gctgacttgc tgggtattat atgtgtgccc | 4620 |
| aatagaaaga gaacaattga cccggttatt gcaaggaaaa tttcaagtct tgtaaaagca | 4680 |
| tataaaaata gttcaggcac tccgaaatac ttggttggcg tgtttcgtaa tcaacctaag | 4740 |
| gaggatgttt tggctctggt caatgattac ggcattgata tcgtccaact gcatggagat | 4800 |
| gagtcgtggc aagaatacca agagttcctc ggtttgccag ttattaaaag actcgtattt | 4860 |
| ccaaaagact gcaacatact actcagtgca gcttcacaga aacctcattc gtttattccc | 4920 |
| ttgtttgatt cagaagcagg tgggacaggt gaacttttgg attggaactc gatttctgac | 4980 |
| tgggttggaa ggcaagagag ccccgaaagc ttacatttta tgttagctgg tggactgacg | 5040 |
| ccgtttaaac | 5050 |

<210> SEQ ID NO 10
<211> LENGTH: 5488
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

| | |
|---|---|
| gtttaaactt gctaaattcg agtgaaacac aggaagacca gaaaatcctc atttcatcca | 60 |
| tattaacaat aatttcaaat gtttatttgc attatttgaa actagggaag acaagcaacg | 120 |
| aaacgttttt gaaaattttg agtattttca ataaatttgt agaggactca gatattgaaa | 180 |
| aaaagctaca gcaattaata cttgataaga gagtattga gaagggcaac ggttcatcat | 240 |
| ctcatggatc tgcacatgaa caaacaccag agtcaaacga cgttgaaatt gaggctactg | 300 |
| cgccaattga tgacaataca gacgatgata acaaaccgaa gttatctgat gtagaaaagg | 360 |
| attaaagatg ctaagagata gtgatgatat tcataaaata atgtaattct atatatgtta | 420 |
| attacctttt ttgcgaggca tatttatggt gaaggataag ttttgaccat caagaaggt | 480 |
| taatgtggct gtggtttcag ggtccatacc cgggagttat gacaattaca caacagaat | 540 |
| tctttctata tatgcacgaa cttgtaatat ggaagaaatt atgacgtaca actataaag | 600 |
| taaatatttt acgtaacaca tggtgctgtt gtgcttcttt ttcaagagaa taccaatgac | 660 |
| gtatgactaa gttaggatt taatgcaggt gacggaccca tctttcaaac gatttatatc | 720 |
| agtggcgtcc aaattgttag gttttgttgg ttcagcaggt ttcctgttgt gggtcatatg | 780 |
| actttgaacc aaatggccgg ctgctagggc agcacataag gataattcac ctgccaagac | 840 |
| ggcacaggca actattcttg ctaattgacg tgcgttggta ccaggagcgg tagcatgtgg | 900 |
| gcctcttaca cctaataagt ccaacatggc accttgtggt tctagaacag taccaccacc | 960 |
| gatggtacct acttcgatgg atggcatgga tacggaaatt ctcaaatcac cgtccacttc | 1020 |
| tttcatcaat gttatacagt tggaactttc gacattttgt gcaggatctt gtcctaatgc | 1080 |
| caagaaaaca gctgtcacta aattagctgc atgtgcgtta aatccaccaa cagacccagc | 1140 |
| cattgcagat ccaaccaaat tcttagcaat gttcaactca accatgcgg aaacatcact | 1200 |
| ttttaacact tttctgacaa catcaccagg aatagtagct tctgcgacga cactcttacc | 1260 |
| acgaccttcg atccagttga tggcagctgg ttttttgtcg gtacagtagt taccagaaac | 1320 |
| ggagacaacc tccatatctt cccagccata ctcttctacc atttgcttta atgagtattc | 1380 |
| gacacccta gaaatcatat tcataccccat tgcgtcacca gtagttgttc taaatctcat | 1440 |
| gaagagtaaa tctcctgcta gacaagtttg aatatgttgc agacgtgcaa atcttgatgt | 1500 |
| agagttaaaa gcttttttaa ttgcgttttg tccctcttct gagtctaacc atatcttaca | 1560 |

```
ggcaccagat cttttcaaag ttgggaaacg gactactggg cctcttgtca taccatcctt    1620
agttaaaaca gttgttgcac caccgccagc attgattgcc ttacagccac gcatggcaga    1680
agctaccaaa caaccctctg tagttgccat tggtatatga taagatgtac catcgataac    1740 caagggggcct ataacaccaa cgggcaaagg catgtaacct ataacatttt cacaacaagc    1800
gccaaatacg cggtcgtagt cataatttt atatggtaaa cgatcagatg ctaatacagg      1860
agcttctgcc aaaattgaaa gagccttcct acgtaccgca accgctctcg tagtatcacc    1920 taatttttc tccaaagcgt acaaaggtaa cttaccgtga ataaccaagg cagcgacctc     1980
tttgttcttc aattgttttg tatttccact acttaataat gcttctaatt cttctaaagg    2040
acgtattttc ttatccaagc tttcaatatc gcgggaatca tcttcctcac tagatgatga    2100
aggtcctgat gagctcgatt gcgcagatga taaacttttg actttcgatc cagaaatgac    2160
tgttttattg gttaaaactg gtgtagaagc cttttgtaca ggagcagtaa aagacttctt    2220
ggtgacttca gtcttcacca attggtctgc agccattata gttttttctc cttgacgtta    2280
aagtatagag gtatattaac aattttttgt tgatactttt atgacatttg aataagaagt    2340
aatacaaacc gaaaatgttg aaagtattag ttaaagtggt tatgcagctt ttgcatttat    2400
atatctgtta atagatcaaa aatcatcgct tcgctgatta attccccag aaataaggct     2460 aaaaaactaa tcgcattatt atcctatggt tgttaatttg attcgttgat ttgaaggttt    2520
gtggggccag gttactgcca atttttcctc ttcataacca taaaagctag tattgtagaa    2580
tctttattgt tcggagcagt gcggcgcgag gcacatctgc gtttcaggaa cgcgaccggt    2640
gaagaccagg acgcacggag gagagtcttc cgtcggaggg ctgtcgcccg ctcggcggct    2700
tctaatccgt acttcaatat agcaatgagc agttaagcgt attactgaaa gttccaaaga    2760
gaaggttttt ttaggctaag ataatggggc tctttacatt tccacaacat ataagtaaga    2820
ttagatatgg atatgtatat ggtggtattg ccatgtaata tgattattaa acttcttgc      2880 gtccatccaa aaaaaagta agaatttttg aaaattcaat ataaatgaaa ctctcaacta    2940
aactttgttg gtgtggtatt aaaggaagac ttaggccgca aaagcaacaa caattacaca    3000
atacaaactt gcaaatgact gaactaaaaa aacaaaagac cgctgaacaa aaaaccagac   3060
ctcaaaatgt cggtattaaa ggtatccaaa tttacatccc aactcaatgt gtcaaccaat    3120
ctgagctaga gaaatttgat ggcgtttctc aaggtaaata cacaattggt ctgggccaaa    3180
ccaacatgtc ttttgtcaat gacagagaag atatctactc gatgtcccta actgttttgt     3240
ctaagttgat caagagttac aacatcgaca ccaacaaaat tggtagatta gaagtcggta    3300
ctgaaactct gattgacaag tccaagtctg tcaagtctgt cttgatgcaa ttgtttggtg    3360
aaaacactga cgtcgaaggt attgacacgc ttaatgcctg ttacggtggt accaacgcgt    3420
tgttcaactc tttgaactgg attgaatcta acgcatggga tggtagagac gccattgtag    3480
tttgcggtga tattgccatc tacgataagg gtgccgcaag accaaccggt ggtgccggta    3540
ctgttgctat gtggatcggt cctgatgctc caattgtatt tgactctgta agagcttctt    3600
acatggaaca cgcctacgat ttttacaagc cagatttcac cagcgaatat ccttacgtcg    3660
atggtcattt ttcattaact tgttacgtca aggctcttga tcaagtttac aagagttatt    3720
ccaagaaggc tatttctaaa gggttggtta gcgatcccgc tggttcggat gctttgaacg    3780
ttttgaaata tttcgactac aacgttttcc atgttccaac ctgtaaattg gtcacaaaat    3840
catacggtag attactatat aacgatttca gagccaatcc tcaattgttc ccagaagttg    3900
acgccgaatt agctactcgc gattatgacg aatctttaac cgataagaac attgaaaaaa    3960
```

```
cttttgttaa tgttgctaag ccattccaca aagagagagt tgcccaatct ttgattgttc    4020
caacaaacac aggtaacatg tacaccgcat ctgtttatgc cgcctttgca tctctattaa    4080
actatgttgg atctgacgac ttacaaggca agcgtgttgg tttattttct tacggttccg    4140
gtttagctgc atctctatat tcttgcaaaa ttgttggtga cgtccaacat attatcaagg    4200
aattagatat tactaacaaa ttagccaaga gaatcaccga aactccaaag gattacgaag    4260
ctgccatcga attgagagaa aatgcccatt tgaagaagaa cttcaaacct caaggttcca    4320
ttgagcattt gcaaagtggt gtttactact tgaccaacat cgatgacaaa tttagaagat    4380
cttacgatgt taaaaaataa tcttccccca tcgattgcat cttgctgaac cccttcata    4440 aatgctttat tttttggca gcctgctttt tttagctctc atttaataga gtagtttttt    4500
aatctatata ctaggaaaac tctttattta ataacaatga tatatatata cccgggaagc    4560
ttttcaattc atctttttt tttttgttct tttttttgat tccggtttct ttgaaatttt    4620
tttgattcgg taatctccga gcagaaggaa gaacgaagga aggagcacag acttagattg    4680
gtatatatac gcatatgtgg tgttgaagaa acatgaaatt gcccagtatt cttaacccaa    4740
ctgcacagaa caaaaacctg caggaaacga agataaatca tgtcgaaagc tacatataag    4800
gaacgtgctg ctactcatcc tagtcctgtt gctgccaagc tatttaatat catgcacgaa    4860
aagcaaacaa acttgtgtgc ttcattggat gttcgtacca ccaaggaatt actgaagtta    4920
gttgaagcat taggtcccaa aatttgttta ctaaaaacac atgtggatat cttgactgat    4980
ttttccatgg agggcacagt taagccgcta aaggcattat ccgccaagta caatttttta    5040
ctcttcgaag acagaaaatt tgctgacatt ggtaatacag tcaaattgca gtactctgcg    5100
ggtgtataca gaatagcaga atgggcagac attacgaatg cacacggtgt ggtgggccca    5160
ggtattgtta gcggtttgaa gcaggcggcg gaagaagtaa caaaggaacc tagaggcctt    5220
ttgatgttag cagaattgtc atgcaagggc tccctagcta ctggagaata tactaagggt    5280
actgttgaca ttgcgaagag cgacaaagat tttgttatcg gctttattgc tcaaagagac    5340
atgggtggaa gagatgaagg ttacgattgg ttgattatga cacccggtgt gggtttagat    5400
gacaagggag acgcattggg tcaacagtat agaaccgtgg atgatgtggt ctctacagga    5460
tctgacatta ttattgttgg gtttaaac                                      5488
```

<210> SEQ ID NO 11
<211> LENGTH: 4933
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
gtttaaacta ctcagtatat taagtttcga attgaagggc gaactcttat tcgaagtcgg    60
agtcaccaca acacttccgc ccatactctc cgaatcctcg tttcctaaag taagtttact    120
tccacttgta ggcctattat taatgatatc tgaataatcc tctattaggg ttggatcatt    180
cagtagcgcg tgcgattgaa aggagtccat gcccgacgtc gacgtgatta gcgaaggcgc    240
gtaaccattg tcatgtctag cagctataga actaacctcc ttgacaccac ttgcggaagt    300
ctcatcaaca tgctcttcct tattactcat tctcttacca agcagagaat gttatctaaa    360
aactacgtgt atttcacctc tttctcgact tgaacacgtc caactcctta agtactacca    420
cagccaggaa agaatggatc cagttctaca cgatagcaaa gcagaaaaca caaccagcgt    480
```

```
accccctgtag aagcttcttt gtttacagca cttgatccat gtagccatac tcgaaatttc    540
aactcatctg aaacttttcc tgaaggttga aaaagaatgc cataagggtc acccgaagct    600
tattcacgcc cgggagttat gacaattaca acaacagaat tctttctata tatgcacgaa    660
cttgtaatat ggaagaaatt atgacgtaca aactataaag taaatatttt acgtaacaca    720
tggtgctgtt gtgcttcttt ttcaagagaa taccaatgac gtatgactaa gtttaggatt    780
taatgcaggt gacggaccca tctttcaaac gatttatatc agtggcgtcc aaattgttag    840
gttttgttgg ttcagcaggt ttcctgttgt gggtcatatg actttgaacc aaatggccgg    900
ctgctagggc agcacataag gataattcac ctgccaagac ggcacaggca actattcttg    960
ctaattgacg tgcgttggta ccaggagcgg tagcatgtgg gcctcttaca cctaataagt   1020
ccaacatggc accttgtggt tctagaacag taccaccacc gatggtacct acttcgatgg   1080
atggcatgga tacggaaatt ctcaaatcac cgtccacttc tttcatcaat gttatacagt   1140
tggaactttc gacattttgt gcaggatctt gtcctaatgc caagaaaaca gctgtcacta   1200
aattagctgc atgtgcgtta aatccaccaa cagacccagc cattgcagat ccaaccaaat   1260
tcttagcaat gttcaactca accaatgcgg aaacatcact ttttaacact tttctgacaa   1320
catcaccagg aatagtagct tctgcgacga cactcttacc acgaccttcg atccagttga   1380
tggcagctgt ttttttgtcg gtacagtagt taccagaaac ggagacaacc tccatatctt   1440
cccagccata ctcttctacc atttgcttta atgagtattc gacaccctta gaaatcatat   1500
tcatacccat tgcgtcacca gtagttgttc taaatctcat gaagagtaaa tctcctgcta   1560
gacaagtttg aatatgttgc agacgtgcaa atcttgatgt agagttaaaa gcttttttaa   1620
ttgcgttttg tccctcttct gagtctaacc atatcttaca ggaccagat cttttcaaag   1680 ttgggaaacg gactactggg cctcttgtca taccatcctt agttaaaaca gttgttgcac   1740
caccgccagc attgattgcc ttacagccac gcatggcaga agctaccaaa caaccctctg   1800
tagttgccat tggtatatga taagatgtac catcgataac caaggggcct ataacaccaa   1860
cgggcaaagg catgtaacct ataacatttt cacaacaagc gccaaatacg cggtcgtagt   1920
cataattttt atatggtaaa cgatcagatg ctaatacagg agcttctgcc aaaattgaaa   1980
gagccttcct acgtaccgca accgctctcg tagtatcacc taattttttc tccaaagcgt   2040
acaaaggtaa cttaccgtga ataaccaagg cagccgacct tttgttcttc aattgttttg   2100
tatttccact acttaataat gcttctaatt cttctaaagg acgtatttc ttatccaagc   2160 tttcaatatc gcgggaatca tcttcctcac tagatgatga aggtcctgat gagctcgatt   2220
gcgcagatga taaactttg actttcgatc cagaaatgac tgttttattg gttaaaactg   2280
gtgtagaagc cttttgtaca ggagcagtaa aagacttctt ggtgacttca gttttcacca   2340
attggtctgc agccattata gttttttctc cttgacgtta aagtatagag gtatattaac   2400 aatttttgt tgatactttt atgacatttg aataagaagt aatacaaacc gaaaatgttg   2460
aaagtattag ttaaagtggt tatgcagctt ttgcatttat atatctgtta atagatcaaa   2520
aatcatcgct tcgctgatta attaccccag aaataaggct aaaaaactaa tcgcattatt   2580
atcctatggt tgttaatttg attcgttgat ttgaaggttt gtggggccag gttactgcca   2640
atttttcctc ttcataacca taaaagctag tattgtagaa tctttattgt tcggagcagt   2700
gcggcgcgag gcacatctgc gtttcaggaa cgcgaccggt gaagaccagg acgcacggag   2760
gagagtcttc cgtcggaggg ctgtcgcccg ctcggcggct tctaatccgt acttcaatat   2820
agcaatgagc agttaagcgt attactgaaa gttccaaaga gaaggttttt ttaggctaag   2880
```

```
ataatggggc tctttacatt tccacaacat ataagtaaga ttagatatgg atatgtatat    2940
ggtggtattg ccatgtaata tgattattaa acttctttgc gtccatccaa aaaaaaagta    3000
agaattttg  aaaattcaat ataaatgact gccgacaaca atagtatgcc ccatggtgca    3060
gtatctagtt acgccaaatt agtgcaaaac caaacacctg aagacatttt ggaagagttt    3120
cctgaaatta ttccattaca acaaagacct aatacccgat ctagtgagac gtcaaatgac    3180
gaaagcggag aaacatgttt ttctggtcat gatgaggagc aaattaagtt aatgaatgaa    3240
aattgtattg ttttggattg ggacgataat gctattggtg ccggtaccaa gaaagtttgt    3300
catttaatgg aaaatattga aagggttta  ctacatcgtg cattctccgt ctttattttc    3360
aatgaacaag gtgaattact tttacaacaa agagccactg aaaaaataac tttccctgat    3420
cttttggacta acacatgctg ctctcatcca ctatgtattg atgacgaatt aggtttgaag    3480
ggtaagctag acgataagat taagggcgct attactgcgg cggtgagaaa actagatcat    3540
gaattaggta ttccagaaga tgaaactaag acaaggggta agtttcactt tttaaacaga    3600
atccattaca tggcaccaag caatgaacca tggggtgaac atgaaattga ttacatccta    3660
ttttataaga tcaacgctaa agaaaacttg actgtcaacc caaacgtcaa tgaagttaga    3720
gacttcaaat gggtttcacc aaatgatttg aaaactatgt ttgctgaccc aagttacaag    3780
tttacgcctt ggtttaagat tatttgcgag aattacttat tcaactgtgt ggagcaatta    3840
gatgaccttt ctgaagtgga aaatgacagg caaattcata gaatgctata caacgcgtc    3900
aataatatag gctacataaa aatcataata actttgttat catagcaaaa tgtgatataa    3960
aacgtttcat ttcacctgaa aaatagtaaa aataggcgac aaaaatcctt agtaatatgt    4020
aaactttatt ttctttattt acccgggagt cagtctgact cttgcgagag atgaggatgt    4080
aataatacta atctcgaaga tgccatctaa tacatataga catacatata tatatatata    4140
cattctatat attcttaccc agattctttg aggtaagacg gttgggtttt atcttttgca    4200
gttggtacta ttaagaacaa tcgaatcata agcattgctt acaaagaata cacatacgaa    4260
atattaacga taatgtcaat tacgaagact gaactggacg gtatattgcc attggtggcc    4320
agaggtaaag ttagagacat atatgaggta gacgctggta cgttgctgtt tgttgctacg    4380
gatcgtatct ctgcatatga cgttattatg gaaaacagca ttcctgaaaa ggggatccta    4440
ttgaccaaac tgtcagagtt ctggttcaag ttcctgtcca acgatgttcg taatcatttg    4500
gtcgacatcg ccccaggtaa gactattttc gattatctac ctgcaaaatt gagcgaacca    4560
aagtacaaaa cgcaactaga agaccgctct ctattggttc acaaacataa actaattcca    4620
ttggaagtaa ttgtcagagg ctacatcacc ggatctgctt ggaaagagta cgtaaaaaca    4680
ggtactgtgc atggtttgaa acaacctcaa ggacttaaag aatctcaaga gttcccagaa    4740
ccaatcttca ccccatcgac caaggctgaa caaggtgaac atgacgaaaa catctctcct    4800
gcccaggccg ctgagctggt gggtgaagat ttgtcacgta gagtggcaga actggctgta    4860
aaactgtact ccaagtgcaa agattatgct aaggagaagg gcatcatcat cgcagacact    4920
aaattgttta aac                                                      4933
```

<210> SEQ ID NO 12
<211> LENGTH: 6408
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
gtttaaacta ttgtgagggt cagttatttc atccagatat aacccgagag gaaacttctt      60
agcgtctgtt ttcgtaccat aaggcagttc atgaggtata ttttcgttat tgaagcccag     120
ctcgtgaatg cttaatgctg ctgaactggt gtccatgtcg cctaggtacg caatctccac     180
aggctgcaaa ggttttgtct caagagcaat gttattgtgc accccgtaat tggtcaacaa     240
gtttaatctg tgcttgtcca ccagctctgt cgtaaccttc agttcatcga ctatctgaag     300
aaatttacta ggaatagtgc catggtacag caaccgagaa tggcaatttc tactcgggtt     360
cagcaacgct gcataaacgc tgttggtgcc gtagacatat tcgaagatag gattatcatt     420
cataagtttc agagcaatgt ccttattctg gaacttggat ttatggctct tttggtttaa     480
tttcgcctga ttcttgatct cctttagctt ctcgacgtgg gccttttct tgccatatgg      540
atccgctgca cggtcctgtt ccctagcatg tacgtgagcg tatttccttt taaaccacga     600
cgctttgtct tcattcaacg tttcccattg tttttttcta ctattgcttt gctgtgggaa     660
aaacttatcg aaagatgacg actttttctt aattctcgtt ttaagagctt ggtgagcgct     720
aggagtcact gccaggtatc gtttgaacac ggcattagtc agggaagtca taacacagtc     780
cttttcccgca attttctttt tctattactc ttggcctcct ctagtacact ctatattttt     840
ttatgcctcg gtaatgattt tcattttttt tttttccacc tagcggatga ctcttttttt     900
ttcttagcga ttggcattat cacataatga attatacatt atataaagta atgtgatttc     960
ttcgaagaat atactaaagt ttagcttgcc tcgtccccgc cgggtcaccc ggccagcgac    1020
atggaggccc agaataccct ccttgacagt cttgacgtgc gcagctcagg ggcatgatgt    1080
gactgtcgcc cgtacattta gcccatacat ccccatgtat aatcatttgc atccatacat    1140
tttgatggcc gcacggcgcg aagcaaaaat tacggctcct cgctgcagac ctgcgagcag    1200
ggaaacgctc ccctcacaga cgcgttgaat tgtccccacg ccgcgcccct gtagagaaat    1260
ataaaaggtt aggatttgcc actgaggttc ttctttcata tacttccttt taaaatcttg    1320
ctaggataca gttctcacat cacatccgaa cataaacaac catggcagaa ccagcccaaa    1380
aaaagcaaaa acaaactgtt caggagcgca aggcgtttat ctcccgtatc actaatgaaa    1440
ctaaaattca aatcgctatt tcgctgaatg gtggttatat tcaaataaaa gattcgattc    1500
ttcctgcaaa gaaggatgac gatgtagctt cccaagctac tcagtcacag gtcatcgata    1560
ttcacacagg tgttggcttt ttggatcata tgatccatgc gttggcaaaa cactctggtt    1620
ggtctcttat tgttgaatgt attggtgacc tgcacattga cgatcaccat actaccgaag    1680
attgcggtat cgcattaggg caagcgttca agaagcaat gggtgctgtc cgtggtgtaa    1740
aaagattcgg tactgggttc gcaccattgg atgaggcgct atcacgtgcc gtagtcgatt    1800
tatctagtag accatttgct gtaatcgacc ttggattgaa gagagagatg attggtgatt    1860
tatccactga aatgattcca cacttttttgg aaagtttcgc ggaggcggcc agaattactt    1920
tgcatgttga ttgtctgaga ggtttcaacg atcaccacag aagtgagagt gcgttcaagg    1980
ctttggctgt tgccataaga gaagctattt ctagcaatgg caccaatgac gttccctcaa    2040
ccaaaggtgt tttgatgtga agtactgaca ataaaaagat tcttgttttc aagaacttgt    2100
catttgtata gttttttat attgtagttg ttctattta atcaaatgtt agcgtgattt      2160
atattttttt tcgcctcgac atcatctgcc cagatgcgaa gttaagtgcg cagaaagtaa    2220
tatcatgcgt caatcgtatg tgaatgctgg tcgctatact gctgtcgatt cgatactaac    2280
gccgccatcc acccgggatg gtctgcttaa atttcattct gtcttcgaaa gctgaattga    2340
tactacgaaa aatttttttt tgtttctctt tctatcttta ttacataaaa cttcatacac    2400
```

```
agttaagatt aaaaacaact aataaataat gcctatcgca aattagctta tgaagtccat    2460
ggtaaattcg tgtttcctgg caataataga tcgtcaattt gttgctttgt ggtagtttta    2520
ttttcaaata attggaatac tagggatttg atttaagat ctttattcaa attttttgcg     2580
cttaacaaac agcagccagt cccacccaag tctgtttcaa atgtctcgta actaaaatca    2640
tcttgcaatt tcttttgaa actgtcaatt tgctcttgag taatgtctct tcgtaacaaa     2700
gtcaaagagc aaccgccgcc accagcaccg gtaagttttg tggagccaat tctcaaatca    2760
tcgctcagat ttttaataag ttctaatcca ggatgagaaa caccgattga gacaagcagt    2820
ccatgattta ttcttatcaa ttccaatagt tgttcataca gttcattatt agtttctaca    2880
gcctcgtcat cggtgccttt acatttactt aacttagtca tgatctctaa gccttgtagg    2940
gcacattcac ccatggcatc tagaattggc ttcataactt caggaaattt ctcggtgacc    3000
aacacacgaa cgcgagcaac aagatctttt gtagaccttg gaattctagt ataggttagg    3060
atcattggaa tggctgggaa atcatctaag aacttaaaat tgtttgtgtt tattgttcca    3120
ttatgtgagt cttttcaaa tagcagggca ttaccataag tggccacagc gttatctatt     3180
cctgaagggg taccgtgaat acacttttca cctatgaagg cccattgatt cactatatgc    3240
ttatcgtttt ctgacagctt ttccaagtca ttagatccta ttaaccccc caagtaggcc     3300 atagctaagg ccagtgatac agaaatagag gcgcttgagc ccaacccagc accgatgggt    3360
aaagtagact ttaagaaaaa cttaatattc ttggcatggg ggcataggca acaaacata     3420 tacaggaaac aaaacgctgc atggtagtgg aaggattcgg atagttgagc taacaacgga    3480
tccaaaagac taacgagttc ctgagacaag ccatcggtgg cttgttgagc cttggccaat    3540
ttttgggagt ttacttgatc ctcggtgatg gcattgaaat cattgatgga ccacttatga    3600
ttaaagctaa tgtccgggaa gtccaattca atagtatctg gtgcagatga ctcgcttatt    3660
agcaggtagg ttctcaacgc agacacacta gcagcgacgg caggcttgtt gtacacagca    3720
gagtgttcac caaaaataat aacctttccc ggtgcagaag ttaagaacgg taatgacatt    3780
atagtttttt ctccttgacg ttaaagtata gaggtatatt aacaattttt tgttgatact    3840
tttatgacat ttgaataaga agtaatacaa accgaaaatg ttgaaagtat tagttaaagt    3900
ggttatgcag cttttgcatt tatatatctg ttaatagatc aaaaatcatc gcttcgctga    3960
ttaattaccc cagaaataag gctaaaaaac taatcgcatt attatcctat ggttgttaat    4020
ttgattcgtt gatttgaagg tttgtggggc caggttactg ccaattttc ctcttcataa     4080 ccataaaagc tagtattgta gaatctttat tgttcggagc agtgcggcgc gaggcacatc    4140
tgcgtttcag gaacgcgacc ggtgaagacc aggacgcacg gaggagagtc ttccgtcgga    4200
gggctgtcgc ccgctcggcg gcttctaatc cgtacttcaa tatagcaatg agcagttaag    4260
cgtattactg aaagttccaa agagaaggtt ttttaggct aagataatgg ggctctttac     4320
atttccacaa catataagta agattagata tggatatgta tatggtggta ttgccatgta    4380
atatgattat taaacttctt tgcgtccatc caaaaaaaa gtaagaattt ttgaaaattc     4440
aatataaatg tctcagaacg tttacattgt atcgactgcc agaaccccaa ttggttcatt    4500
ccagggttct ctatcctcca agacagcagt ggaattgggt gctgttgctt taaaaggcgc    4560
cttggctaag gttccagaat tggatgcatc caaggatttt gacgaaatta tttttggtaa    4620
cgttctttct gccaatttgg gccaagctcc ggccagacaa gttgctttgg ctgccggttt    4680
gagtaatcat atcgttgcaa gcacagttaa caaggtctgt gcatccgcta tgaaggcaat    4740 catttgggt gctcaatcca tcaaatgtgg taatgctgat gttgtcgtag ctggtggttg     4800
```

```
tgaatctatg actaacgcac catactacat gccagcagcc cgtgcgggtg ccaaatttgg    4860
ccaaactgtt cttgttgatg gtgtcgaaag agatgggttg aacgatgcgt acgatggtct    4920
agccatgggt gtacacgcag aaaagtgtgc ccgtgattgg gatattacta gagaacaaca    4980
agacaatttt gccatcgaat cctaccaaaa atctcaaaaa tctcaaaagg aaggtaaatt    5040
cgacaatgaa attgtacctg ttaccattaa gggatttaga ggtaagcctg atactcaagt    5100
cacgaaggac gaggaacctg ctagattaca cgttgaaaaa ttgagatctg caaggactgt    5160
tttccaaaaa gaaaacggta ctgttactgc cgctaacgct tctccaatca acgatggtgc    5220
tgcagccgtc atcttggttt ccgaaaaagt tttgaaggaa aagaatttga agcctttggc    5280
tattatcaaa ggttggggtg aggccgctca tcaaccagct gattttacat gggctccatc    5340
tcttgcagtt ccaaaggctt tgaaacatgc tggcatcgaa gacatcaatt ctgttgatta    5400
ctttgaattc aatgaagcct tttcggttgt cggtttggtg aacactaaga ttttgaagct    5460
agacccatct aaggttaatg tatatggtgg tgctgttgct ctaggtcacc cattgggttg    5520
ttctggtgct agagtggttg ttacactgct atccatctta cagcaagaag gaggtaagat    5580
cggtgttgcc gccatttgta atggtggtgg tggtgcttcc tctattgtca ttgaaaagat    5640
atgattacgt tctgcgattt tctcatgatc tttttcataa aatacataaa tatataaatg    5700
gctttatgta taacaggcat aatttaaagt tttatttgcg attcatcgtt tttcaggtac    5760
tcaaacgctg aggtgtgcct tttgacttac ttttcccggg agaggctagc agaattaccc    5820
tccacgttga ttgtctgcga ggcaagaatg atcatcaccg tagtgagagt gcgttcaagg    5880
ctcttgcggt tgccataaga gaagccacct cgcccaatgg taccaacgat gttccctcca    5940
ccaaaggtgt tctatgtag tgacaccgat tatttaaagc tgcagcatac gatatatata    6000
catgtgtata tatgtatacc tatgaatgtc agtaagtatg tatacgaaca gtatgatact    6060
gaagatgaca agtaatgca tcattctata cgtgtcattc tgaacgaggc gcgctttcct    6120 ttttctttt tgcttttct ttttttttct cttgaactcg agaaaaaaaa tataaaagag    6180
atggaggaac gggaaaaagt tagttgtggt gataggtggc aagtggtatt ccgtaagaac    6240
aacaagaaaa gcatttcata ttatggctga actgagcgaa caagtgcaaa atttaagcat    6300
caacgacaac aacgagaatg gttatgttcc tcctcactta agaggaaaac caagaagtgc    6360
cagaaataac agtagcaact acaataacaa caacggcggc gtttaaac              6408

<210> SEQ ID NO 13
<211> LENGTH: 6087
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gtttaaactt ttccaatagg tggttagcaa tcgtcttact ttctaacttt tcttaccttt      60
tacatttcag caatatatat atatatattt caaggatata ccattctaat gtctgcccct     120
aagaagatcg tcgttttgcc aggtgaccac gttggtcaag aaatcacagc cgaagccatt     180
aaggttctta agctatttc tgatgttcgt tccaatgtca agttcgattt cgaaaatcat     240
ttaattggtg gtgctgctat cgatgctaca ggtgttccac ttccagatga ggcgctggaa     300
gcctccaaga aggctgatgc cgttttgtta ggtgctgtgg gtggtcctaa atgggggtacc     360 ggtagtgtta gacctgaaca aggttactaa aaaatccgta agaacttca attgtacgcc     420
```

```
aacttaagac catgtaactt tgcatccgac tctcttttag acttatctcc aatcaagcca    480
caatttgcta aaggtactga cttcgttgtt gtcagagaat tagtgggagg tatttacttt    540
ggtaagagaa aggaagacgt ttagcttgcc tcgtccccgc cgggtcaccc ggccagcgac    600
atggaggccc agaataccct ccttgacagt cttgacgtgc gcagctcagg ggcatgatgt    660
gactgtcgcc cgtacattta gcccatacat ccccatgtat aatcatttgc atccatacat    720
tttgatggcc gcacggcgcg aagcaaaaat tacggctcct cgctgcagac ctgcgagcag    780
ggaaacgctc ccctcacaga cgcgttgaat tgtccccacg ccgcgcccct gtagagaaat    840
ataaaaggtt aggatttgcc actgaggttc ttctttcata tacttccttt taaaatcttg    900
ctaggataca gttctcacat cacatccgaa cataaacaac catggcagaa ccagcccaaa    960
aaaagcaaaa acaaactgtt caggagcgca aggcgtttat ctcccgtatc actaatgaaa   1020
ctaaaattca aatcgctatt tcgctgaatg gtggttatat tcaaataaaa gattcgattc   1080
ttcctgcaaa gaaggatgac gatgtagctt cccaagctac tcagtcacag gtcatcgata   1140
ttcacacagg tgttggcttt ttggatcata tgatccatgc gttggcaaaa cactctggtt   1200
ggtctcttat tgttgaatgt attggtgacc tgcacattga cgatcaccat actaccgaag   1260
attgcggtat cgcattaggg caagcgttca aagaagcaat gggtgctgtc cgtggtgtaa   1320
aaagattcgg tactgggttc gcaccattgg atgaggcgct atcacgtgcc gtagtcgatt   1380
tatctagtag accatttgct gtaatcgacc ttggattgaa gagagagatg attggtgatt   1440
tatccactga aatgattcca cacttttttgg aaagtttcgc ggaggcggcc agaattactt   1500
tgcatgttga ttgtctgaga ggtttcaacg atcaccacag aagtgagagt gcgttcaagg   1560
ctttggctgt tgccataaga gaagctattt ctagcaatgg caccaatgac gttccctcaa   1620
ccaaaggtgt tttgatgtga agtactgaca ataaaaagat tcttgttttc aagaacttgt   1680
catttgtata gtttttttat attgtagttg ttctatttta atcaaatgtt agcgtgattt   1740 atatttttt tcgcctcgac atcatctgcc cagatgcgaa gttaagtgcg cagaaagtaa   1800
tatcatgcgt caatcgtatg tgaatgctgg tcgctatact gctgtcgatt cgatactaac   1860
gccgccatcc acccgggttt ctcattcaag tggtaactgc tgttaaaatt aagatattta   1920
taaattgaag cttggtcgtt ccgaccaata ccgtagggaa acgtaaatta gctattgtaa   1980
aaaaaggaaa agaaaagaaa agaaaaatgt tacatatcga attgatctta ttcctttggt   2040
agaccagtct ttgcgtcaat caaagattcg tttgtttctt gtgggcctga accgacttga   2100
gttaaaatca ctctggcaac atccttttgc aactcaagat ccaattcacg tgcagtaaag   2160
ttagatgatt caaattgatg gttgaaagcc tcaagctgct cagtagtaaa tttcttgtcc   2220
catccaggaa cagagccaaa caatttatag ataaatgcaa agagtttcga ctcatttttca   2280 gctaagtagt acaacacagc atttggacct gcatcaaacg tgtatgcaac gattgtttct   2340
ccgtaaaact gattaatggt gtggcaccaa ctgatgatac gcttggaagt gtcattcatg   2400
tagaatattg gagggaaaga gtccaaacat gtggcatgga aagagttgga atccatcatt   2460
gtttcctttg caaaggtggc gaaatctttt tcaacaatgg ctttacgcat gacttcaaat   2520
ctctttggta cgacatgttc aattctttct ttaaatagtt cggaggttgc cacggtcaat   2580
tgcataccct gagtggaact cacatccttt ttaatatcgc tgacaactag gacacaagct   2640
ttcatctgag gccagtcaga gctgtctgcg atttgtactg ccatggaatc atgaccatct   2700
tcagcttttc ccatttccca ggccacgtat ccgccaaaca acgatctaca agctgaacca   2760
gacccctttc ttgctattct agatatttct gaagttgact gtggtaattg gtataactta   2820
```

-continued

```
gcaattgcag agaccaatgc agcaaagcca gcagcggagg aagctaaacc agctgctgta    2880
ggaaagttat tttcggagac aatgtggagt ttccattgag ataatgtggg caatgaggcg    2940
tccttcgatt ccatttcctt tcttaattgg cgtaggtcgc gcagacaatt ttgagttctt    3000
tcattgtcga tgctgtgtgg ttctccattt aaccacaaag tgtcgcgttc aaactcaggt    3060
gcagtagccg cagaggtcaa cgttctgagg tcatcttgcg ataaagtcac tgatatggac    3120
gaattggtgg gcagattcaa cttcgtgtcc cttttccccc aatacttaag ggttgcgatg    3180
ttgacgggtg cggtaacgga tgctgtgtaa acggtcatta tagtttttc tccttgacgt     3240 taaagtatag aggtatatta acaatttttt gttgatactt ttatgacatt tgaataagaa    3300
gtaatacaaa ccgaaaatgt tgaaagtatt agttaaagtg gttatgcagc ttttgcattt    3360
atatatctgt taatagatca aaaatcatcg cttcgctgat taattacccc agaaataagg    3420
ctaaaaaact aatcgcatta ttatcctatg gttgttaatt tgattcgttg atttgaaggt    3480
ttgtggggcc aggttactgc caattttcc tcttcataac cataaaagct agtattgtag     3540
aatctttatt gttcggagca gtgcggcgcg aggcacatct gcgtttcagg aacgcgaccg    3600
gtgaagacca ggacgcacgg aggagagtct ccgtcggag gctgtcgcc cgctcggcgg      3660 cttctaatcc gtacttcaat atagcaatga gcagttaagc gtattactga aagttccaaa    3720
gagaaggttt ttttaggcta agataatggg gctctttaca tttccacaac atataagtaa    3780
gattagatat ggatatgtat atggtggtat tgccatgtaa tatgattatt aaacttcttt    3840
gcgtccatcc aaaaaaaaag taagaatttt tgaaaattca atataaatgt cagagttgag    3900
agccttcagt gccccaggga aagcgttact agctggtgga tatttagttt tagatccgaa    3960
atatgaagca tttgtagtcg gattatcggc aagaatgcat gctgtagccc atccttacgg    4020
ttcattgcaa gagtctgata gtttgaagt gcgtgtgaaa agtaaacaat ttaaagatgg     4080
ggagtggctg taccatataa gtcctaaaac tggcttcatt cctgtttcga taggcggatc    4140
taagaaccct ttcattgaaa aagttatcgc taacgtatt agctactta agcctaacat      4200 ggacgactac tgcaatagaa acttgttcgt tattgatatt ttctctgatg atgcctacca    4260
ttctcaggag gacagcgtta ccgaacatcg tggcaacaga agattgagtt ttcattcgca    4320
cagaattgaa gaagttccca aaacagggct gggctcctcg gcaggtttag tcacagtttt    4380
aactacagct ttggcctcct tttttgtatc ggacctggaa aataatgtag acaaatatag    4440
agaagttatt cataatttat cacaagttgc tcattgtcaa gctcagggta aaattggaag    4500
cgggtttgat gtagcggcgg cagcatatgg atctatcaga tatagaagat tcccacccgc    4560
attaatctct aatttgccag atattggaag tgctacttac ggcagtaaac tggcgcattt    4620
ggttaatgaa gaagactgga atataacgat taaagtaac catttaccttt cgggattaac   4680 tttatggatg ggcgatatta agaatggttc agaaacagta aaactggtcc agaaggtaaa   4740
aaattggtat gattcgcata tgccggaaag cttgaaaata tatacagaac tcgatcatgc    4800
aaattctaga tttatggatg gactatctaa actagatcgc ttacacgaga ctcatgacga    4860
ttacagcgat cagatatttg agtctcttga gaggaatgac tgtacctgtc aaaagtatcc    4920
tgagatcaca gaagttagag atgcagttgc cacaattaga cgttccttta gaaaaataac    4980
taaagaatct ggtgccgata tcgaacctcc cgtacaaact agcttattgg atgattgcca    5040
gaccttaaaa ggagttctta cttgcttaat acctggtgct ggtggttatg acgccattgc    5100
agtgattgct aagcaagatg ttgatcttag ggctcaaacc gctgatgaca aaagattttc    5160
taaggttcaa tggctggatg taactcaggc tgactggggt gttaggaaag aaaaagatcc    5220
```

| | |
|---|---|
| ggaaacttat cttgataaat aacttaaggt agataatagt ggtccatgtg acatctttat | 5280 |
| aaatgtgaag tttgaagtga ccgcgcttaa catctaacca ttcatcttcc gatagtactt | 5340 |
| gaaattgttc ctttcggcgg catgataaaa ttcttttaat gggtacaagc tacccgggcc | 5400 |
| cgggaaagat tctctttttt tatgatattt gtacataaac tttataaatg aaattcataa | 5460 |
| tagaaacgac acgaaattac aaaatggaat atgttcatag ggtagacgaa actatatacg | 5520 |
| caatctacat acatttatca agaaggagaa aaaggaggta gtaaaggaat acaggtaagc | 5580 |
| aaattgatac taatggctca acgtgataag gaaaagaat tgcactttaa cattaatatt | 5640 |
| gacaaggagg agggcaccac acaaaaagtt aggtgtaaca gaaaatcatg aaactatgat | 5700 |
| tcctaattta tatattggag gattttctct aaaaaaaaaa aaatacaaca aataaaaaac | 5760 |
| actcaatgac ctgaccattt gatggagttt aagtcaatac cttcttgaac catttcccat | 5820 |
| aatggtgaaa gttccctcaa gaattttact ctgtcagaaa cggccttaac gacgtagtcg | 5880 |
| acctcctctt cagtactaaa tctaccaata ccaaatctga tggaagaatg ggctaatgca | 5940 |
| tcatccttac ccagcgcatg taaaacataa gaaggttcta gggaagcaga tgtacaggct | 6000 |
| gaacccgagg ataatgcgat atcccttagt gccatcaata aagattctcc ttccacgtag | 6060 |
| gcgaaagaaa cgttaacacg tttaaac | 6087 |

<210> SEQ ID NO 14
<211> LENGTH: 2733
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

| | |
|---|---|
| gtaaaacgac ggccagtatt aaccctcact aaagggaact cgaggctctt caaggcgcg | 60 |
| ccacggtcgt gcggattggc agactccata tgctatgcgg catcagagca gattgtactg | 120 |
| agagtgcacc atatgcggtg tgaaataccg cacagatgcg taaggagaaa ataccgcatc | 180 |
| aggcgccatt cgccattcag gctgcgcaac tgttgggaag ggcgatcggt gcgggcctct | 240 |
| tcgctattac gccagctggc gaaaggggga tgtgctgcaa ggcgattaag ttgggtaacg | 300 |
| ccagggtttt cccagtcacg acgttgtaaa acgacggcca gtgaattcga gctcggtacc | 360 |
| cggggatcct ctagcgtcga cctgcaggca tgcaagcttg gcgtaatcat ggtcatagct | 420 |
| gtttcctgtg tgaaattgtt atccgctcac aattccacac aacatacgag ccggaagcat | 480 |
| aaagtgtaaa gcctggggtg cctaatgagt gagctaactc acattaattg cgttgcgcgc | 540 |
| tagcgagtca tccaagcccc tcagcccccc tagcgtcgtg aagagcgagc tcccgctgag | 600 |
| caataactag cgtcatagct gtttcctggg tcgttcggct gcggcgagcg gtatcagctc | 660 |
| actcaaaggc ggtaatacgg ttatccacag aatcagggga taacgcagga agaacatgt | 720 |
| gagcaaaagg ccagcaaaag gccaggaacc gtaaaaaggc cgcgttgctg gcgttttcc | 780 |
| ataggctccg ccccccctgac gagcatcaca aaaatcgacg ctcaagtcag aggtggcgaa | 840 |
| acccgacagg actataaaga taccaggcgt ttccccctgg aagctccctc gtgcgctctc | 900 |
| ctgttccgac cctgccgctt acccgatacc tgtccgcctt ctcccttcg ggaagcgtgg | 960 |
| cgctttctca tagctcacgc tgtaggtatc tcagttcggt gtaggtcgtt cgctccaagc | 1020 |
| tgggctgtgt gcacgaaccc cccgttcagc ccgaccgctg cgccttatcc ggtaactatc | 1080 |
| gtcttgattc caacccggta agacacgact tatcgccact ggcagcagcc actggtaaca | 1140 |
| ggattagcag agcgaggtat gtaggcggtg ctacagagtt cttgaagtgg tggcctaact | 1200 |

```
acggctacac tagaagaaca gtatttggta tctgcgctct gctgaagcca gttaccttcg    1260
gaaaaagagt tggtagctct tgatccggca aacaaaccac cgctggtagc ggtggttttt    1320
ttgtttgcaa gcagcagatt acgcgcagaa aaaaggatc tcaagaagat cctttgatct    1380
tttctacggg gtctgacgct cagtggaacg aaaactcacg ttaagggatt ttggtcatga    1440
gattatcaaa aaggatcttc acctagatcc ttttaaatta aaaatgaagt tttaaatcaa    1500
tctaaagtat atatgagtaa cttggtcgca tgcttaccaa tgcttaatca gtgaggcacc    1560
tatctcagcg atctgtctat ttcgttcatc catagttgcc tgactgcccg tcgtgtagat    1620
aactacgata cgggagggct taccatctgg ccccagtgct gcaatgatac cgcgagaccc    1680
acgctcaccg gctccagatt tatcagcaat aaaccagcca gccggaaggg ccgagcgcag    1740
aagtggtcct gcaactttat ccgcctccat ccagtctatt aattgttgcc gggaagctag    1800
agtaagtagt tcgccagtta atagtttgcg caacgttgtt gccattgcta caggcatcgt    1860
ggtgtcacgc tcgtcgtttg gtatggcttc attcagctcc ggttcccaac gatcaaggcg    1920
agttacatga tcccccatgt tgtgcaaaaa agcggttagc tccttcggtc ctccgatcgt    1980
tgtcagaagt aagttggccg cagtgttatc actcatggtt atggcagcac tgcataattc    2040
tcttactgtc atgccatccg taagatgctt ttctgtgact ggtgagtact caaccaagtc    2100
attctgagaa tagtgtatgc ggcgaccgag ttgctcttgc ccggcgtcaa tacgggataa    2160
taccgcgcca catagcagaa ctttaaaagt gctcatcatt ggaaaacgtt cttcggggcg    2220
aaaactctca aggatcttac cgctgttgag atccagttcg atgtaaccca ctcgtgcacc    2280
caactgatct tcagcatctt ttactttcac cagcgtttct gggtgagcaa aaacaggaag    2340
gcaaaatgcc gcaaaaaagg gaataagggc gacacgaaaa tgttgaatac tcatcaattg    2400 ccttttcaa tattattgaa gcatttatca gggttattgt ctcatgagcg gttacatatt    2460
tgaatgtatt tagaaaaata aacaataggg gttccgcgc acatttcccc gaaaagtgcc    2520
acctgacgtc taagaaacca ttattatcat gacattaacc tataaaaata ggcgtatcac    2580
gaggcccttt catctcgcgc gtttcggtga tgacggtgaa aacctctgac acatgcagct    2640
cccggagaca gtcacagctt gtctgtaagc ggatgccggg agcagacaag cccgtcaggg    2700
cgcgtcagcg ggtgttggcg ggtgtcgggg ctg                                 2733
```

<210> SEQ ID NO 15
<211> LENGTH: 4170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
ggtcgttcgg ctgcggcgag cggtatcagc tcactcaaag gcggtaatac ggttatccac      60
agaatcaggg gataacgcag gaaagaacat gtgagcaaaa ggccagcaaa aggccaggaa     120
ccgtaaaaag gccgcgttgc tggcgttttt ccataggctc cgcccccctg acgagcatca     180
caaaaatcga cgctcaagtc agaggtggcg aaacccgaca ggactataaa gataccaggc     240
gtttccccct ggaagctccc tcgtgcgctc tcctgttccg accctgccgc ttaccggata     300
cctgtccgcc tttctccctt cgggaagcgt ggcgctttct catagctcac gctgtaggta     360
tctcagttcg gtgtaggtcg ttcgctccaa gctgggctgt gtgcacgaac cccccgttca     420
gcccgaccgc tgcgccttat ccggtaacta tcgtcttgtg tccaacccgg taagacacga     480
```

-continued

```
cttatcgcca ctggcagcag ccactggtaa caggattagc agagcgaggt atgtaggcgg      540
tgctacagag ttcttgaagt ggtggcctaa ctacggctac actagaagaa cagtatttgg      600
tatctgcgct ctgctgaagc cagttacctt cggaaaaaga gttggtagct cttgatccgg      660
caaacaaacc accgctggta gcggtggttt tttgtttgc aagcagcaga ttacgcgcag        720
aaaaaaagga tctcaagaag atcctttgat cttttctacg gggtctgacg ctcagtggaa      780
cgaaaactca cgttaaggga ttttggtcat gagattatca aaaaggatct tcacctagat      840
ccttttaaat taaaaatgaa gttttaaatc aatctaaagt atatatgagt aaacttggtc      900
gcatgcttac caatgcttaa tcagtgaggc acctatctca gcgatctgtc tatttcgttc      960
atccatagtt gcctgactgc ccgtcgtgta gataactacg atacgggagg gcttaccatc     1020
tggccccagt gctgcaatga taccgcgaga cccacgctca ccggctccag atttatcagc     1080
aataaaccag ccagccggaa gggccgagcg cagaagtggt cctgcaactt tatccgcctc     1140
catccagtct attaattgtt gccgggaagc tagagtaagt agttcgccag ttaatagttt     1200
gcgcaacgtt gttgccattg ctacaggcat cgtggtgtca cgctcgtcgt ttggtatggc     1260
ttcattcagc tccggttccc aacgatcaag gcgagttaca tgatccccca tgttgtgcaa     1320
aaaagcggtt agctccttcg gtcctccgat cgttgtcaga agtaagttgg ccgcagtgtt     1380
atcactcatg gttatggcag cactgcataa ttctcttact gtcatgccat ccgtaagatg     1440
cttttctgtg actggtgagt actcaaccaa gtcattctga atagtgta tgcggcgacc       1500 gagttgctct tgcccggcgt caatacggga taataccgcg ccacatagca gaactttaaa     1560
agtgctcatc attggaaaac gttcttcggg gcgaaaactc tcaaggatct taccgctgtt     1620
gagatccagt tcgatgtaac ccactcgtgc acccaactga tcttcagcat cttttacttt     1680
caccagcgtt tctgggtgag caaaaacagg aaggcaaaat gccgcaaaaa agggaataag     1740
ggcgacacgg aaatgttgaa tactcatcaa ttgccttttt caatattatt gaagcattta     1800
tcagggttat tgtctcatga gcggttacat atttgaatgt atttagaaaa ataaacaaat     1860
aggggttccg cgcacatttc cccgaaaagt gccacctgac gtctaagaaa ccattattat     1920
catgacatta acctataaaa ataggcgtat cacgaggccc tttcatctcg cgcgtttcgg     1980
tgatgacggt gaaaacctct gacacatgca gctcccggag acagtcacag cttgtctgta     2040
agcggatgcc gggagcagac aagcccgtca gggcgcgtca gcgggtgttg gcgggtgtcg     2100
gggctggtaa aacgacggcc agtattaacc ctcactaaag ggaactcgag gctcttcagc     2160
tcacacgcgc ccaggggag ccttcgacac tagtaataca catcatcgtc ctacaagttc      2220
atcaaagtgt tggacagaca actataccag catggatctc ttgtatcggt tcttttctcc     2280
cgctctctcg caataacaat gaacactggg tcaatcatag cctacacagg tgaacagagt     2340
agcgtttata cagggtttat acggtgattc ctacggcaaa aattttcat ttctaaaaaa      2400 aaaaagaaaa atttttcttt ccaacgctag aaggaaaaga aaatctaat taaattgatt     2460 tggtgatttt ctgagagttc ccttttcat atatcgaatt ttgaatataa aaggagatcg    2520
aaaaaatttt tctattcaat ctgttttctg gttttatttg atagtttttt tgtgtattat   2580
tattatggat tagtactggt ttatatgggt ttttctgtat aacttctttt tattttagtt  2640
tgtttaatct tattttgagt tacattatag ttccctaact gcaagagaag taacattaaa   2700
aatgaaaaag cctgaactca ccgcgacgtc tgtcgagaag tttctgatcg aaaagttcga   2760
cagcgtctcc gacctgatgc agctctcgga gggcgaagaa tctcgtgctt tcagcttcga   2820
tgtaggaggg cgtggatatg tcctgcgggt aaatagctgc gccgatggtt tctacaaaga   2880
```

```
tcgttatgtt tatcggcact ttgcatcggc cgcgctcccg attccggaag tgcttgacat   2940
tggggaattc agcgagagcc tgacctattg catctcccgc cgtgcacagg gtgtcacgtt   3000
gcaagacctg cctgaaaccg aactgcccgc tgttctgcag ccggtcgcgg aggccatgga   3060
tgcgatcgct gcggccgatc ttagccagac gagcgggttc ggcccattcg gaccgcaagg   3120
aatcggtcaa tacactacat ggcgtgattt catatgcgcg attgctgatc cccatgtgta   3180
tcactggcaa actgtgatgg acgacaccgt cagtgcgtcc gtcgcgcagg ctctcgatga   3240
gctgatgctt tgggccgagg actgccccga agtccggcac ctcgtgcacg cggatttcgg   3300
ctccaacaat gtcctgacgg acaatggccg cataacagcg gtcattgact ggagcgaggc   3360
gatgttcggg gattcccaat acgaggtcgc caacatcttc ttctggaggc cgtggttggc   3420
ttgtatggag cagcagacgc gctacttcga gcggaggcat ccggagcttg caggatcgcc   3480
gcggctccgg gcgtatatgc tccgcattgg tcttgaccaa ctctatcaga gcttggttga   3540
cggcaatttc gatgatgcag cttgggcgca ggtcgatgc gacgcaatcg tccgatccgg   3600
agccgggact gtcgggcgta cacaaatcgc ccgcagaagc gcggccgtct ggaccgatgg   3660
ctgtgtagaa gtactcgccg atagtggaaa ccgacgcccc agcactcgtc cgagggcaaa   3720
ggaataggtt taacttgata ctactagatt ttttctcttc atttataaaa tttttggtta   3780
taattgaagc tttagaagta tgaaaaaatc ctttttttc attctttgca accaaaataa    3840
gaagcttctt ttattcattg aaatgatgaa tataaaccta acaaagaaa aagactcgaa    3900 tatcaaacat taaaaaaaaa taaaagaggt tatctgtttt cccatttagt tggagtttgc   3960
attttctaat agatagaact ctcaattaat gtggatttag tttctctgtt cgttttttt    4020 tgttttgttc tcactgtatt tacatttcta tttagtattt agttattcat ataatcttaa   4080
cttctcgagg agctctcgct cgtccaacgc cggcggacct tgaagagcga gctcccgctg   4140
agcaataact agcgtcatag ctgtttcctg                                    4170
```

<210> SEQ ID NO 16
<211> LENGTH: 2519
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
ggtcgttcgg ctgcggcgag cggtatcagc tcactcaaag gcggtaatac ggttatccac     60
agaatcaggg gataacgcag gaaagaacat gtgagcaaaa ggccagcaaa aggccaggaa    120
ccgtaaaaag gccgcgttgc tggcgttttt ccataggctc cgcccccctg acgagcatca    180
caaaaatcga cgctcaagtc agaggtggcg aaacccgaca ggactataaa gataccaggc    240
gtttccccct ggaagctccc tcgtgcgctc tcctgttccg accctgccgc ttacccgata    300
cctgtccgcc tttctccctt cgggaagcgt ggcgctttct catagctcac gctgtaggta    360
tctcagttcg gtgtaggtcg ttcgctccaa gctgggctgt gtgcacgaac cccccgttca    420
gcccgaccgc tgcgccttat ccggtaacta tcgtcttgtg tccaacccgg taagacacga    480
cttatcgcca ctggcagcag ccactggtaa caggattagc agagcgaggt atgtaggcgg    540
tgctacagag ttcttgaagt ggtggcctaa ctacggctac actagaagaa cagtatttgg    600
tatctgcgct ctgctgaagc cagttacctt cggaaaaaga gttggtagct cttgatccgg    660
caaacaaacc accgctggta gcggtggttt ttttgtttgc aagcagcaga ttacgcgcag    720
aaaaaaagga tctcaagaag atcctttgat cttttctacg gggtctgacg ctcagtggaa    780
```

| | |
|---|---|
| cgaaaactca cgttaaggga ttttggtcat gagattatca aaaaggatct tcacctagat | 840 |
| ccttttaaat taaaaatgaa gttttaaatc aatctaaagt atatatgagt aaacttggtc | 900 |
| gcatgcttac caatgcttaa tcagtgaggc acctatctca gcgatctgtc tatttcgttc | 960 |
| atccatagtt gcctgactgc ccgtcgtgta gataactacg atacgggagg gcttaccatc | 1020 |
| tggcccccagt gctgcaatga taccgcgaga cccacgctca ccggctccag atttatcagc | 1080 |
| aataaaccag ccagccggaa gggccgagcg cagaagtggt cctgcaactt tatccgcctc | 1140 |
| catccagtct attaattgtt gccgggaagc tagagtaagt agttcgccag ttaatagttt | 1200 |
| gcgcaacgtt gttgccattg ctacaggcat cgtggtgtca cgctcgtcgt ttggtatggc | 1260 |
| ttcattcagc tccggttccc aacgatcaag gcgagttaca tgatccccca tgttgtgcaa | 1320 |
| aaaagcggtt agctccttcg gtcctccgat cgttgtcaga agtaagttgg ccgcagtgtt | 1380 |
| atcactcatg gttatggcag cactgcataa ttctcttact gtcatgccat ccgtaagatg | 1440 |
| cttttctgtg actggtgagt actcaaccaa gtcattctga atagtgta tgcggcgacc | 1500 |
| gagttgctct tgcccggcgt caatacggga taataccgcg ccacatagca gaactttaaa | 1560 |
| agtgctcatc attggaaaac gttcttcggg gcgaaaactc tcaaggatct taccgctgtt | 1620 |
| gagatccagt tcgatgtaac ccactcgtgc acccaactga tcttcagcat cttttacttt | 1680 |
| caccagcgtt tctgggtgag caaaaacagg aaggcaaaat gccgcaaaaa agggaataag | 1740 |
| ggcgacacgg aaatgttgaa tactcatcaa ttgccttttt caatattatt gaagcattta | 1800 |
| tcagggttat tgtctcatga gcggttacat atttgaatgt atttagaaaa ataaacaaat | 1860 |
| aggggttccg cgcacatttc cccgaaaagt gccacctgac gtctaagaaa ccattattat | 1920 |
| catgacatta acctataaaa ataggcgtat cacgaggccc tttcatctcg cgcgtttcgg | 1980 |
| tgatgacggt gaaaacctct gacacatgca gctcccggag acagtcacag cttgtctgta | 2040 |
| agcggatgcc gggagcagac aagcccgtca gggcgcgtca gcgggtgttg gcgggtgtcg | 2100 |
| gggctggtaa aacgacggcc agtattaacc ctcactaaag ggaactcgag gctcttcacg | 2160 |
| ctcgtccaac gccggcggac ctaagccaat atccccaaaa ttattaagag cgcctccatt | 2220 |
| attaactaaa atttcactca gcatccacaa tgtatcaggt atctactaca gatattacat | 2280 |
| gtggcgaaaa agacaagaac aatgcaatag cgcatcaaga aaaacacaa agctttcaat | 2340 |
| caatgaatcg aaaatgtcat taaaatagta tataaattga aactaagtca taaagctata | 2400 |
| aaaagaaaat ttatttaaat gcaagattta aagtaaattc acttaatccc cgcgtgcttg | 2460 |
| gccggccgtt gaagagcgag ctcccgctga gcaataacta gcgtcatagc tgtttcctg | 2519 |

<210> SEQ ID NO 17
<211> LENGTH: 2121
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (2109)..(2109)
<223> OTHER INFORMATION: a, c, t, g, unknown or other

<400> SEQUENCE: 17

| | |
|---|---|
| gaattcgccc ttntggatgg cggcgttagt atcgaatcga cagcagtata gcgaccagca | 60 |

```
ttcacatacg attgacgcat gatattactt tctgcgcact taacttcgca tctgggcaga        120
tgatgtcgag gcgaaaaaaa atataaatca cgctaacatt tgattaaaat agaacaacta        180
caatataaaa aaactataca aatgacaagt tcttgaaaac aagaatcttt ttattgtcag        240
tactgattag aaaaactcat cgagcatcaa atgaaactgc aatttattca tatcaggatt        300
atcaatacca tattttgaa aaagccgttt ctgtaatgaa ggagaaaact caccgaggca         360
gttccatagg atggcaagat cctggtatcg gtctgcgatt ccgactcgtc caacatcaat        420
acaacctatt aatttcccct cgtcaaaaat aaggttatca agtgagaaat caccatgagt        480
gacgactgaa tccggtgaga atggcaaaag cttatgcatt tctttccaga cttgttcaac        540
aggccagcca ttacgctcgt catcaaaatc actcgcatca accaaaccgt tattcattcg        600
tgattgcgcc tgagcgagac gaaatacgcg atcgctgtta aaaggacaat acaaacagg         660
aatcgaatgc aaccggcgca ggaacactgc cagcgcatca acaatatttt cacctgaatc       720
aggatattct tctaatacct ggaatgctgt tttgccgggg atcgcagtgg tgagtaacca       780
tgcatcatca ggagtacgga taaaatgctt gatggtcgga agaggcataa attccgtcag       840
ccagtttagt ctgaccatct catctgtaac atcattggca acgctacctt tgccatgttt       900
cagaaacaac tctggcgcat cgggcttccc atacaatcga tagattgtcg cacctgattg       960
cccgacatta tcgcgagccc atttatacc atataaatca gcatccatgt tggaatttaa       1020
tcgcggcctc gaaacgtgag tcttttcctt acccatggtt gtttatgttc ggatgtgatg      1080
tgagaactgt atcctagcaa gatttttaaaa ggaagtatat gaaagaagaa cctcagtggc     1140
aaatcctaac cttttatatt tctctacagg ggcgcggcgt ggggacaatt caacgcgtct      1200
gtgaggggag cgtttccctg ctcgcaggtc tgcagcgagg agccgtaatt tttgcttcgc       1260
gccgtgcggc catcaaaatg tatggatgca aatgattata catggggatg tatgggctaa       1320
atgtacgggc gacagtcaca tcatgcccct gagctgcgca cgtcaagact gtcaaggagg       1380
gtattctggg cctccatgtc gctggccggg tgacccggcg gggacgaggc aagctaaaca       1440
gatctgatct tgaaactgag taagatgctc agaatacccg tcaagataag agtataatgt       1500
agagtaatat accaagtatt cagcatattc tcctcttctt ttgtataaat cacggaaggg       1560
atgatttata agaaaaatga atactattac acttcattta ccaccctctg atctagattt       1620
tccaacgata tgtacgtagt ggtataaggt gaggggtcc acagatataa catcgtttaa        1680
tttagtacta acagagactt ttgtcacaac tacatataag tgtacaaata tagtacagat       1740
atgacacact tgtagcgcca acgcgcatcc tacggattgc tgacagaaaa aaaggtcacg       1800
tgaccagaaa agtcacgtgt aattttgtaa ctcaccgcat tctagcggtc cctgtcgtgc       1860
acactgcact caacaccata aaccttagca acctccaaag gaaatcaccg tataacaaag       1920
ccacagtttt acaacttagt ctcttatgaa gttacttacc aatgagaaat agaggctctt       1980
tctcgagaaa tatgaatatg gatatatata tatatatata tatatatata tatatatgta      2040
aacttggttc tttttagct tgtgatctct agcttgggtc tctctctgtc gtaacagttg        2100
tgatatcgna agggcgaatt c                                                 2121
```

<210> SEQ ID NO 18
<211> LENGTH: 8425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatcga ctacgtcgta aggccgtttc tgacagagta aaattcttga gggaactttc   240
accattatgg gaaatgcttc aagaaggtat tgacttaaac tccatcaaat ggtcaggtca   300
ttgagtgttt tttatttgtt gtattttttt tttttagag aaaatcctcc aatatcaaat    360
taggaatcgt agtttcatga ttttctgtta cacctaactt tttgtgtggt gccctcctcc   420
ttgtcaatat taatgttaaa gtgcaattct ttttccttat cacgttgagc cattagtatc   480
aatttgctta cctgtattcc tttactatcc tcctttttct ccttcttgat aaatgtatgt   540
agattgcgta tatagtttcg tctaccctat gaacatattc cattttgtaa tttcgtgtcg   600
tttctattat gaatttcatt tataaagttt atgtacaaat atcataaaaa aagagaatct   660
ttttaagcaa ggatttttctt aacttcttcg gcgacagcat caccgacttc ggtggtactg   720
ttggaaccac ctaaatcacc agttctgata cctgcatcca aaaccttttt aactgcatct   780
tcaatggcct taccttcttc aggcaagttc aatgacaatt tcaacatcat tgcagcagac   840
aagatagtgg cgatagggtc aaccttattc tttggcaaat ctggagcaga accgtggcat   900
ggttcgtaca aaccaaatgc ggtgttcttg tctggcaaag aggccaagga cgcagatggc   960
aacaaaccca aggaacctgg gataacggag gcttcatcgg agatgatatc accaaacatg  1020
ttgctggtga ttataatacc atttaggtgg gttgggttct taactaggat catggcggca  1080
gaatcaatca attgatgttg aaccttcaat gtagggaatt cgttcttgat ggtttcctcc  1140
acagtttttc tccataatct tgaagaggcc aaaagattag ctttatccaa ggaccaaata  1200
ggcaatggtg gctcatgttg tagggccatg aaagcggcca ttcttgtgat tctttgcact  1260
tctggaacgg tgtattgttc actatcccaa gcgacaccat caccatcgtc ttcctttctc  1320
ttaccaaagt aaataccctcc cactaattct ctgacaacaa cgaagtcagt acctttagca  1380
aattgtggct tgattggaga taagtctaaa agagagtcgg atgcaaagtt acatggtctt  1440
aagttggcgt acaattgaag ttctttacgg attttttagta aaccttgttc aggtctaaca  1500
ctaccggtac cccatttagg accagccaca gcacctaaca aaacggcatc aaccttcttg  1560
gaggcttcca gcgcctcatc tggaagtggg acacctgtag catcgatagc agcaccacca  1620
attaaatgat tttcgaaatc gaacttgaca ttggaacgaa catcagaaat agctttaaga  1680
accttaatgg cttcggctgt gatttcttga ccaacgtggt cacctggcaa aacgacgatc  1740
ttcttagggg cagacattac aatggtatat ccttgaaata tatataaaaa aaggcgcctt  1800
agaccgctcg gccaaacaac caattacttg ttgagaaata gagtataatt atcctataaa  1860
tataacgttt ttgaacacac atgaacaagg aagtacagga caattgattt tgaagagaat  1920
gtggattttg atgtaattgt tgggattcca ttttttaataa ggcaataata ttaggtatgt  1980
ggatatacta gaagttctcc tcgaccgtcg atatgcggtg tgaaataccg cacagatgcg  2040
taaggagaaa ataccgcatc aggaaattgt aaacgttaat attttgttaa aattcgcgtt  2100
aaatttttgt taaatcagct cattttttaa ccaataggcc gaaatcggca aaatccctta  2160
taaatcaaaa gaatagaccg agatagggtt gagtgttgtt ccagtttgga acaagagtcc  2220
actattaaag aacgtggact ccaacgtcaa agggcgaaaa accgtctatc agggcgatgg  2280
cccactacgt ggaagatccg aggcctagct ttaacgaacg cagaattttc gagttattaa  2340
acttaaaata cgctgaaccc gaacatagaa atatcgaatg ggaaaaaaaa actgcataaa  2400
```

```
ggcattaaaa gaggagcgaa ttttttttta ataaaaatct taataatcat taaaagataa    2460
ataatagtct atatatacgt atataaataa aaaatattca aaaataaaa taaactatta     2520 ttttagcgta aaggatgggg aaagagaaaa gaaaaaatt gatctatcga tttcaattca     2580
attcaattta tttcttttcg gataagaaag caacacctgg caattcctta ccttccaata   2640
attccaaaga agcaccacca ccagtagaga catgggagac ccgggccatg gttagatga    2700 cataggtaa actagcaatg atttgatcaa atgcttgtat tcatctccca ttctcgtaaa    2760
attgtcttta cctgcatatt ggacctctaa aaattggcaa agatatataa cagccataag   2820
taaaggtctt gggatattct tgttgttaa atactctctg tttatgtctt tccaaacgtc    2880
ctccacttcc ttataaatca gtgtctgagc atattcttcg ttgacattgt attccttcat   2940
gtaagattct aaagagcttg aactatgttt tctctcctgt tccgctttat gagtcatcag   3000
gtcatttaat ctcctaccca gaataccact gtaacggaat aaaggcggag cagatacagc   3060
ccactcaact gattccttag tgaaaatatc gctcattcct agataacagg tagttgttag   3120
caagtttgca ccaccagtga taataactac gggatcgtgc tcttcagttg tcggtatgtg   3180
tccttcatta gcccatttcg cttctaccat tagattcctt acgaattctt taacgaactc   3240
cttcccacag ttgaataaat cagttctacc ttctttggcc agaaactcct ccatttctgt   3300
gtaggtatcc atgaataatt tgtaaatagg cttcatgtat tccggcaacg tgtctaagca   3360
ggtgatcgac catctttcca cggcttcagt gaaaatcttt aactcctcgt aagttccata   3420
tgcgtcatac gtgtcatcaa taagtgttat cacagcaact gccttagtga aaaaaactct   3480
agctcttgaa tactggggtt cgtaaccaga acctaaaccc caaaaatagc attcaacgat   3540
acgatctctc agacatgggg cattttcctt aatatcaaat gccttccacc acttgcatac   3600
gtgactcaac tcttccttat gtaggctctg caatagattg aactccagtt tagctaactt   3660
tagcagagtt ttattatggg agtcttgttg ctgatagaag ggtatgtact gggcggcctc   3720
gatccttggc aatctcttcc acaatggttg ctttaaagct ctctggattt cagtgaataa   3780
agcggggttt gtactaaacg cgtccttgt cataatcgat agccttgatc ttgtgaatcc    3840
cagggcatct tcaagaatta tttcgcccgg aactctcatg gacgtagcct catataattc   3900
caacaatcct tcaacatcat tcgctaacga ttgtttaaaa gcaccattct tgtctttata   3960
gttattaaac acatcacacg tgacatagta tccttgttta cgcatcagcc taaaccataa   4020
gctagacctg tcgccattcc aattatcacc ataggtctcg taaatacatt gcaatgcatg   4080
atcaatttca cgttcaaaat gatacggaat acctaaacgt tgaatctcgt caatcagctt   4140
caacaaattt gcatgtttca taggaatatc caatgcttcc tttaacaact gtcttacttc   4200
cttctttaga tcgtttacta tttgctccac accctgttca acttgtttct cataaatcaa   4260
aaattgatcg ccccaaatag aaggtgggaa atttgcaatt ggccttatag gtttctcttc   4320
agtcaaggcc attgttttct gcagatccgg ggttttttct ccttgacgtt aaagtataga   4380
ggtatattaa caattttttg ttgatacttt tattacattt gaataagaag taatacaaac   4440
cgaaaatgtt gaaagtatta gttaaagtgg ttatgcagtt tttgcattta tatatctgtt   4500
aatagatcaa aaatcatcgc ttcgctgatt aattacccca gaaataaggc taaaaaacta   4560
atcgcattat catcctatgg ttgttaattt gattcgttca tttgaaggtt tgtgggggcca  4620 ggttactgcc aattttttcct cttcataacc ataaaagcta gtattgtaga atctttattg   4680
ttcggagcag tgcggcgcga ggcacatctg cgtttcagga acgcgaccgg tgaagacgag   4740
gacgcacgga ggagagtctt ccttcggagg gctgtcaccc gctcggcggc ttctaatccg   4800
```

```
tactaagatc tgctttaatt tggccggcga acgtggcgag aaaggaaggg aagaaagcga    4860
aaggagcggg cgctagggcg ctggcaagtg tagcggtcac gctgcgcgta accaccacac    4920
ccgccgcgct taatgcgccg ctacaggcg cgtcgcgcca ttcgccattc aggctgcgca    4980
actgttggga agggcgatcg gtgcgggcct cttcgctatt acgccagctg cattaatgaa    5040
tcggccaacg cgcggggaga ggcggtttgc gtattgggcg ctcttccgct tcctcgctca    5100
ctgactcgct gcgctcggtc gttcggctgc ggcgagcggt atcagctcac tcaaaggcgg    5160
taatacggtt atccacagaa tcaggggata acgcaggaaa gaacatgtga gcaaaaggcc    5220
agcaaaaggc caggaaccgt aaaaaggccg cgttgctggc gtttttccat aggctccgcc    5280
cccctgacga gcatcacaaa aatcgacgct caagtcagag gtggcgaaac ccgacaggac    5340
tataaagata ccaggcgttt ccccctggaa gctccctcgt gcgctctcct gttccgaccc    5400
tgccgcttac cggatacctg tccgcctttc tcccttcggg aagcgtggcg ctttctcata    5460
gctcacgctg taggtatctc agttcggtgt aggtcgttcg ctccaagctg ggctgtgtgc    5520
acgaaccccc cgttcagccc gaccgctgcg ccttatccgg taactatcgt cttgagtcca    5580
acccggtaag acacgactta tcgccactgg cagcagccac tggtaacagg attagcagag    5640
cgaggtatgt aggcggtgct acagagttct tgaagtggtg gcctaactac ggctacacta    5700
gaaggacagt atttggtatc tgcgctctgc tgaagccagt taccttcgga aaaagagttg    5760
gtagctcttg atccggcaaa caaaccaccg ctggtagcgg tggtttttttt gtttgcaagc    5820 agcagattac gcgcagaaaa aaggatctc aagaagatcc tttgatcttt tctacggggt    5880
ctgacgctca gtggaacgaa aactcacgtt aagggatttt ggtcatgaga ttatcaaaaa    5940
ggatcttcac ctagatcctt ttaaattaaa aatgaagttt taaatcaatc taagtatat    6000 atgagtaaac ttggtctgac agttaccaat gcttaatcag tgaggcacct atctcagcga    6060
tctgtctatt tcgttcatcc atagttgcct gactccccgt cgtgtagata actacgatac    6120
gggagggctt accatctggc cccagtgctg caatgatacc gcgagaccca cgctcaccgg    6180
ctccagattt atcagcaata aaccagccag ccggaagggc cgagcgcaga agtggtcctg    6240
caactttatc cgcctccatc cagtctatta attgttgccg ggaagctaga gtaagtagtt    6300
cgccagttaa tagtttgcgc aacgttgttg ccattgctac aggcatcgtg gtgtcacgct    6360
cgtcgtttgg tatggcttca ttcagctccg gttcccaacg atcaaggcga gttacatgat    6420
cccccatgtt gtgcaaaaaa gcggttagct ccttcggtcc tccgatcgtt gtcagaagta    6480
agttggccgc agtgttatca ctcatggtta tggcagcact gcataattct cttactgtca    6540
tgccatccgt aagatgcttt tctgtgactg gtgagtactc aaccaagtca ttctgagaat    6600
agtgtatgcg gcgaccgagt tgctcttgcc cggcgtcaat acgggataat accgcgccac    6660
atagcagaac tttaaaagtg ctcatcattg gaaaacgttc ttcggggcga aaactctcaa    6720
ggatcttacc gctgttgaga tccagttcga tgtaacccac tcgtgcaccc aactgatctt    6780
cagcatcttt tactttcacc agcgtttctg ggtgagcaaa aacaggaagg caaaatgccg    6840
caaaaaaggg aataagggcg acacggaaat gttgaatact catactcttc cttttttcaat    6900 attattgaag catttatcag ggttattgtc tcatgagcgg atacatattt gaatgtattt    6960
agaaaaataa acaaataggg gttccgcgca catttccccg aaaagtgcca cctgaacgaa    7020
gcatctgtgc ttcattttgt agaacaaaaa tgcaacgcga gagcgctaat ttttcaaaca    7080
aagaatctga gctgcatttt tacagaacag aaatgcaacg cgaaagcgct attttaccaa    7140
cgaagaatct gtgcttcatt tttgtaaaac aaaaatgcaa cgcgagagcg ctaattttttc    7200
```

```
aaacaaagaa tctgagctgc attttttacag aacagaaatg caacgcgaga gcgctatttt   7260
accaacaaag aatctatact tcttttttgt tctacaaaaa tgcatcccga gagcgctatt   7320
tttctaacaa agcatcttag attactttt ttctcctttg tgcgctctat aatgcagtct   7380
cttgataact ttttgcactg taggtccgtt aaggttagaa gaaggctact ttggtgtcta   7440
ttttctcttc cataaaaaaa gcctgactcc acttcccgcg tttactgatt actagcgaag   7500
ctgcgggtgc attttttcaa gataaaggca tccccgatta tattctatac cgatgtggat   7560
tgcgcatact ttgtgaacag aaagtgatag cgttgatgat tcttcattgg tcagaaaatt   7620
atgaacggtt tcttctattt tgtctctata tactacgtat aggaaatgtt tacattttcg   7680
tattgttttc gattcactct atgaatagtt cttactacaa ttttttttgtc taaagagtaa   7740 tactagagat aaacataaaa aatgtagagg tcgagtttag atgcaagttc aaggagcgaa   7800
aggtggatgg gtaggttata tagggatata gcacagagat atatagcaaa gagatacttt   7860
tgagcaatgt ttgtggaagc ggtattcgca atattttagt agctcgttac agtccggtgc   7920 gttttttggtt ttttgaaagt gcgtcttcag agcgcttttg gttttcaaaa gcgctctgaa   7980
gttcctatac tttctagaga ataggaactt cggaatagga acttcaaagc gtttccgaaa   8040
acgagcgctt ccgaaaatgc aacgcgagct gcgcacatac agctcactgt tcacgtcgca   8100
cctatatctg cgtgttgcct gtatatatat atacatgaga agaacggcat agtgcgtgtt   8160
tatgcttaaa tgcgtactta tgcgtctca tttatgtagg atgaaaggta gtctagtacc   8220
tcctgtgata ttatcccatt ccatgcgggg tatcgtatgc ttccttcagc actacccttt   8280
agctgttcta tatgctgcca ctcctcaatt ggattagtct catccttcaa tgctatcatt   8340
tcctttgata ttggatcata ctaagaaacc attattatca tgacattaac ctataaaaat   8400
aggcgtatca cgaggccctt tcgtc                                        8425
```

<210> SEQ ID NO 19
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
gagtgaacct gctgcctggc gtgctctgac tcagtacatt tcatagtgga tggcggcgtt   60
agtatc                                                             66
```

<210> SEQ ID NO 20
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

```
cgtgtatacg ttttccgctt ctgctcttcg tcttttctct tcttccgata tcacaactgt   60
tacga                                                              65
```

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 21
taataaggat ccatgtcaac tttgcctatt tc                                   32

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttatagctag ctcaaacgac cataggatga ac                                   32

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtttaaacta ctattagctg aattgccact                                      30

<210> SEQ ID NO 24
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
actgcaaagt acacatatat cccgggtgtc agctctttta gatcgg                    46

<210> SEQ ID NO 25
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccgatctaaa agagctgaca cccgggatat atgtgtactt tgcagt                    46

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtttaaacgg cgtcagtcca ccagctaaca                                      30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 27
gtttaaactt gctaaattcg agtgaaacac                                           30

<210> SEQ ID NO 28
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aaagatgaat tgaaaagctt cccgggtatg gaccctgaaa ccacag                         46

<210> SEQ ID NO 29
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctgtggtttc agggtccata cccgggaagc ttttcaattc atcttt                         46

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gtttaaaccc aacaataata atgtcagatc                                           30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtttaaacta ctcagtatat taagtttcga                                           30

<210> SEQ ID NO 32
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
atctctcgca agagtcagac tgactcccgg gcgtgaataa gcttcgggtg acccttatgg          60
cattcttttt                                                                 70

<210> SEQ ID NO 33
<211> LENGTH: 70
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 33
aaaaagaatg ccataagggt cacccgaagc ttattcacgc ccgggagtca gtctgactct    60
tgcgagagat                                                          70

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtttaaacaa tttagtgtct gcgatgatga                                    30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gtttaaacta ttgtgagggt cagttatttc                                    30

<210> SEQ ID NO 36
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gcggggacga ggcaagctaa actttagtat attcttcgaa gaaa                    44

<210> SEQ ID NO 37
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tttcttcgaa gaatatacta aagtttagct tgcctcgtcc ccgc                    44

<210> SEQ ID NO 38
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
caatcaacgt ggagggtaat tctgctagcc tctcccgggt ggatggcggc gttagtatcg    60

<210> SEQ ID NO 39
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 39
cgatactaac gccgccatcc acccgggaga ggctagcaga attaccctcc acgttgattg    60

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gtttaaacgc cgccgttgtt gttattgtag                                     30

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gtttaaactt ttccaatagg tggttagcaa                                     30

<210> SEQ ID NO 42
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gggtgacccg gcggggacga ggcaagctaa acgtcttcct ttctcttacc aaagt         55

<210> SEQ ID NO 43
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
actttggtaa gagaaaggaa gacgtttagc ttgcctcgtc cccgccgggt caccc         55

<210> SEQ ID NO 44
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aatatcataa aaaagagaa tctttcccgg gtggatggcg gcgttagtat cgaatcgaca     60
gc                                                                   62

<210> SEQ ID NO 45
<211> LENGTH: 62
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 45
gctgtcgatt cgatactaac gccgccatcc acccgggaaa gattctcttt ttttatgata    60
tt                                                                   62

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gtttaaacgt gttaacgttt ctttcgccta cgtggaagga gaatc                    45

<210> SEQ ID NO 47
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tccccccggg ttaaaaaaaa tccttggact agtca                               35

<210> SEQ ID NO 48
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tccccccggg agttatgaca attacaacaa cagaa                               35

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tccccccggg tatatatata tcattgttat                                     30

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tccccccggg aaaagtaagt caaaaggcac                                     30

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 51 tcccccggg atggtctgct taaatttcat                                30

<210> SEQ ID NO 52
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52 tcccccggg tagcttgtac ccattaaaag aattttatca tgccg               45

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53 tcccccggg tttctcattc aagtggtaac                                30

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54 tcccccggg taaataaaga aaataaagtt                                30

<210> SEQ ID NO 55
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55 aattttgaa aattcaatat aaatggcttc agaaaagaa attagga              47

<210> SEQ ID NO 56
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tcctaatttc ttttctgaa gccatttata ttgaattttc aaaaatt             47

<210> SEQ ID NO 57
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
```
agttttcacc aattggtctg cagccattat agttttttct ccttgacgtt a    51

<210> SEQ ID NO 58
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
taacgtcaag gagaaaaaac tataatggct gcagaccaat tggtgaaaac t    51

<210> SEQ ID NO 59
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59 aattttgaa aattcaatat aaatgaaact ctcaactaaa ctttgtt    47

<210> SEQ ID NO 60
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aacaaagttt agttgagagt ttcatttata ttgaattttc aaaaatt    47

<210> SEQ ID NO 61
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61 aattttgaa aattcaatat aaatgtctca gaacgtttac attgtat    47

<210> SEQ ID NO 62
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
atacaatgta aacgttctga gacatttata ttgaattttc aaaaatt    47

<210> SEQ ID NO 63
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tgcagaagtt aagaacggta atgacattat agttttttct ccttgacgtt a    51

-continued

```
<210> SEQ ID NO 64
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
taacgtcaag gagaaaaaac tataatgtca ttaccgttct taacttctgc a            51

<210> SEQ ID NO 65
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
aatttttgaa aattcaatat aaatgtcaga gttgagagcc ttcagtg                 47

<210> SEQ ID NO 66
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cactgaaggc tctcaactct gacatttata ttgaattttc aaaaatt                 47

<210> SEQ ID NO 67
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ggtaacggat gctgtgtaaa cggtcattat agttttttct ccttgacgtt a            51

<210> SEQ ID NO 68
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
taacgtcaag gagaaaaaac tataatgacc gtttacacag catccgttac c            51

<210> SEQ ID NO 69
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
aatttttgaa aattcaatat aaatgactgc cgacaacaat agtatgc                 47

<210> SEQ ID NO 70
```

```
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gcatactatt gttgtcggca gtcatttata ttgaattttc aaaaatt              47

<210> SEQ ID NO 71
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ggtaagacgg ttgggtttta tcttttgcag ttggtactat taagaacaat cacaggaaac    60
agctatgacc                                                          70

<210> SEQ ID NO 72
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ttgcgttttg tactttggtt cgctcaattt tgcaggtaga taatcgaaaa gttgtaaaac    60
gacggccagt                                                          70

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tgaagagcga gctcccgctg                                               20

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tgaagagcct cgagttccct ttag                                          24

<210> SEQ ID NO 75
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
atatactagg aaaactcttt atttaataac aatgatatat atatattcca gtggtgcatg    60
``` aac                                                             63

<210> SEQ ID NO 76
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
aatttgtgag tttagtatac atgcatttac ttataataca gttttcaac gcattacgta    60 ggc                                                             63

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
cgctcgtcca acgccggcgg acct                                      24

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
acggccggcc aagcacgcgg ggat                                      24

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
atggctacca atttgttgtg cttgtctaac                                30

<210> SEQ ID NO 80
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tcagacatac atcaactgat taataggaaa agggtc                         36

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81

```
atggctaccg agttgttgtg cttg                                             24
```

<210> SEQ ID NO 82
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82

```
tcacctctca aaggtaata taggttcagt aataac                                 36
```

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83

```
atggccaccg agttgttgtg c                                                21
```

<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84

```
tcacctctca aaggtaaga ttggttc                                           27
```

<210> SEQ ID NO 85
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85

```
tttaaaggat ccatggctac caatttgttg tg                                    32
```

<210> SEQ ID NO 86
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86

```
tatttcgcta gctcagacat acatcaactg attaatag                              38
```

<210> SEQ ID NO 87
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87

```
tttaaaggat ccatggctac cgagttgttg tg                                    32
```

```
<210> SEQ ID NO 88
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
catatcgcta gctcacctct caaaaggtaa tataggttc                              39

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
aatttaggat ccatggccac cgagttgttg                                        30

<210> SEQ ID NO 90
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tatatcgcta gctcacctct caaaaggtaa gattggttc                              39

<210> SEQ ID NO 91
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
caaataggat ccatggcaaa ttaccagcct aatttg                                 36

<210> SEQ ID NO 92
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
caaataggat ccatggctaa ttacgagcca aactcatg                               38

<210> SEQ ID NO 93
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
caaataggat ccatggccaa ctacgagcca aattc                                  35

<210> SEQ ID NO 94
```

```
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gcgtacaaag gtaacttacc gtgaataacc aaggcagcga cc                          42

<210> SEQ ID NO 95
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95 ggctcccct ggccgcgtgt gagcttatat tgaattttca aaaattc                      47

<210> SEQ ID NO 96
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gctcacacgc ggccaggggg agccatggct accgagttgt tgtg                        44

<210> SEQ ID NO 97
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gctcacacgc ggccaggggg agccatggct aattacgagc caaactcatg                  50

<210> SEQ ID NO 98
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
aggtccgccg gcgttggacg agcgtcacct ctcaaaaggt aatatagg                    48

<210> SEQ ID NO 99
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ctagcgattc tcattggaat acgtcgacac tagtaataca catc                        44

<210> SEQ ID NO 100
<211> LENGTH: 95
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 100
cgatgcgttc aattcctcta ctaatttagg gaaaacgttc aagaatctct ctctcctaat    60 ttcttttct gaagccatct ttgtatagcc cttaa    95

<210> SEQ ID NO 101
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gatgtgtatt actagtgtcg acgtattcca atgagaatcg ctag    44

<210> SEQ ID NO 102
<211> LENGTH: 3901
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
gtttaaactt caaagctcga tgcctcataa acttcggtag ttatattact ctgagatgac    60
ttatactctt tttccaaatc cacattattt ggcgcaaagg tctcattgga agattccata   120
agttggcgag agttcaatct ttttgaagag ccgcttaaat gtaatgatag attgtctggc   180
attattccct cctattctta ttatgcgtag gaatgtcttc gaaccgaaag atcttctcta   240
tggggtatgc tttagagtga aattaagaaa ggagttttat acagatgata cctaatcatc   300
atataagtaa gagagaacag agatttaatg gaaaatggaa aagggcaaat tggcgctgaa   360
tcaaatagtt tattatatct ttacaatttg tccgtgatttt gtccttgtct aacttgaaaa   420
tttttcattc tgatgtcata cgactttttt ccggtctagg aaatcggtga aagcttttt    480 tttttcctat cttcttgtcc atcggaattt ttctgtcatt tcttttcctc ctcgcgcttg   540
tctactaaaa tctgaattgt ccaaattcag tacaaaatta atcagtagga caaagggttc   600
tcgtagagtc cccggaaaaa aaaaaggaca aaaagtttca agacggcaat ctctttttac   660
tgcatctcgt cagttggcaa cttgccaaga acttcgcaaa tgactttgac atatgataag   720
acgtcaactg ccccacgtac aataacaaaa tggtagtcat atcatgtcaa gataggtat   780 ccaaaacgca gcggttgaaa gcatatcaag aattttgtcc ctgtgtttta agtttgtgg   840 ataatcgaaa tctcttacat tgaaaacatt atcatacaat catttattaa gtagttgaag   900
catgtatgaa ctataaaagt gttactactc gttattattg cgtattttgt gatgctaaag   960
ttatgagtct cgagaagtta agattatatg ataactaaa tactaaatag aaatgtaaat  1020
acagtgagaa caaaacaaaa aaaaacgaac agagaaacta atccacatt aattgagagt   1080 tctatctatt agaaaatgca aactccaact aaatgggaaa acagataacc tctttattt   1140 ttttttaatg tttgatattc gagtcttttt cttttgttag gttatattc atcatttcaa   1200 tgaataaaag aagcttctta ttttggttgc aaagaatgaa aaaaaggat ttttcatac    1260 ttctaaagct tcaattataa ccaaaaattt tataaatgaa gagaaaaaat ctagtagtat  1320
caagttaaac ctattccttt gccctcggac gagtgctggg gcgtcggttt ccactatcgg  1380

```
cgagtacttc tacacagcca tcggtccaga cggccgcgct tctgcgggcg atttgtgtac   1440
gcccgacagt cccggctccg gatcggacga ttgcgtcgca tcgaccctgc gcccaagctg   1500
catcatcgaa attgccgtca accaagctct gatagagttg gtcaagacca atgcggagca   1560
tatacgcccg gagccgcggc gatcctgcaa gctccggatg cctccgctcg aagtagcgcg   1620
tctgctgctc catacaagcc aaccacggcc tccagaagaa gatgttggcg acctcgtatt   1680
gggaatcccc gaacatcgcc tcgctccagt caatgaccgc tgttatgcgg ccattgtccg   1740
tcaggacatt gttggagccg aaatccgcgt gcacgaggtg ccggacttcg ggcagtcct    1800 cggcccaaag catcagctca tcgagagcct gcgcgacgga cgcactgacg gtgtcgtcca   1860
tcacagtttg ccagtgatac acatggggat cagcaatcgc gcatatgaaa tcacgccatg   1920
tagtgtattg accgattcct tgcggtccga atgggccgaa cccgctcgtc tggctaagat   1980
cggccgcagc gatcgcatcc atggcctccg cgaccggctg cagaacagcg ggcagttcgg   2040
tttcaggcag gtcttgcaac gtgacaccct gtgcacggcg ggagatgcaa taggtcaggc   2100
tctcgctgaa ttccccaatg tcaagcactt ccggaatcgg gagcgcggcc gatgcaaagt   2160
gccgataaac ataacgatct ttgtagaaac catcggcgca gctatttacc cgcaggacat   2220
atccacgccc tcctacatcg aagctgaaag cacgagattc ttcgccctcc gagagctgca   2280
tcaggtcgga gacgctgtcg aacttttcga tcagaaactt ctcgacagac gtcgcggtga   2340
gttcaggctt tttcattttt aatgttactt ctcttgcagt tagggaacta taatgtaact   2400
caaaataaga ttaaacaaac taaaataaaa agaagttata cagaaaaacc catataaacc   2460
agtactaatc cataataata atacacaaaa aaactatcaa ataaaaccag aaaacagatt   2520
gaatagaaaa attttttcga tctccttta tattcaaaat tcgatatatg aaaaagggaa   2580
ctctcagaaa atcaccaaat caatttaatt agattttct tttccttcta gcgttggaaa    2640
gaaaattttt tcttttttt tttagaaatg aaaaatttt gccgtaggaa tcaccgtata    2700
aaccctgtat aaacgctact ctgttcacct gtgtaggcta tgattgaccc agtgttcatt   2760
gttattgcga gagagcggga gaaaagaacc gatacaagag atccatgctg gtatagttgt   2820
ctgtccaaca cttgatgaa cttgtaggac gatgatgtgt attactagtg tcgacactgc     2880
tgaagaattt gattttctta gccattccca tagacgttac aatccactaa ccgattcatg   2940
gatcttagtt tctccacaca gagctaaaag accttggtta ggtcaacagg aggctgctta   3000
caagcccaca gctccattgt atgatccaaa atgctatcta tgtcctggta acaaaagagc   3060
tactggtaac ctaaacccaa gatatgaatc aacgtatatt ttccccaatg attatgctgc   3120
cgttaggctc gatcaaccta ttttaccaca gaatgattcc aatgaggata atcttaaaaa   3180
taggctgctt aaagtgcaat ctgtgagagg caattgtttc gtcatatgtt ttagccccaa   3240
tcataatcta accattccac aaatgaaaca atcagatctg gttcatattg ttaattcttg   3300
gcaagcattg actgacgatc tctccagaga agcaagagaa aatcataagc ctttcaaata   3360
tgtccaaata tttgaaaaca aaggtacagc catgggttgt tccaacttac atccacatgg   3420
ccaagcttgg tgcttagaat ccatccctag tgaagtttcg caagaattga atcttttga    3480 taaatataaa cgtgaacaca atactgattt gtttgccgat tacgtcaaat tagaatcaag   3540
agagaagtca agagtcgtag tggagaatga atcctttatt gttgttgttc catactgggc   3600
catctggcca tttgagacct tggtcatttc aaagaagaag cttgcctcaa ttagccaatt   3660
taaccaaatg gtgaaggagg acctcgcctc gattttaaag caactaacta ttaagtatga   3720
taatttattt gaaacgagtt tcccatactc aatgggtatc catcaggctc ctttgaatgc   3780
```

```
gactggtgat gaattgagta atagttggtt tcacatgcat ttctacccac ctttactgag      3840
atcagctact gttcggaaat tcttggttgg ttttgaattg ttaggtgagc ctcgtttaaa      3900
c                                                                     3901

<210> SEQ ID NO 103
<211> LENGTH: 1118
<212> TYPE: DNA
<213> ORGANISM: Saccharomyces cerevisiae

<400> SEQUENCE: 103
accataccac agcttttcaa ttcaattcat cattttttt ttattctttt ttttgatttc        60
ggtttctttg aaattttttt gattcggtaa tctccgaaca gaaggaagaa cgaaggaagg      120
agcacagact tagattggta tatatacgca tatgtagtgt tgaagaaaca tgaaattgcc      180
cagtattctt aacccaactg cacagaacaa aaacctgcag gaaacgaaga taaatcatgt      240
cgaaagctac atataaggaa cgtgctgcta ctcatcctag tcctgttgct gccaagctat      300
ttaatatcat gcacgaaaag caaacaaact tgtgtgcttc attggatgtt cgtaccacca      360
aggaattact ggagttagtt gaagcattag gtcccaaaat ttgtttacta aaaacacatg      420
tggatatctt gactgatttt tccatggagg gcacagttaa gccgctaaag gcattatccg      480
ccaagtacaa ttttttactc ttcgaagaca gaaaatttgc tgacattggt aatacagtca      540
aattgcagta ctctgcgggt gtatacagaa tagcagaatg ggcagacatt acgaatgcac      600
acggtgtggt gggcccaggt attgttagcg gtttgaagca ggcggcagaa gaagtaacaa      660
aggaacctag aggccttttg atgttagcag aattgtcatg caagggctcc ctatctactg      720
gagaatatac taagggtact gttgacattg cgaagagcga caaagatttt gttatcggct      780
ttattgctca aagagacatg ggtggaagag atgaaggtta cgattggttg attatgacac      840
ccggtgtggg tttagatgac aagggagacg cattgggtca acagtataga accgtggatg      900
atgtggtctc tacaggatct gacattatta ttgttggaag aggactattt gcaaagggaa      960
gggatgctaa ggtagagggt gaacgttaca gaaaagcagg ctgggaagca tatttgagaa     1020
gatgcggcca gcaaaactaa aaaactgtat tataagtaaa tgcatgtata ctaaactcac     1080
aaattagagc ttcaatttaa ttatatcagt tattaccc                             1118

<210> SEQ ID NO 104
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
tccttattac tgcgatatac agtgtgaggt attctaagcg gtatattcac ctcgagaagt       60
taagattata                                                             70

<210> SEQ ID NO 105
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
atccccgcgt gcttggccgg ccgtttcgac actagtaata cacatc                      46
```

<210> SEQ ID NO 106
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
atcggcgctc gcggcctgca ggttagagct cctcgagaag ttaag            45

<210> SEQ ID NO 107
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
aacctgcagg ccgcgagcgc cgatatatat gtgtactttg cagttatg         48

<210> SEQ ID NO 108
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
cgaggaactc ttggtattct tgccacgact catctccatg cagttg           46

<210> SEQ ID NO 109
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
atatactagg aaaactcttt atttaataac aatgatatat atatattcca gtggtgcatg    60
aac                                                                 63

<210> SEQ ID NO 110
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
aatttgtgag tttagtatac atgcatttac ttataataca gttttttcaac gcattacgta  60 ggc                                                                 63

<210> SEQ ID NO 111
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ttctgtaatg aaggagaaaa ctcaccgagg cagttccata ggatgaccat accacagctt    60
ttcaa    65

<210> SEQ ID NO 112
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gccgcgcccc tgtagagaaa tataaaggt taggatttgc cactggggta ataactgata    60
taatt    65

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
tcgactctag gcagataagg    20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gtcgataacc atggtactcc    20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
atcctaagtc gtggctattg    20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
accgaatgat gctctagatg    20

<210> SEQ ID NO 117
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
tggcttcaga aaaagaaatt aggagagaga gattcttgaa cgttttccct accataccac    60
agcttttcaa    70

<210> SEQ ID NO 118
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
tatttttcaa taaagaatat cttccactac tgccatctgg cgtcataact gggtaataac    60
tgatataatt    70

<210> SEQ ID NO 119
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
attactgcag gacggtagca acaagaatat ag    32

<210> SEQ ID NO 120
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gaaataggca aagttgacat ttttgaggga atattcaact g    41

<210> SEQ ID NO 121
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
cagttgaata ttccctcaaa aatgtcaact tgcctatttc    41

<210> SEQ ID NO 122
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
tataggatcc cttcgagcgt cccaaaacct tc    32

<210> SEQ ID NO 123
<211> LENGTH: 44
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 123
ttgtgatgct aaagttatga gtctcgagaa gttaagatta tatg                    44

<210> SEQ ID NO 124
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
catataatct taacttctcg agactcataa ctttagcatc acaa                    44

<210> SEQ ID NO 125
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gtttaaactt caaagctcga tgcctcat                                      28

<210> SEQ ID NO 126
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gtttaaacga ggctcaccta acaattca                                      28

<210> SEQ ID NO 127
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gatgtgtatt actagtgtcg acactgctga agaatttgat tttt                    44

<210> SEQ ID NO 128
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
aaaaatcaaa ttcttcagca gtgtcgacac tagtaataca catc                    44
```